US009779635B2

(12) United States Patent
Zboray et al.

(10) Patent No.: US 9,779,635 B2
(45) Date of Patent: *Oct. 3, 2017

(54) IMPORTING AND ANALYZING EXTERNAL DATA USING A VIRTUAL REALITY WELDING SYSTEM

(71) Applicant: Lincoln Global, Inc., City of Industry, CA (US)

(72) Inventors: David Anthony Zboray, Trumbulla, CT (US); Matthew Alan Bennett, Milford, CT (US); Matthew Wayne Wallace, Farmington, CT (US); Jeremiah Hennessey, Manchester, CT (US); Yvette Christine Dudac, Southington, CT (US); Zachary Steven Lenker, Vernon, CT (US); Andrew Paul Lundell, New Britain, CT (US); Paul Dana, East Lyme, CT (US); Eric A. Preisz, Orlando, FL (US)

(73) Assignee: LINCOLN GLOBAL, INC., City of Industry, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/821,004

(22) Filed: Aug. 7, 2015

(65) Prior Publication Data

US 2015/0356888 A1    Dec. 10, 2015

Related U.S. Application Data

(63) Continuation of application No. 13/792,309, filed on Mar. 11, 2013, now Pat. No. 9,196,169, which is a
(Continued)

(51) Int. Cl.
*G09B 19/24* (2006.01)
*G09B 5/02* (2006.01)
(Continued)

(52) U.S. Cl.
CPC .............. *G09B 19/24* (2013.01); *A42B 3/042* (2013.01); *A42B 3/30* (2013.01); *B23K 9/00* (2013.01);
(Continued)

(58) Field of Classification Search
CPC .......... G09B 19/24; B23K 9/09; B23K 9/095
See application file for complete search history.

(56) References Cited

U.S. PATENT DOCUMENTS

| 317,063 A | 5/1885 | Wittenstrom |
| 428,459 A | 5/1890 | Oopfin |

(Continued)

FOREIGN PATENT DOCUMENTS

| CA | 2698078 | 9/2011 |
| CN | 101209512 A | 7/2008 |

(Continued)

OTHER PUBLICATIONS

ARC+—Archived Press Release from WayBack Machine from Jan. 31, 2008—Apr. 22, 2013, Page, https://web.archive.org/web/20121006041803/http://www.123certification.com/en/article_press/index.htm, Jan. 21, 2016, 3 pages.
(Continued)

*Primary Examiner* — Robert J Utama
(74) *Attorney, Agent, or Firm* — Perkins Coie, LLP.

(57) ABSTRACT

A real-time virtual reality welding system including a programmable processor-based subsystem, a spatial tracker operatively connected to the programmable processor-based subsystem, at least one mock welding tool capable of being spatially tracked by the spatial tracker, and at least one display device operatively connected to the programmable processor-based subsystem. The system is capable of simulating, in virtual reality space, a weld puddle having real-time molten metal fluidity and heat dissipation characteris- (Continued)

tics. The system is further capable of importing data into the virtual reality welding system and analyzing the data to characterize a student welder's progress and to provide training.

42 Claims, 28 Drawing Sheets

Related U.S. Application Data continuation-in-part of application No. 12/501,257, filed on Jul. 10, 2009, now Pat. No. 8,747,116.

(60) Provisional application No. 61/090,794, filed on Aug. 21, 2008.

(51) Int. Cl.
*A42B 3/04* (2006.01)
*A42B 3/30* (2006.01)
*G09B 5/00* (2006.01)
*B23K 9/00* (2006.01)
*G09B 5/06* (2006.01)
*B23K 9/09* (2006.01)
*H04L 29/06* (2006.01)
*B23K 9/095* (2006.01)
*B23K 9/10* (2006.01)

(52) U.S. Cl.
CPC ............... *G09B 5/00* (2013.01); *G09B 5/02* (2013.01); *G09B 5/06* (2013.01); *G09B 5/065* (2013.01); *B23K 9/09* (2013.01); *B23K 9/095* (2013.01); *B23K 9/10* (2013.01); *H04L 29/06034* (2013.01)

(56) References Cited

U.S. PATENT DOCUMENTS

| | | |
|---|---|---|
| 483,428 A | 9/1892 | Goppin |
| 1,159,119 A | 11/1915 | Springer |
| D140,630 S | 3/1945 | Garibay |
| D142,377 S | 9/1945 | Dunn |
| D152,049 S | 12/1948 | Welch |
| 2,681,969 A | 6/1954 | Burke |
| D174,208 S | 3/1955 | Abidgaard |
| 2,728,838 A | 12/1955 | Barnes |
| D176,942 S | 2/1956 | Cross |
| 2,894,086 A | 7/1959 | Rizer |
| 3,035,155 A | 5/1962 | Hawk |
| 3,059,519 A | 10/1962 | Stanton |
| 3,356,823 A | 12/1967 | Waters et al. |
| 3,555,239 A | 1/1971 | Kerth |
| 3,621,177 A | 11/1971 | McPherson et al. |
| 3,654,421 A | 4/1972 | Streetman et al. |
| 3,739,140 A | 6/1973 | Rotilio |
| 3,866,011 A | 2/1975 | Cole |
| 3,867,769 A | 2/1975 | Schow et al. |
| 3,904,845 A | 9/1975 | Minkiewicz |
| 3,988,913 A | 11/1976 | Metcalfe et al. |
| D243,459 S | 2/1977 | Bliss |
| 4,024,371 A | 5/1977 | Drake |
| 4,041,615 A | 8/1977 | Whitehill |
| D247,421 S | 3/1978 | Driscoll |
| 4,124,944 A | 11/1978 | Blair |
| 4,132,014 A | 1/1979 | Schow |
| 4,237,365 A | 12/1980 | Lambros et al. |
| 4,280,041 A | 7/1981 | Kiesslilng et al. |
| 4,280,042 A | 7/1981 | Berger |
| 4,280,137 A | 7/1981 | Ashida et al. |
| 4,314,125 A | 2/1982 | Nakamura |
| 4,354,087 A | 10/1982 | Osterlitz |
| 4,359,622 A | 11/1982 | Dostoomian et al. |
| 4,375,026 A | 2/1983 | Kearney |
| 4,410,787 A | 10/1983 | Kremers et al. |
| 4,429,266 A | 1/1984 | Tradt |
| 4,452,589 A | 6/1984 | Denison |
| D275,292 S | 8/1984 | Bouman |
| D277,761 S | 2/1985 | Korovin et al. |
| 4,525,619 A | 6/1985 | Ide |
| D280,329 S | 8/1985 | Bouman |
| 4,611,111 A | 9/1986 | Baheti et al. |
| 4,616,326 A | 10/1986 | Meier et al. |
| 4,629,860 A | 12/1986 | Lindbom |
| 4,677,277 A | 6/1987 | Cook et al. |
| 4,680,014 A | 7/1987 | Paton et al. |
| 4,689,021 A | 8/1987 | Vasiliev et al. |
| 4,707,582 A | 11/1987 | Beyer |
| 4,716,273 A | 12/1987 | Paton et al. |
| D297,704 S | 9/1988 | Bulow |
| 4,867,685 A | 9/1989 | Brush et al. |
| 4,877,940 A | 10/1989 | Bangs et al. |
| 4,897,521 A | 1/1990 | Burr |
| 4,907,973 A | 3/1990 | Hon |
| 4,931,018 A | 6/1990 | Herbst et al. |
| 4,973,814 A | 11/1990 | Kojima |
| 4,998,050 A | 3/1991 | Nishiyama et al. |
| 5,034,593 A | 7/1991 | Rice et al. |
| 5,061,841 A | 10/1991 | Richardson |
| 5,089,914 A | 2/1992 | Prescott |
| 5,192,845 A | 3/1993 | Kirmsse et al. |
| 5,206,472 A | 4/1993 | Myking et al. |
| 5,266,930 A | 11/1993 | Ichikawa et al. |
| 5,285,916 A | 2/1994 | Ross |
| 5,305,183 A | 4/1994 | Teynor |
| 5,320,538 A | 6/1994 | Baum |
| 5,337,611 A | 8/1994 | Fleming et al. |
| 5,360,156 A | 11/1994 | Ishizaka et al. |
| 5,360,960 A | 11/1994 | Shirk |
| 5,370,071 A | 12/1994 | Ackermann |
| D359,296 S | 6/1995 | Witherspoon |
| 5,424,634 A | 6/1995 | Goldfarb et al. |
| 5,436,638 A | 7/1995 | Bolas et al. |
| 5,464,957 A | 11/1995 | Kidwell et al. |
| D365,583 S | 12/1995 | Viken |
| 5,562,843 A | 10/1996 | Yasumoto |
| 5,670,071 A | 9/1997 | Ueyama et al. |
| 5,676,503 A | 10/1997 | Lang |
| 5,676,867 A | 10/1997 | Allen |
| 5,708,253 A | 1/1998 | Bloch et al. |
| 5,710,405 A | 1/1998 | Solomon et al. |
| 5,719,369 A | 2/1998 | White et al. |
| D392,534 S | 3/1998 | Degen et al. |
| 5,728,991 A | 3/1998 | Takada et al. |
| 5,751,258 A | 5/1998 | Fergason et al. |
| D395,296 S | 6/1998 | Kaye et al. |
| D396,238 S | 7/1998 | Schmitt |
| 5,781,258 A | 7/1998 | Dabral et al. |
| 5,823,785 A | 10/1998 | Matherne, Jr. |
| 5,835,077 A | 11/1998 | Dao et al. |
| 5,835,277 A | 11/1998 | Hegg |
| 5,845,053 A | 12/1998 | Watanabe et al. |
| 5,877,777 A | 3/1999 | Colwell |
| 5,963,891 A | 10/1999 | Walker |
| 6,008,470 A | 12/1999 | Zhang et al. |
| 6,037,948 A | 3/2000 | Liepa |
| 6,049,059 A | 4/2000 | Kim |
| 6,051,805 A | 4/2000 | Vaidya et al. |
| 6,114,645 A | 9/2000 | Burgess |
| 6,155,475 A | 12/2000 | Ekelof et al. |
| 6,155,928 A | 12/2000 | Burdick |
| 6,230,327 B1 | 5/2001 | Briand et al. |
| 6,236,013 B1 | 5/2001 | Delzenne |
| 6,236,017 B1 | 5/2001 | Smartt et al. |
| 6,242,711 B1 | 6/2001 | Cooper |
| 6,271,500 B1 | 8/2001 | Hirayama et al. |
| 6,330,938 B1 | 12/2001 | Herve et al. |
| 6,330,966 B1 | 12/2001 | Eissfeller |
| 6,331,848 B1 | 12/2001 | Stove et al. |
| D456,428 S | 4/2002 | Aronson et al. |
| 6,373,465 B2 | 4/2002 | Jolly et al. |
| D456,828 S | 5/2002 | Aronson et al. |
| D461,383 S | 8/2002 | Balckburn |

(56) References Cited

U.S. PATENT DOCUMENTS

| | | |
|---|---|---|
| 6,441,342 B1 | 8/2002 | Hsu |
| 6,445,964 B1 | 9/2002 | White et al. |
| 6,492,618 B1 | 12/2002 | Flood et al. |
| 6,506,997 B2 | 1/2003 | Matsuyama |
| 6,552,303 B1 | 4/2003 | Blankenship et al. |
| 6,560,029 B1 | 5/2003 | Dobbie et al. |
| 6,563,489 B1 | 5/2003 | Latypov et al. |
| 6,568,846 B1 | 5/2003 | Cote et al. |
| D475,726 S | 6/2003 | Suga et al. |
| 6,572,379 B1 | 6/2003 | Sears et al. |
| 6,583,386 B1 | 6/2003 | Ivkovich |
| 6,621,049 B2 | 9/2003 | Suzuki |
| 6,624,388 B1 | 9/2003 | Blankenship et al. |
| D482,171 S | 11/2003 | Vui et al. |
| 6,647,288 B2 | 11/2003 | Madill et al. |
| 6,649,858 B2 | 11/2003 | Wakeman |
| 6,655,645 B1 | 12/2003 | Lu et al. |
| 6,660,965 B2 | 12/2003 | Simpson |
| 6,697,701 B2 | 2/2004 | Hillen et al. |
| 6,697,770 B1 | 2/2004 | Nagetgaal |
| 6,703,585 B2 | 3/2004 | Suzuki |
| 6,708,385 B1 | 3/2004 | Lemelson |
| 6,710,298 B2 | 3/2004 | Eriksson |
| 6,710,299 B2 | 3/2004 | Blankenship et al. |
| 6,715,502 B1 | 4/2004 | Rome et al. |
| D490,347 S | 5/2004 | Meyers |
| 6,730,875 B2 | 5/2004 | Hsu |
| 6,734,393 B1 | 5/2004 | Friedl et al. |
| 6,744,011 B1 | 6/2004 | Hu et al. |
| 6,750,428 B2 | 6/2004 | Okamoto et al. |
| 6,765,584 B1 | 7/2004 | Wloka et al. |
| 6,772,802 B2 | 8/2004 | Few |
| 6,788,442 B1 | 9/2004 | Potin et al. |
| 6,795,778 B2 | 9/2004 | Dodge et al. |
| 6,798,974 B1 | 9/2004 | Nakano et al. |
| 6,857,553 B1 | 2/2005 | Hartman et al. |
| 6,858,817 B2 | 2/2005 | Blankenship et al. |
| 6,865,926 B2 | 3/2005 | O'Brien et al. |
| D504,449 S | 4/2005 | Butchko |
| 6,920,371 B2 | 7/2005 | Hillen et al. |
| 6,940,037 B1 | 9/2005 | Kovacevic |
| 6,940,039 B2 | 9/2005 | Blankenship et al. |
| 7,021,937 B2 | 4/2006 | Simpson et al. |
| 7,024,342 B1 | 4/2006 | Waite |
| 7,126,078 B2 | 10/2006 | Demers et al. |
| 7,132,617 B2 | 11/2006 | Lee et al. |
| 7,170,032 B2 | 1/2007 | Flood |
| 7,194,447 B2 | 3/2007 | Harvey et al. |
| 7,247,814 B2 | 7/2007 | Ott |
| D555,446 S | 11/2007 | Picaza Ibarrondo |
| 7,315,241 B1 | 1/2008 | Daily et al. |
| D561,973 S | 2/2008 | Kinsley et al. |
| 7,353,715 B2 | 4/2008 | Myers |
| 7,363,137 B2 | 4/2008 | Brant et al. |
| 7,375,304 B2 | 5/2008 | Kainec et al. |
| 7,381,923 B2 | 6/2008 | Gordon et al. |
| 7,414,595 B1 | 8/2008 | Muffler |
| 7,465,230 B2 | 12/2008 | LeMay et al. |
| 7,478,108 B2 | 1/2009 | Townsend et al. |
| D587,975 S | 3/2009 | Aronson et al. |
| 7,516,022 B2 | 4/2009 | Lee et al. |
| 7,580,821 B2 | 8/2009 | Schirm |
| D602,057 S | 10/2009 | Osicki |
| 7,621,171 B2 | 11/2009 | O'Brien |
| D606,102 S | 12/2009 | Bender et al. |
| 7,643,890 B1 | 1/2010 | Hillen et al. |
| 7,687,741 B2 | 3/2010 | Kainec et al. |
| D614,217 S | 4/2010 | Peters et al. |
| D615,573 S | 5/2010 | Peters et al. |
| 7,817,162 B2 | 10/2010 | Bolick et al. |
| 7,853,645 B2 | 12/2010 | Brown et al. |
| D631,074 S | 1/2011 | Peters et al. |
| 7,874,921 B2 | 1/2011 | Baszucki et al. |
| 7,970,172 B1 | 6/2011 | Hendrickson |
| 7,972,129 B2 | 7/2011 | O'Donoghue |
| 7,991,587 B2 | 8/2011 | Ihn |
| 8,069,017 B2 | 11/2011 | Hallquist |
| 8,224,881 B1 | 7/2012 | Spear et al. |
| 8,248,324 B2 | 8/2012 | Nangle |
| 8,265,886 B2 | 9/2012 | Bisiaux et al. |
| 8,274,013 B2 | 9/2012 | Wallace |
| 8,287,522 B2 | 10/2012 | Moses et al. |
| 8,316,462 B2 | 11/2012 | Becker et al. |
| 8,363,048 B2 | 1/2013 | Gering |
| 8,365,603 B2 | 2/2013 | Lesage et al. |
| 8,512,043 B2 | 8/2013 | Choquet |
| 8,569,646 B2 | 10/2013 | Daniel et al. |
| 8,657,605 B2 | 2/2014 | Wallace et al. |
| 8,680,434 B2 | 3/2014 | Stoger |
| 8,747,116 B2 | 6/2014 | Zboray |
| 8,777,629 B2 | 7/2014 | Kreindl et al. |
| 8,834,168 B2 | 9/2014 | Peters et al. |
| 8,851,896 B2 | 10/2014 | Wallace |
| RE45,398 E | 3/2015 | Wallace |
| 8,992,226 B1 | 3/2015 | Leach |
| 9,011,154 B2 | 4/2015 | Kindig et al. |
| 9,196,169 B2 | 11/2015 | Wallace et al. |
| 9,280,913 B2 | 3/2016 | Peters et al. |
| 9,293,056 B2 | 3/2016 | Zboray et al. |
| 9,293,057 B2 | 3/2016 | Zboray et al. |
| 9,318,026 B2 | 4/2016 | Peters |
| 2001/0045808 A1 | 11/2001 | Hietmann et al. |
| 2001/0052893 A1 | 12/2001 | Jolly et al. |
| 2002/0032553 A1 | 3/2002 | Simpson et al. |
| 2002/0046999 A1 | 4/2002 | Veikkolainen et al. |
| 2002/0050984 A1 | 5/2002 | Roberts |
| 2002/0085843 A1 | 7/2002 | Mann |
| 2002/0175897 A1 | 11/2002 | Pelosi |
| 2003/0000931 A1 | 1/2003 | Ueda et al. |
| 2003/0023592 A1 | 1/2003 | Modica et al. |
| 2003/0025884 A1 | 2/2003 | Hamana et al. |
| 2003/0075534 A1 | 4/2003 | Okamoto |
| 2003/0106787 A1 | 6/2003 | Santilli |
| 2003/0111451 A1 | 6/2003 | Blankenship et al. |
| 2003/0172032 A1 | 9/2003 | Choquet |
| 2003/0186199 A1 | 10/2003 | McCool et al. |
| 2003/0234885 A1 | 12/2003 | Pilu |
| 2004/0020907 A1 | 2/2004 | Zauner et al. |
| 2004/0035990 A1 | 2/2004 | Ackeret |
| 2004/0050824 A1 | 3/2004 | Samler |
| 2001/0088071 | 5/2004 | Kouno |
| 2004/0140301 A1 | 7/2004 | Blankenship et al. |
| 2004/0181382 A1 | 9/2004 | Hu et al. |
| 2004/0217096 A1 | 11/2004 | Lipnevicius |
| 2005/0007504 A1 | 1/2005 | Fergason |
| 2005/0017152 A1 | 1/2005 | Fergason |
| 2005/0046584 A1 | 3/2005 | Breed |
| 2005/0050168 A1 | 3/2005 | Wen et al. |
| 2005/0101767 A1 | 5/2005 | Clapham et al. |
| 2005/0103766 A1 | 5/2005 | Iizuka et al. |
| 2005/0103767 A1 | 5/2005 | Kainec et al. |
| 2005/0109735 A1 | 5/2005 | Flood |
| 2005/0128186 A1 | 6/2005 | Shahoian et al. |
| 2005/0133488 A1 | 6/2005 | Blankenship |
| 2005/0159840 A1 | 7/2005 | Lin et al. |
| 2005/0163364 A1 | 7/2005 | Beck et al. |
| 2005/0189336 A1 | 9/2005 | Ku |
| 2005/0199602 A1 | 9/2005 | Kaddani et al. |
| 2005/0230573 A1 | 10/2005 | Ligertwood |
| 2005/0252897 A1 | 11/2005 | Hsu |
| 2005/0275913 A1 | 12/2005 | Vesely et al. |
| 2005/0275914 A1 | 12/2005 | Vesely et al. |
| 2006/0014130 A1 | 1/2006 | Weinstein |
| 2006/0076321 A1 | 4/2006 | Maev et al. |
| 2006/0136183 A1 | 6/2006 | Choquet |
| 2006/0142656 A1 | 6/2006 | Malackowski et al. |
| 2006/0154226 A1 | 7/2006 | Maxfield |
| 2006/0163227 A1 | 7/2006 | Hillen et al. |
| 2006/0166174 A1 | 7/2006 | Rowe |
| 2006/0169682 A1 | 8/2006 | Kainec et al. |
| 2006/0173619 A1 | 8/2006 | Brant et al. |
| 2006/0189260 A1 | 8/2006 | Sung |
| 2006/0207980 A1 | 9/2006 | Jacovetty et al. |
| 2006/0213892 A1 | 9/2006 | Ott |

(56) References Cited

U.S. PATENT DOCUMENTS

| | | |
|---|---|---|
| 2006/0214924 A1 | 9/2006 | Kawamoto et al. |
| 2006/0226137 A1 | 10/2006 | Huismann et al. |
| 2006/0252543 A1 | 11/2006 | Van Noland et al. |
| 2006/0258447 A1 | 11/2006 | Baszucki et al. |
| 2007/0034611 A1 | 2/2007 | Drius et al. |
| 2007/0038400 A1 | 2/2007 | Lee et al. |
| 2007/0045488 A1 | 3/2007 | Shin |
| 2007/0088536 A1 | 4/2007 | Ishikawa |
| 2007/0112889 A1 | 5/2007 | Cook et al. |
| 2007/0198117 A1 | 8/2007 | Wajihuddin |
| 2007/0209586 A1 | 9/2007 | Ebensberger |
| 2007/0211026 A1 | 9/2007 | Ohta |
| 2007/0221797 A1 | 9/2007 | Thompson et al. |
| 2007/0256503 A1 | 11/2007 | Wong et al. |
| 2007/0277611 A1 | 12/2007 | Portzgen et al. |
| 2007/0291035 A1 | 12/2007 | Vesely et al. |
| 2008/0021311 A1 | 1/2008 | Goldbach |
| 2008/0031774 A1 | 2/2008 | Magnant et al. |
| 2008/0038702 A1 | 2/2008 | Choquet |
| 2008/0061113 A9 | 3/2008 | Seki |
| 2008/0078811 A1 | 4/2008 | Hillen et al. |
| 2008/0078812 A1 | 4/2008 | Peters et al. |
| 2008/0117203 A1 | 5/2008 | Gering |
| 2008/0120075 A1 | 5/2008 | Wloka |
| 2008/0128398 A1 | 6/2008 | Schneider |
| 2008/0135533 A1 | 6/2008 | Ertmer et al. |
| 2008/0140815 A1 | 6/2008 | Brant et al. |
| 2008/0149686 A1 | 6/2008 | Daniel et al. |
| 2008/0203075 A1 | 8/2008 | Feldhausen et al. |
| 2008/0233550 A1 | 9/2008 | Solomon |
| 2008/0303197 A1 | 12/2008 | Paquette |
| 2008/0314887 A1 | 12/2008 | Stoger et al. |
| 2009/0015585 A1 | 1/2009 | Klusza |
| 2009/0021514 A1 | 1/2009 | Klusza |
| 2009/0045183 A1 | 2/2009 | Artelsmair et al. |
| 2009/0057286 A1 | 3/2009 | Ihara et al. |
| 2009/0152251 A1 | 6/2009 | Dantinne et al. |
| 2009/0173726 A1 | 7/2009 | Davidson et al. |
| 2009/0184098 A1 | 7/2009 | Daniel et al. |
| 2009/0200281 A1 | 8/2009 | Hampton |
| 2009/0200282 A1 | 8/2009 | Hampton |
| 2009/0231423 A1 | 9/2009 | Becker et al. |
| 2009/0259444 A1 | 10/2009 | Dolansky et al. |
| 2009/0298024 A1 | 12/2009 | Batzler et al. |
| 2009/0325699 A1 | 12/2009 | Delgiannidis |
| 2010/0012017 A1 | 1/2010 | Miller |
| 2010/0012637 A1 | 1/2010 | Jaeger |
| 2010/0048273 A1 | 2/2010 | Wallace et al. |
| 2010/0062405 A1 | 3/2010 | Zboray et al. |
| 2010/0062406 A1 | 3/2010 | Zboray et al. |
| 2010/0096373 A1 | 4/2010 | Hillen et al. |
| 2010/0121472 A1 | 5/2010 | Babu et al. |
| 2010/0133247 A1 | 6/2010 | Mazumder et al. |
| 2010/0133250 A1 | 6/2010 | Sardy et al. |
| 2010/0176107 A1 | 7/2010 | Bong |
| 2010/0201803 A1 | 8/2010 | Melikian |
| 2010/0224610 A1 | 9/2010 | Wallace |
| 2010/0276396 A1 | 11/2010 | Cooper et al. |
| 2010/0299101 A1 | 11/2010 | Shimada et al. |
| 2010/0307249 A1 | 12/2010 | Lesage et al. |
| 2011/0006047 A1 | 1/2011 | Penrod et al. |
| 2011/0060568 A1 | 3/2011 | Goldfine et al. |
| 2011/0091846 A1 | 4/2011 | Kreindl et al. |
| 2011/0114615 A1 | 5/2011 | Daniel et al. |
| 2011/0116076 A1 | 5/2011 | Chantry et al. |
| 2011/0117527 A1 | 5/2011 | Conrardy et al. |
| 2011/0122495 A1 | 5/2011 | Togashi |
| 2011/0183304 A1 | 7/2011 | Wallace et al. |
| 2011/0187746 A1 | 8/2011 | Suto et al. |
| 2011/0248864 A1 | 10/2011 | Becker et al. |
| 2011/0290765 A1 | 12/2011 | Albrecht et al. |
| 2011/0316516 A1 | 12/2011 | Schiefermuller et al. |
| 2012/0122062 A1 | 5/2012 | Yang |
| 2012/0189993 A1 | 7/2012 | Kindig et al. |
| 2012/0291172 A1 | 11/2012 | Wills et al. |
| 2012/0298640 A1 | 11/2012 | Conrardy et al. |
| 2013/0026150 A1 | 1/2013 | Chantry et al. |
| 2013/0040270 A1 | 2/2013 | Albrecht |
| 2013/0049976 A1 | 2/2013 | Maggiore |
| 2013/0075380 A1 | 3/2013 | Albrech et al. |
| 2013/0182070 A1 | 7/2013 | Peters et al. |
| 2013/0183645 A1 | 7/2013 | Wallace et al. |
| 2013/0189657 A1 | 7/2013 | Wallace et al. |
| 2013/0189658 A1 | 7/2013 | Peters et al. |
| 2013/0209976 A1 | 8/2013 | Postlethwaite et al. |
| 2013/0230832 A1 | 9/2013 | Peters |
| 2013/0231980 A1 | 9/2013 | Elgart |
| 2013/0327747 A1 | 12/2013 | Dantinne |
| 2014/0017642 A1 | 1/2014 | Postlethwaite et al. |
| 2014/0038143 A1 | 2/2014 | Daniel et al. |
| 2014/0065584 A1 | 3/2014 | Wallace et al. |
| 2014/0134579 A1 | 5/2014 | Becker |
| 2014/0134580 A1 | 5/2014 | Becker |
| 2014/0263224 A1 | 9/2014 | Becker |
| 2014/0272835 A1 | 9/2014 | Becker |
| 2014/0272836 A1 | 9/2014 | Becker |
| 2014/0272837 A1 | 9/2014 | Becker |
| 2014/0272838 A1 | 9/2014 | Becker |
| 2014/0312020 A1 | 10/2014 | Daniel |
| 2014/0315167 A1 | 10/2014 | Kreindl |
| 2014/0322684 A1 | 10/2014 | Wallace |
| 2014/0346158 A1 | 11/2014 | Matthews |
| 2015/0056584 A1 | 2/2015 | Boulware et al. |
| 2015/0056585 A1 | 2/2015 | Boulware et al. |
| 2015/0056586 A1 | 2/2015 | Penrod et al. |

FOREIGN PATENT DOCUMENTS

| | | |
|---|---|---|
| CN | 101214178 | 7/2008 |
| CN | 201083660 Y | 7/2008 |
| CN | 101419755 A1 | 4/2009 |
| CN | 201229711 Y | 4/2009 |
| CN | 101571887 A | 11/2009 |
| CN | 101587659 A | 11/2009 |
| CN | 102165504 | 8/2011 |
| CN | 202684308 U | 1/2013 |
| CN | 103871279 A | 6/2014 |
| CN | 102014819 | 7/2014 |
| DE | 28 33 638 A1 | 2/1980 |
| DE | 30 46 634 A1 | 1/1984 |
| DE | 32 44 307 A1 | 5/1984 |
| DE | 35 22 581 A1 | 1/1987 |
| DE | 4037879 A1 | 6/1991 |
| DE | 196 15 069 A1 | 10/1997 |
| DE | 197 39 720 C1 | 10/1998 |
| DE | 19834205 A1 | 2/2000 |
| DE | 200 09 543 U1 | 8/2001 |
| DE | 10 2005 047 204 A1 | 4/2007 |
| DE | 10 2010 038 902 A1 | 2/2012 |
| DE | 202012013151 U1 | 2/2015 |
| EP | 0 108 599 A1 | 5/1984 |
| EP | 0 127 299 | 12/1984 |
| EP | 0 145 891 A1 | 6/1985 |
| EP | 319623 B1 | 10/1990 |
| EP | 0852986 A1 | 7/1998 |
| EP | 1 527 852 A1 | 5/2005 |
| EP | 1905533 A2 | 4/2008 |
| ES | 2 274 736 A1 | 5/2007 |
| FR | 1456780 | 3/1965 |
| FR | 2827066 | 4/2001 |
| FR | 2 827 066 A1 | 1/2003 |
| FR | 2 926 660 A1 | 7/2009 |
| GB | 1 455 972 | 11/1976 |
| GB | 1 511 608 | 5/1978 |
| GB | 2 254 172 A | 9/1992 |
| GB | 2435838 A | 9/2007 |
| GB | 2 454 232 A | 5/2009 |
| JP | 2-224877 | 9/1990 |
| JP | 05-329645 | 12/1993 |
| JP | 07-047471 | 2/1995 |
| JP | 07-232270 | 9/1995 |
| JP | 08-505091 | 4/1996 |
| JP | 08-150476 | 6/1996 |
| JP | 08-132274 | 5/1998 |

(56) References Cited

FOREIGN PATENT DOCUMENTS

| | | |
|---|---|---|
| JP | 11104833 | 4/1999 |
| JP | 2000-167666 A | 6/2000 |
| JP | 2001-071140 A | 3/2001 |
| JP | 2002278670 A | 9/2002 |
| JP | 2003-200372 A | 7/2003 |
| JP | 2003-326362 A | 11/2003 |
| JP | 2006-006604 A | 1/2006 |
| JP | 2006-281270 A | 10/2006 |
| JP | 2007-290025 A | 11/2007 |
| JP | 2009-500178 A | 1/2009 |
| JP | 2009160636 A | 7/2009 |
| JP | 2012024867 A | 2/2012 |
| KR | 20090010693 | 1/2009 |
| RU | 2008 108 601 C1 | 11/2009 |
| SU | 1038963 A1 | 8/1983 |
| WO | 98/45078 | 10/1998 |
| WO | 0112376 A1 | 2/2001 |
| WO | 01/43910 | 6/2001 |
| WO | 0158400 A1 | 8/2001 |
| WO | 2005102230 A1 | 11/2005 |
| WO | 2006034571 A1 | 4/2006 |
| WO | 2007009131 | 1/2007 |
| WO | 2007039278 | 4/2007 |
| WO | 2009120921 | 1/2009 |
| WO | 2009060231 A1 | 5/2009 |
| WO | 2009149740 A1 | 12/2009 |
| WO | 2010000003 A2 | 1/2010 |
| WO | 2010020867 | 2/2010 |
| WO | 2010020870 | 2/2010 |
| WO | 2010044982 | 4/2010 |
| WO | 2010091493 A1 | 8/2010 |
| WO | 2011045654 A1 | 4/2011 |
| WO | 2011058433 | 5/2011 |
| WO | 2011058433 A1 | 5/2011 |
| WO | 2011067447 A1 | 6/2011 |
| WO | 2011097035 A2 | 8/2011 |
| WO | 2012082105 A1 | 6/2012 |
| WO | 2012143327 A1 | 10/2012 |
| WO | 2013014202 A1 | 1/2013 |
| WO | 2013061518 | 5/2013 |
| WO | 2013114189 A1 | 8/2013 |
| WO | 2013175079 A1 | 11/2013 |
| WO | 2014007830 A1 | 1/2014 |
| WO | 2014019045 A1 | 2/2014 |
| WO | 2014020386 | 2/2014 |

OTHER PUBLICATIONS

P. Tschirner et al., "Virtual and Augmented Reality for Quality Improvement of Manual Welds" National Institute of Standards and Technology, Jan. 2002, Publication 973, 24 pages.

Dorin Aiteanu et al., "Generation and Rendering of a Virtual Welding Seam in an Augmented Reality Training Environment" Proceedings of the Sixth IASTED International Conference, Aug. 2006, 8 pages.

Y. Wang et al., "Impingement of Filler Droplets and Weld Pool During Gas Metal Arc Welding Process" International Journal of Heat and Mass Transfer, Sep. 1999, 14 pages.

Larry Jeffus, "Welding Principles and Applications" Sixth Edition, 2008, 10 pages.

R.J. Renwick et al., "Experimental Investigation of GTA Weld Pool Oscillations" Welding Research—Supplement to the Welding Journal, Feb. 1983, 7 pages.

Matt Phar, GPU Gems 2 Programming Techniques for High-Performance Graphics and General-Purpose Computation 2005, 12 pages.

SIMFOR/CESOL, "RV-SOLD" Welding Simulator, Technical and Functional Features, 20 pages, estimated Jan. 2010.

Chuansong Wu: "Microcomputer-based welder training simulator", Computers in Industry, vol. 20, No. 3, Oct. 1992, 5 pages, pp. 321-325, XP000205597, Elsevier Science Publishers, Amsterdam, NL.

ViziTech USA, retrieved on Mar. 27, 2014 from http://vizitechusa.com/, 2 pages.

Guu and Rokhlin ,Technique for Simultaneous Real-Time Measurements of Weld Pool Surface Geometry and Arc Force, 10 pages, Dec. 1992.

William T. Reeves, "Particles Systems—A Technique for Modeling a Class of Fuzzy Objects", Computer Graphics 17:3 pp. 359-376, 1983, 17 pages.

S.B. Chen, L. Wu, Q. L. Wang and Y. C. Liu, Self-Learning Fuzzy Neural Networks and Computer Vision for Control of Pulsed GTAW, 9 pages, dated May 1997.

Patrick Rodjito, Position tracking and motion prediction using Fuzzy Logic, 81 pages, 2006, Colby College.

D'Huart, Deat, and Lium; Virtual Environment for Training, 6th International Conference, ITS 20002, 6 pages, Jun. 2002.

Konstantinos Nasios (Bsc), Improving Chemical Plant Safety Training Using Virtual Reality, Thesis submitted to the University of Nottingham for the Degree of Doctor of Philosophy, 313 pages, Dec. 2001.

ANSI/A WS D 10.11 MID 10. 11 :2007 Guide for Root Pass Welding of Pipe without Backing Edition: 3rd American Welding Society / Oct. 13, 2006/36 pages ISBN: 0871716445, 6 pages.

M. Jonsson, L. Karlsson, and L-E Lindgren, Simulation of Tack Welding Procedures in Butt Joint Welding of Plates Welding Research Supplement, Oct. 1985, 7 pages.

Isaac Brana Veiga, Simulation of a Work Cell in the IGRIP Program, dated 2006, 50 pages.

Balijepalli, A. and Kesavadas, Haptic Interfaces for Virtual Environment and Teleoperator Systems, Haptics 2003, 7-.,Department of Mechanical & Aerospace Engineering, State University of New York at Buffalo, NY.

Johannes Hirche, Alexander Ehlert, Stefan Guthe, Michael Doggett, Hardware Accelerated Per-Pixel Displacement Mapping, 8 pages.

Yao et al., 'Development of a Robot System for Pipe Welding'. 2010 International Conference on Measuring echnology and Mechatronics Automation. Retrieved from the Internet: http://ieeexplore.ieee.org/stamp/stamp.jsp?tp=&arnumber=5460347&tag=1; pp. 1109-1112, 4 pages.

Steve Mann, Raymond Chun Bing Lo, Kalin Ovtcharov, Shixiang Gu, David Dai, Calvin Ngan, Tao Ai, Realtime HDR (High Dynamic Range) Video for Eyetap Wearable Computers, FPGA-Based Seeing Aids, and Glasseyes (EYETAPS), 2012 25th IEEE Canadian Conference on Electrical and Computer Engineering (CCECE),pp. 1-6, 6 pages, Apr. 29, 2012.

Kyt Dotson, Augmented Reality Welding Helmet Prototypes How Awsome the Technology Can Get, Sep. 26, 2012, Retrieved from the Internet: URL:http://siliconangle.com/blog/2012/09/26/augmented-reality-welding-helmet-prototypes-how-awesome-the-technology-can-get/,1 p., retrieved on Sep. 26, 2014.

Terrence O'Brien, "Google's Project Glass gets some more details",Jun. 27, 2012, Retrieved from the Internet: http://www.engadget.com/2012/06/27/googles-project-glass-gets-some-more-details/, 1 page, retrieved on Sep. 26, 2014.

T. Borzecki, G. Bruce, YS. Han, et al., Specialist Committee V.3 Fabrication Technology Committee Mandate, Aug. 20-25, 2006, 49 pages, vol. 2, 16th International Ship and Offshore Structures Congress, Southampton, UK.

G. Wang, P.G. Huang, and Y.M. Zhang: "Numerical Analysis of Metal Transfer in Gas Metal Arc Welding": Departments of Mechanical Engineering; and Electrical and Computer Engineering, University of Kentucky, Lexington, KY 40506-0108, 10 pages, Dec. 10, 2001.

Echtler et al, "17 The Intelligent Welding Gun: Augmented Reality for Experimental Vehicle Construction," Virtual and Augmented Reality Applications in Manufacturing (2003) pp. 1-27.

Teeravarunyou et al, "Computer Based Welding Training System," International Journal of Industrial Engineering (2009) 16(2): 116-125.

Antonelli et al, "A Semi-Automated Welding Station Exploiting Human-Robot Interaction," Advanced Manufacturing Systems and Technology (2011) pp. 249-260.

Praxair Technology Inc, "The RealWeld Trainer System: Real Weld Training Under Real Conditions" Brochure (2013) 2 pages.

(56) References Cited

OTHER PUBLICATIONS

United States Provisional Patent Application for "System for Characterizing Manual Welding Operations on Pipe and Other Curved Structures," U.S. Appl. No. 62/055,724, filed Sep. 26, 2014, 35 pages.
Lincoln Global, Inc., "VRTEX 360: Virtual Reality Arc Welding Trainer" Brochure (2015) 4 pages.
Wuhan Onew Technology Co Ltd, "ONEW-360 Welding Training Simulator" http://en.onewtech.com/_d276479751.htm as accessed on Jul. 10, 2015, 12 pages.
The Lincoln Electric Company, "VRTEX Virtual Reality Arc Welding Trainer," http://www.lincolnelectric.com/en-us/equipment/training-equipment/Pages/vrtex.aspx as accessed on Jul. 10, 2015, 3 pages.
Miller Electric Mfg Co, "LiveArc: Welding Performance Management System" Owner's Manual, (Jul. 2014) 64 pages.
Miller Electric Mfg Co, "LiveArc Welding Performance Management System" Brochure, (Dec. 2014) 4 pages.
International Search Report for PCT/IB2009/00605.
Robert Schoder, "Design and Implementation of a Video Sensor for Closed Loop Control of Back Bead Weld Puddle Width," Massachusetts, Institute of Technology, Dept. of Mechanical Engineering, May 27, 1983, 64 pages.
Hills and Steele, Jr.; "Data Parallel Algorithms", Communications of the ACM, Dec. 1986, vol. 29, No. 12, p. 1170.
Nancy C. Porter, J. Allan Cote, Timothy D. Gifford, and Wim Lam, Virtual Reality Welder Training, 29 pages, dated Jul. 14, 2006.
J.Y. (Yosh) Mantinband, Hillel Goldenberg, Llan Kleinberger, Paul Kleinberger, Autosteroscopic, field-sequential display with full freedom of movement OR Let the display were the shutter-glasses, 3ality (Israel) Ltd., 8 pages, 2002.
ARS Electronica Linz GMBH, Fronius, 2 pages, May 18, 1997.
D.K. Aidun and S.A. Martin, "Penetration in Spot GTA Welds during Centrifugation," Journal of Material Engineering and Performance Volumn 7(5), 4 pages, Oct. 1998—597.
Arc+ simulator; httl://www.123arc.com/en/depliant_ang.pdf; 2 pages, 2000.
Glen Wade, "Human uses of ultrasound: ancient and modern", Ulrasonics vol. 38, 5 pages, dated 2000.
ASME Definitions, Consumables, Welding Positions, 4 pages, dated Mar. 19, 2001. See http://www.gowelding.com/asme4.htm.
M. Abbas, F. Waeckel, Code Aster (Software) EDF (France), 14 pages, Oct. 2001.
Achim Mahrle, Jurgen Schmidt, "The influence of fluid flow phenomena on the laser beam welding process"; International Journal of Heat and Fluid Flow 23, 10 pages, dated 2002.
The Lincoln Electric Company; CheckPoint Production Monitoring brochure; four (4) pages; http://www.lincolnelectric.com/assets/en_US/products/literature/s232.pdf; Publication S2.32; 4 pages, Issue Date Feb. 2012.
G. Wang, P.G. Huang, and Y.M. Zhang; "Numerical Analysis of Metal Transfer in Gas Metal Arc Welding," Departments of Mechanical and Electrical Engineering. University of Kentucky, 10 pages, Dec. 10, 2001.
Desroches, X.; Code-Aster, Note of use for aciculations of welding; Instruction manual U2.03 booklet: Thermomechincal; Document: U2.03.05; 13 pages, Oct. 1, 2003.
Fast, K. et al., "Virtual Training for Welding", Mixed and Augmented Reality, 2004, ISMAR 2004, Third IEEE and SM International Symposium on Arlington, VA, 2 pages, Nov. 2-5, 2004.
Cooperative Research Program, Virtual Reality Welder Training, Summary Report SR 0512, 4 pages, Jul. 2005.
Porter, et al., Virtual Reality Training, Paper No. 2005-P19, 14 pages, 2005.
Eduwelding+, Weld Into the Future; Online Welding Seminar—A virtual training environment; 123arc.com; 4 pages, 2005.
Miller Electric Mfg Co.; MIG Welding System features weld monitoring software; NewsRoom 2010 (Dialog® File 992); © 2011 Dialog. 2010; http://www.dialogweb.com/cgi/dwclient?reg=133233430487; three (3) pages; printed Mar. 8, 2012.

M. Abida and M. Siddique, Numerical simulation to study the effect of tack welds and root gap on welding deformations and residual stresses of a pipe-flange joint, Faculty of Mechanical Engineering, GIK Institute of Engineering Sciences and Technology, Topi, NWFP, Pakistan, 12 pages, Available on-line Aug. 25, 2005.
Abbas, M. et al. .; Code_Aster; Introduction to Code_Aster; User Manual; Booklet U1.0-: Introduction to Code_Aster; Document: U1.02.00; Version 7.4; 14 pages, Jul. 22, 2005.
Mavrikios D et al, A prototype virtual reality-based demonstrator for immersive and interactive simulation of welding processes, International Journal of Computer Integrated manufacturing, Taylor and Francis, Basingstoke, GB, vol. 19, No. 3, 8 pages, Apr. 1, 2006, pp. 294-300.
Nancy C. Porter, Edison Welding Institute; J. Allan Cote, General Dynamics Electric Boat; Timothy D. Gifford, VRSim; and Wim Lam, FCS Controls; Virtual Reality Welder Trainer, Sessiion 5: Joining Technologies for Naval Applications, 16 pages, earliest date Jul. 14, 2006 (http://weayback.archive.org).
T Borzecki, G. Bruce, Y.S. Han, M. Heinemann, A. Imakita, L. Josefson, W. Nie, D. Olson, F. Roland, and Y. Takeda, 16th International Shop and Offshore Structures Congress: Aug. 20-25, 2006: Southhampton, UK, 49 pages, vol. 2 Specialist Committee V.3 Fabrication Technology Committee Mandate.
Ratnam and Khalid: "Automatic classification of weld defects using simulated data and an MLP neutral network." Insight vol. 49, No. 3; 6 pages, Mar. 2007.
Wang et al., Study on welder training by means of haptic guidance and virtual reality for arc welding, 2006 IEEE International Conference on Robotics and Biomimetics, ROBIO 2006 ISBN-10: 1424405718, 5 pages, p. 954-958.
CS Wave, The Virtual Welding Trainer, 6 pages, 2007.
Asciencetutor.com, A division of Advanced Science and Automation Corp., VWL (Virtual Welding Lab), 2 pages, 2007.
Eric Linholm, John Nickolls, Stuart Oberman, and John Montrym, "NVIDIA Testla: A Unifired Graphics and Computing Architecture", IEEE Computer Society, 17 pages, 2008.
NSRP ASE, Low-Cost Virtual Realtiy Welder Training System, 1 page, 2008.
Edison Welding Institute, E-Weld Predictor, 3 pages, 2008.
CS Wave, A Virtual learning tool for welding motion, 10 pages, Mar. 14, 2008.
The Fabricator, Virtual Welding, 4 pages, Mar. 2008.
N. A. Tech., P/NA.3 Process Modeling and Optimization, 11 pages, Jun. 4, 2008.
FH Joanneum, Fronius—virtual welding, 2 pages, May 12, 2008.
Eduwelding+, Training Activities with arc+ simulator; Weld Into the Future, Online Welding Simulator—A virtual training environment; 123arc.com; 6 pages, May 2008.
ChemWeb.com, Journal of Materials Engineering and Performance (v.7, #5), 3 pgs., printed Sep. 26, 2012.
Choquet, Claude; "ARC+: Today's Virtual Reality Solution for Welders" Internet Page, 6 pages, Jan. 1, 2008.
Juan Vicenete Rosell Gonzales, "RV-Sold: simulator virtual para la formacion de soldadores"; Deformacion Metalica, Es. vol. 34, No. 301, 14 pages, Jan. 1, 2008.
White et al., Virtual welder training, 2009 IEEE Virtual Reality Conference, 1 page, p. 303, 2009.
Training in a virtual environment gives welding students a leg up, retrieved on Apr. 12, 2010 from: http://www.thefabricator.com/article/arcwelding/virtually-welding, 4 pages.
Sim Welder, retrieved on Apr. 12, 2010 from: http://www.simwelder.com, 2 pages.
P. Beatriz Garcia-Allende, Jesus Mirapeix, Olga M. Conde, Adolfo Cobo and Jose M. Lopez-Higuera; Defect Detection in Arc-Welding Processes by Means of the Line-to-Continuum Method and Feature Selection; www.mdpi.com/journal/sensors; 2009; 18 pages; Sensors 2009, 9, 7753-7770; doi; 10.3390/s91007753.
Production Monitoring 2 brochure, four (4) pages, The Lincoln Electric Company, May 2009.
International Search Report and Written Opinion from PCT/IB10/02913, 11 pages, dated Apr. 19, 2011.
Bjorn G. Agren; Sensor Integration for Robotic Arc Welding; 1995; vol. 5604C of Dissertations Abstracts International p. 1123; Dis-

(56) References Cited

OTHER PUBLICATIONS sertation Abs Online (Dialog® File 35): © 2012 ProQuest Info& Learning: http://dialogweb.com/cgi/dwclient?req=1331233317524; one (1) page; printed Mar. 8, 2012.
J. Hu and Hi Tsai, Heat and mass transfer in gas metal arc welding. Part 1: the arc, found in ScienceDirect, International Journal of Heat and Mass Transfer 50 (2007), 14 pages, 833-846 Available on Line on Oct. 24, 2006 http://www.web.mst.edu/~tsai/publications/HU-IJHMT-2007-1-60.pdf.
M. Ian Graham, Texture Mapping, Carnegie Mellon University Class 15-462 Computer Graphics, Lecture 10, 53 pages, dated Feb. 13, 2003.
U.S. Appl. No. 14/248,775, filed Apr. 9, 2014, System and Methods Providing Enhanced Education and Training in a Virtual Reality Environment.
U.S. Appl. No. 14/248,780, filed Apr. 9, 2014, System and Methods Providing Enhanced Education and Training in a Virtual Reality Environment.
U.S. Appl. No. 15/018,908, filed Feb. 9, 2016, System and Methods Providing Enhanced Education and Training in a Virtual Reality Environment.
U.S. Appl. No. 15/062,469, filed Mar. 7, 2016.
U.S. Appl. No. 15/064,283, filed Mar. 8, 2016.
U.S. Appl. 14/690,564, filed Apr. 20, 2015, Virtual Welding System.
U.S. Appl. No. 15/064,276, filed Mar. 8, 2016.
U.S. Appl. No. 14/821,004, filed Aug. 7, 2015, Importing and Analyzing External Data Using a Virtual Reality Welding System.
U.S. Appl. No. 14/821,018, filed Aug. 7, 2015, Importing and Analyzing External Data Using a Virtual Reality Welding System.
U.S. Appl. No. 14/821,051, filed Aug. 7, 2015, Importing and Analyzing External Data Using a Virtual Reality Welding System.
U.S. Appl. No. 15/017,561, filed Feb. 5, 2016, Importing and Analyzing External Data Using a Virtual Reality Welding System.
U.S. Appl. No. 15/017,564, filed Feb. 5, 2016, Importing and Analyzing External Data Using a Virtual Reality Welding System.
U.S. Appl. No. 15/017,569, filed Feb. 5, 2016, Importing and Analyzing External Data Using a Virtual Reality Welding System.
U.S. Appl. No. 14/074,971, filed Nov. 8, 2013, Virtual Testing and Inspection of a Virtual Weldment.
Petition for Inter Partes Review of U.S. Pat. No. 8,747,116; IPR 2016-00749; Apr. 7, 2016; 70 pages.
Petition for Inter Partes Review of U.S. Pat. No. Re. 45,398; IPR 201600840; Apr. 18, 2016; 71 pages.
Petition for Inter Partes Review of U.S. Pat. No. 9,293,056; IPR 2016-00904; May 9, 2016; 91 pages.
Petition for Inter Partes Review of U.S. Pat. No. 9,293,057; IPR 2016-00905; May 9, 2016; 87 pages.
Kobayashi, Ishigame, and Kato, "Skill Training System of Manual Arc Welding By Means of Face-Shield-Like HMD and Virtual Electrode" ("Kobayashi 2003"), Entertainment Computing, vol. 112 of the International Federation for Information Processing (IFIP), Springer Science + Business Media, New York, copyright 2003, pp. 389-396.
G.E. Moore, "No exponential is forever: but 'Forever' can be delayed!," IEEE International Solid-State Circuits Conference, 2003. 19 pages.
"High Performance Computer Architectures_A Historical Perspective," downloaded May 5, 2016. http://homepages.inf.ed.ac.uk/cgi/mi/comparch.pl?Paru/perf.html,Paru/perf-f.html,Paru/menu-76.html; 3 pages.
Andreas Grahn, "Interactive Simulation of Contrast Fluid using Smoothed Particle Hydrodynamics," Jan. 1, 2008, Master's Thesis in Computing Science, Umeå University, Department of Computing Science, Umeå, Sweden; 69 pages.
Marcus Vesterlund, "Simulation and Rendering of a Viscous Fluid using Smoothed Particle Hydrodynamics," Dec. 3, 2004, Master's Thesis in Computing Science, Umeå University, Department of Computing Science, Umeå, Sweden; 46 pages.

M. Müller, et al., "Point Based Animation of Elastic, Plastic and Melting Objects," Eurographics/ACM SIGGRAPH Symposium on Computer Animation (2004); 11 pages.
Andrew Nealen, "Point-Based Animation of Elastic, Plastic, and Melting Objects," CG topics, Feb. 2005; 2 pages.
D. Tonnesen, Modeling Liquids and Solids using Thermal Particles, Proceedings of Graphics Interface'91, pp. 255-262, Calgary, Alberta, 1991.
"CUDA Programming Guide Version 1.1," Nov. 29, 2007. 143 pages.
Webster's II new college dictionary, 3rd ed., Houghton Mifflin Co., copyright 2005, Boston, MA, p1271, definition of "wake." 3 pages.
Da Dalto L, et al. "CS Wave: Learning welding motion in a virtual environment" Published in Proceedings of the IIW International Conference, Jul. 10-11, 2008; 19 pages.
CS Wave-Manual, "Virtual Welding Workbench User Manual 3.0" 2007; 25 pages.
Choquet, Claude. "ARC+®: Today's Virtual Reality Solution for Welders", Published in Proceedings of the IIW Internatioal Conference; Jul. 10-11, 2008; 19 pages.
Welding Handbook, Welding Science & Technology, American Welding Society, Ninth Ed., Copyright 2001. Appendix A "Terms and Definitions" 54 pages.
Virtual Welding: A Low Cost Virtual Reality Welder Training System, NSRP RA 07-01—BRP Oral Review Meeting in Charleston, SC at ATI, Mar. 2008; 6 pages.
Dorin Aiteanu "Virtual and Augmented Reality Supervisor for A New Welding Helmet" Dissertation Nov. 15, 2005; 154 pages.
Screen Shot of CS Wave Exercise 135.FWPG Root Pass Level 1 https://web.archive.org/web/20081128081858/http://wave.c-s.fr/images/english/snap_evolution2.jpg; 1 page.
Screen Shot of CS Wave Control Centre V3.0.0 https://web.archive.org/web/20081128081915/http:/wave.c-s.fr/ Images/english/snap_evolution4.jpg; 1 page.
Screen Shot of CS Wave Control Centre V3.0.0 https://web.archive.org/web/20081128081817/http:/wave.c-s.fr/ Images/english/snap_evolution6.jpg; 1 page.
Da Dalto L, et al. "CS Wave A Virtual learning tool for the welding motion," Mar. 14, 2008; 10 pages.
Nordruch, Stefan, et al. "Visual Online Monitoring of PGMAW Without a Lighting Unit", Jan. 2005; 14 pages.
"The Evolution of Computer Graphics," Tony Tamasi, NVIDIA, 2008; 36 pages.
"VRSim Powering Virtual Reality, www.lincolnelectric.com/en-us/eguipment/lraining-equipmenl/Pages/powered-by'rsim.aspx, 2016, 1 page".
Hillers, B.; Graser, A. "Direct welding arc observation without harsh flicker," 8 pages, allegedly FABTECH International and AWS weldinq show, 2007.
Declaration of Dr. Michael Zyda, May 3, 2016, exhibit to IPR 2016-00905; 72 pages.
Declaration of Edward Bohnart, Apr. 27, 2016, exhibit to IPR 2016-00905; 23 pages.
Declaration of Dr. Michael Zyda, May 3, 2016, exhibit to IPR 2016-00904; 76 pages.
Declaration of Edward Bohnart, Apr. 27, 2016, exhibit to IPR 2016-00904; 22 pages.
Declaration of AxelGraeser, Apr. 17, 2016, exhibit to IPR 2016-00840; 88 pages.
Russel and Norvig, "Artificial Intelligence: A Modem Approach", Prentice-Hall (Copyright 1995).
Mechanisms and Mechanical Devices Source Book, Chironis, Neil Sclater; McGraw Hill; 2nd Addition, 1996.
ARC+ Welding Simulation presentation; 25 pages.
Bender Shipbuilding and Repair Co. Virtual Welding-A Low Cost Virtual Reality Welding Training System. Proposal submitted pursuant to MSRP Advanced Shipbuilding Enterprise Research Announcement, Jan. 23, 2008. 28 pages, See also, http://www.nsrp.org/6-Presentations/WD/020409 Virtual Welding Wilbur.pdf;.
Porter, Nancy; Cote, Allan; Gifford, Timothy; and Lam, Wim. "Virtual Reality Welder Training." The American Welding Society FABTECH International/ AWS Welding Show, Session 5. 29 pages; allegedly Chicago 2005.

(56) References Cited

OTHER PUBLICATIONS

Tschirner, Petra; Hillers, Bernd; and Graser, Axel "A Concept for the Application of Augmented Reality in Manual Gas Metal Arc Welding." Proceedings of the International Symposium on Mixed and Augmented Reality; 2 pages; 2002.
Penrod, Matt. "New Welder Training Tools." EWI PowerPoint presentation; 16 pages allegedly 2008.
Fite-Georgel, Pierre. "Is there a Reality in Industrial Augmented Reality?" 10th IEEE International Symposium on Mixed and Augmented Reality (ISMAR). 10 pages, allegedly 2011.
Aiteanu, Dorian; and Graser, Axel. "Generation and Rendering of a Virtual Welding Seam in an Augmented Reality Training Environment." Proceedings of the Sixth IASTED International Conference on Visualization, Imaging and Image Processing, Aug. 28-30, 2006, 8 pages, allegedly Palma de Mallorca, Spain. Ed. J.J. Villaneuva. ACTA Press.
Hillers, B.; Graser, A. "Real time Arc-Welding Video Observation System." 62nd International Conference of IIW, Jul. 12-17, 2009, 5 pages, allegedly Singapore 2009.
Advance Program of American Welding Society Programs and Events. Nov. 11-14, 2007. 31 pages. Chicago.
Terebes: examples from http://www.terebes.uni-bremen.de.; 6 pages.
Sandor, Christian; Gudrun Klinker. "PAARTI: Development of an Intelligent Welding Gun for BMW." PIA2003, 7 pages, Tokyo. 2003.
ARVIKA Forum Vorstellung Projekt PAARI. BMW Group Virtual Reality Center. 4 pages. Nuernberg. 2003.
Sandor, Christian; Klinker, Gudrun. "Lessons Learned in Designing Ubiquitous Augmented Reality User Interfaces." 21 pages, allegedly from Emerging Technologies of Augmented Reality: Interfaces Eds. Haller, M.; Billinghurst, M.; Thomas, B. Idea Group Inc. 2006.
Impact Welding: examples from current and archived website, trade shows, etc. See, e.g., http://www.impactwelding.com. 53 pages.
http://www.nsrp.org/6-Presentations/WDVirtual_Welder.pdf (Virtual Reality Welder Training, Project No. SI051, Navy ManTech Program, Project Review for ShipTech 2005); 22 pages Biloxi, MS.
https://app.aws.org/w/r/www/wj/2005/03/WJ_2005_03.pdf (AWS Welding Journal, Mar. 2005 (see, e.g., p. 54)).; 114 pages.
https://app.aws.org/conferences/defense/live index.html (AWS Welding in the Defense Industry conference schedule, 2004); 12 pages.
https://app.aws.org/wj/2004/04/052/njc (AWS Virtual Reality Program to Train Welders for Shipbuilding, workshop Information, 2004); 7 pages.
http://citeseerx.ist.psu .edu/viewdoc/download; jsessionid= E5 B275EI72A9E2 D E2803B9 A5BCA3 E8F8?doi=I 0.1.1.134.8879 &rep=repl&type=pdf (Virtual Reality Welder Training, Cooperative Research Program Summary report SR0512, Jul. 2005); 4 pages.
https://app.aws.org/wj/2007 /11WJ200711.pdf (AWS Welding Journal, Nov. 2007); 240 pages.
American Welding Society, "Vision for Welding Industry"; 41 pages.
Energetics, Inc. "Welding Technology Roadmap", Sep. 2000, 38 pages.
Aiteanu, Dorian; and Graser, Axel. "Computer-Aided Manual Welding Using an Augmented Reality Supervisor" Sheet Metal Welding Conference XII, Livonia, MI, May 9-12, 2006, 14 pages.
Hillers, Bernd; Aiteanu, Dorin and Graser, Axel "Augmented Reality—Helmet for the Manual Welding Process" Institute of Automation, University of Bremen, Germany; 21 pages.
Aiteanu, Dorin, Hillers, Bernd and Graser, Axel "A Step Forward in Manual Welding: Demonstration of Augmented Reality Helmet" Institute of Automation, University of Bremen, Germany, Proceedings of the Second IEEE and ACM International Symposium on Mixed and Augmented Reality; 2003; 2 pages.
ArcSentry Weld Quality Monitoring System; Native American Technologies, allegedly 2002, 5 pages.
P/NA.3 Process Modelling and Optimization; Native American Technologies, allegedly 2002, 5 pages.

B. Hillers, D. Aitenau, P. Tschirner, M. Park, A. Graser, B. Balazs, L Schmidt, "TEREBES: Welding Helmet with AR Capabilities", Institute of Automatic University Bremen; Institute of Industrial Engineering and Ergonomics, 10 pages, allegedly 2004.
"Sheet Metal Welding Conference XII", American Welding Society Detroit Section, May 2006, 11 pages.
Kenneth Fast, Timothy Gifford, Robert Yancey, "Virtual Training for Welding", Proceedings of the Third IEEE and ACM International Symposium on Mixed and Augmented Reality (ISMAR 2004); 2 pages.
Amended Answer to Complaint with Exhibit A for Patent Infringement filed by Seabery North America Inc. in *Lincoln Electric Co. et al.* v. *Seabery Soluciones, S.L. et al.*, Case No. 1:15-cv-01575-DCN, docket No. 44, filed Mar. 1, 2016, in the U.S. District Court for the Northern District of Ohio; 19 pages.
Amended Answer to Complaint with Exhibit A for Patent Infringement filed by Seabery Soluciones SL in *Lincoln Electric Co. et al.* v. *Seabery Soluciones, S.L. et al.*, Case No. 1:15-cv-01575-DCN, docket No. 45, filed Mar. 1, 2016, in the U.S. District Court for the Northern District of Ohio; 19 pages.
Reply to Amended Answer to Complaint for Patent Infringement filed by Lincoln Electric Company; Lincoln Global, Inc. in *Lincoln Electric Co. et al.* v. *Seabery Soluciones, S.L. et al.*, Case No. 1:15-cv-01575-DCN; docket No. 46, filed Mar. 22, 2016; 5 pages.
Answer for Patent Infringement filed by Lincoln Electric Company, Lincoln Global, Inc. in *Lincoln Electric Co. et al.* v. *Seabery Soluciones, S.L. et al.*, Case No. 1:15-cv-01575-DCN; docket No. 47, filed Mar. 22, 2016; 5 pages.
Petition for Inter Partes Review of U.S. Patent No. Re. 45,398; IPR 2016-00840; Apr. 18, 2016; 71 pages.
http://www.vrsim.net/history, downloaded Feb. 26, 2016 10:04:37 pm.
Complaint for Patent Infringement in *Lincoln Electric Co. et al.* v. *Seabery Soluciones, S.L. et al.*, Case No. 1:15-cv-01575-DCN, docket No. 1, filed Aug. 10, 2015, in the U.S. District Court for the Northern District of Ohio; 81 pages.
Kobayashi, Ishigame, and Kato, "Simulator of Manual Metal Arc Welding with Haptic Display" ("Kobayashi 2001"), Proc. of the 11th International Conf. on Artificial Reality and Telexistence (ICAT), Dec. 5-7, 2001, pp. 175-178, Tokyo, Japan.
Wahi, Maxwell, and Reaugh, "Finite-Difference Simulation of a Multi-Pass Pipe Weld" ("Wahi"), vol. L, paper 3/1, International Conference on Structural Mechanics in Reactor Technology, San Francisco, CA, Aug. 15-19, 1977.
Declaration of Dr. Michael Zyda, May 3, 2016, exhibit to IPR 2016-00749.
Declaration of Edward Bohnart, Apr. 27, 2016, exhibit to IPR 2016-00749.
Swantec corporate web page downloaded Apr. 19, 2016. http://www.swantec.com/technology/numerical-simulation/.
Catalina, Stefanescu, Sen, and Kaukler, "Interaction Of Porosity with a Planar Solid/Liquid Interface" ("Catalina"), Metallurgical and Materials Transactions, vol. 35A, May 2004, pp. 1525-1538.
Choquet, Claude. "ARC+®: Today's Virtual Reality Solution for Welders", Internet page; Jan. 1, 2008; 6 pages.
Fletcher Yoder Opinion re U.S. Pat. No. Re. 45,398 and U.S. Appl. No. 14/589,317; including appendices; Sep. 9, 2015; 1700 pages.
Aidun, Daryush "Influence of Simulated High-g On the Weld Size of Al—Li Alloy" Elevator Sciece Ltd.; 2001; 4 pages.
Porter, et al., Virtual Reality Training, vol. 22, No. 3, Aug. 2006; 13 pages.
International Search Report for PCT/IB2014/001796, dated Mar. 24, 3016; 8 pages.
International Search Report for PCT/IB2015/000161, dated Aug. 25, 2016; 9 pages.
International Search Report for PCT/IB2015/000777, dated Dec. 15, 2016; 11 pages.
International Search Report for PCT/IB2015/000814 dated Dec. 15, 2016; 9 pages.
Petition for Inter Partes Review of U.S. Pat. No. 8,747,116; IPR 2016-01568; Aug. 9, 2016; 75 pages.
Trial Denied IPR Proceeding of U.S. Pat. No. 8,747,116; IPR 2016-00749; Sep. 21, 2016; 21 pages.

(56) References Cited

OTHER PUBLICATIONS

Decision Trial Denied IPR Proceeding of U.S. Pat. No. 9,293,056; IPR 2016-00904; Nov. 3, 2016; 15 pages.
Decision Trial Denied IPR Proceeding of U.S. Pat. No. 9,293,057; IPR 2016-00905; Nov. 3, 2016; 21 pages.
Decision Termination Proceeding of U.S. Pat. No. 8,747,116; IPR 2016-01568; Nov. 15, 2016; 4 pages.
Decision Denying Request for Rehearing of U.S. Pat. No. Re. 45,398; IPR 2016-00840; Nov. 17, 2016; 10 pages.
Fletcher Yoder Opinion U.S. Pat. Re. 45,398 and U.S. Appl. No. 14/589,317, including Appendices; Sep. 9, 2015; 1700 pages.
Office Action from U.S. Appl. No. 14/526,914 dated Feb. 3, 2017.
International Preliminary Report from PCT/IB2015/001084 dated Jan. 26, 2017.
Exhibit B from Declaration of Morgan Lincoln in *Lincoln Electric Co. et al. v. Seabery Soluciones, S.L. et al.*, Case No. 1:15-cv-01575-DCN, dated Dec. 20, 2016, 5 pages.
Bryan E. Feldman, James F. O'Brien, Bryan M. Klingner, and Tolga G. Goktekin. Fluids in deforming meshes. In ACM SIGGRAPH/Eurographics Symposium on Computer Animation 2005, Jul. 2005.
Sun Yaoming; Application of Micro Computer in Robotic Technologies; Science and Technology Literature Press; Catalogue of New Books of Science and Technology; Sep. 1987, pp. 145-150.
Kenneth Fast; Virtual Welding—A Low Cost Virtual Reality Welder system training system phase II; NSRP ASE Technology Investment Agreement; Feb. 29, 2012; pp. 1-54.
Adam W. Bargteil, Tolga G. Goktekin, James F. O'Brien, and John A. Strain. A semi-lagrangian contouring method for fluid simulation. ACM Transactions on Graphics, 25(1), 2006.
Adam W. Bargteil, Funshing Sin, Jonathan E. Michaels, Tolga G. Goktekin, and James F. O'Brien. A texture synthesis method for liquid animations. In Proceedings of the ACM SIGGRAPH/Eurographics Symposium on Computer Animation, Sep. 2006.
Bryan M. Klingner, Bryan E. Feldman, Nuttapong Chentanez, and James F. O'Brien. Fluid animation with dynamic meshes. In Proceedings of ACM SIGGRAPH 2006, pp. 820-825, Aug. 2006.
Nuttapong Chentanez, Tolga G. Goktekin, Bryan E. Feldman, and James F. O'Brien. Simultaneous coupling of fluids and deformable bodies. In ACM SIGGRAPH/Eurographics Symposium on Computer Animation, pp. 83-89, Aug. 2006.
Nuttapong Chentanez, Bryan E. Feldman, Franc,ois Labelle, James F. O'Brien, and Jonathan R. Shewchuk. Liquid simulation on lattice-based tetrahedral meshes. In ACM SIGGRAPH/Eurographics Symposium on Computer Animation 2007, pp. 219-228, Aug. 2007.
Kass, M., and Miller, G., "Rapid, Stable Fluid Dynamics for Computer Graphics," Proceedings of SIGGRAPH '90, in Computer Graphics, vol. 24, No. 4, pp. 49-57, 1990.
James F. O'Brien and Jessica K. Hodgins. "Dynamic Simulation of Splashing Fluids". In Proceedings of Computer Animation 95, pp. 198-205, Apr. 1995.
Nathan Holmberg and Burkhard C. Wünsche. 2004. Efficient modeling and rendering of turbulent water over natural terrain. In Proceedings of the 2nd international conference on Computer graphics and interactive techniques in Australasia and South East Asia (Graphite '04).
Nils Thurey, Matthias Miller-Fischer, Simon Schirm, and Markus Gross. 2007. Real-time BreakingWaves for Shallow Water Simulations. In Proceedings of the 15th Pacific Conference on Computer Graphics and Applications (PG '07).
Jos Stam, Stable fluids, Proceedings of the 26th annual conference on Computer graphics and interactive techniques, p. 121-128, Jul. 1999.
Nick Foster, Ronald Fedkiw, Practical animation of liquids, Proceedings of the 28th annual conference on Computer graphics and interactive techniques, p. 23-30, Aug. 2001.
Nick Foster, Dimitri Metaxas, Realistic animation of liquids, Graphical Models and Image Processing, v.58 n.5, p. 471-483, Sep. 1996.
N. Rasmussen, D. Enright, D. Nguyen, S. Marino, N. Sumner, W. Geiger, S. Hoon, R. Fedkiw, Directable photorealistic liquids, Proceedings of the 2004 ACM SIGGRAPH/Eurographics symposium on Computer animation, Aug. 27-29, 2004, Grenoble, France.
Bryan E. Feldman, James F. O'Brien, and Okan Arikan. "Animating Suspended Particle Explosions". In Proceedings of ACM SIGGRAPH 2003, pp. 708-715, Aug. 2003.
Tolga G. Goktekin, Adam W. Bargteil, and James F. O'Brien. "A Method for Animating Viscoelastic Fluids". ACM Transactions on Graphics (Proc. of ACM SIGGRAPH 2004), 23(3):463-468, 2004.
Geoffrey Irving, Eran Guendelman, Frank Losasso, Ronald Fedkiw, Efficient simulation of large bodies of water by coupling two and three dimensional techniques, ACM SIGGRAPH 2006 Papers, Jul. 30-Aug. 3, 2006, Boston, Massachusetts.
Bart Adams, Mark Pauly, Richard Keiser, Leonidas J. Guibas, Adaptively sampled particle fluids, ACM SIGGRAPH 2007 papers, Aug. 5-9, 2007, San Diego, California.
Matthias Müller, David Charypar, Markus Gross, Particle-based fluid simulation for interactive applications, Proceedings of the 2003 ACM SIGGRAPH/Eurographics symposium on Computer animation, Jul. 26-27, 2003, San Diego, California.
Premoze, S., Tasdizen, T., Bigler, J., Lefohn, A. E., and Whitaker, R. T. 2003. Particle-based simulation of fluids. Comput. Graph. Forum 22, 3, 401-410.
Pascal Clausen, Martin Wicke, Jonathan R. Shewchuk, and James F. O'Brien. Simulating liquids and solid-liquid interactions with lagrangian meshes. ACM Transactions on Graphics, 32(2):17:1-15, Apr. 2013. Presented at SIGGRAPH 2013.

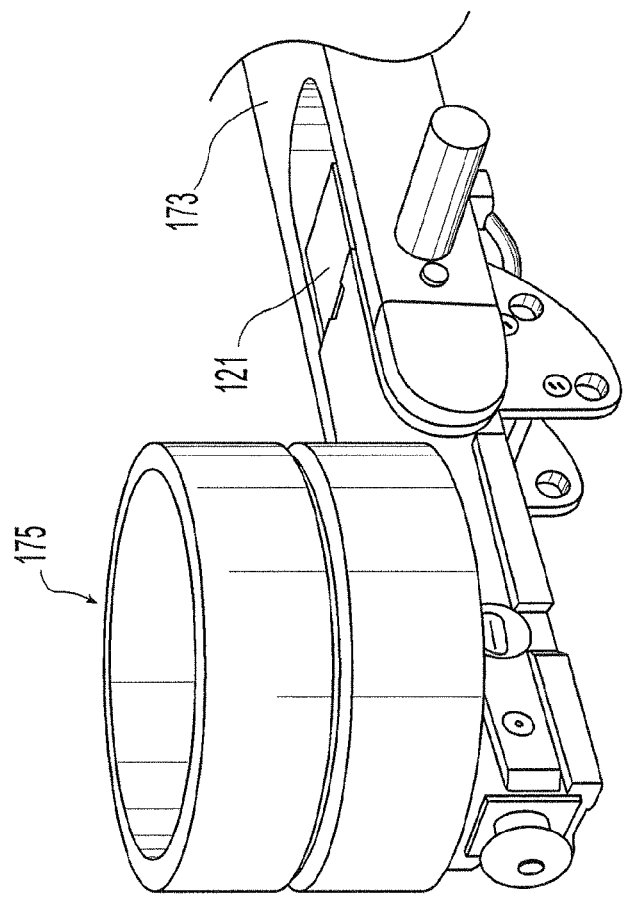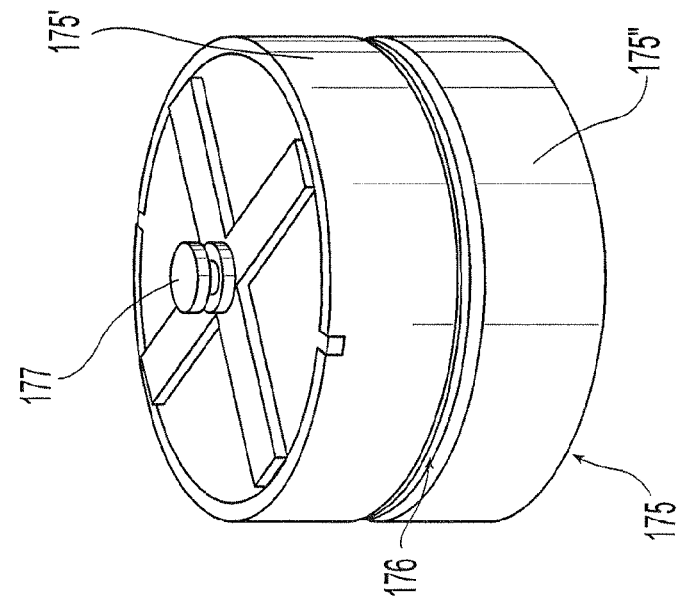

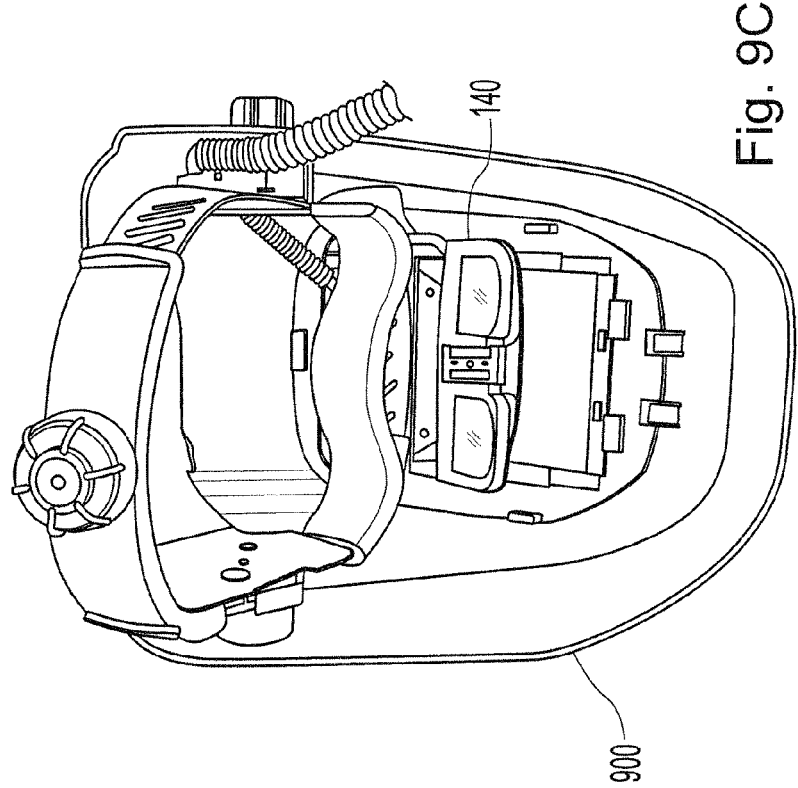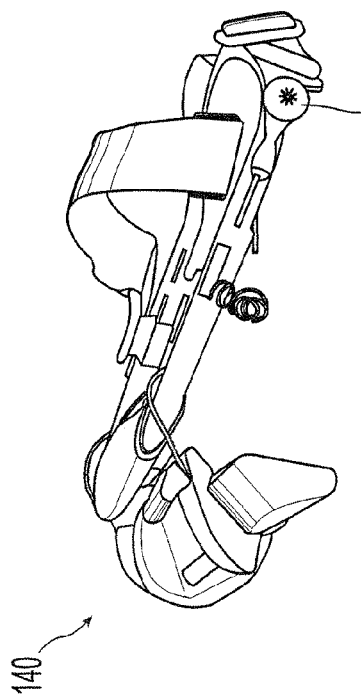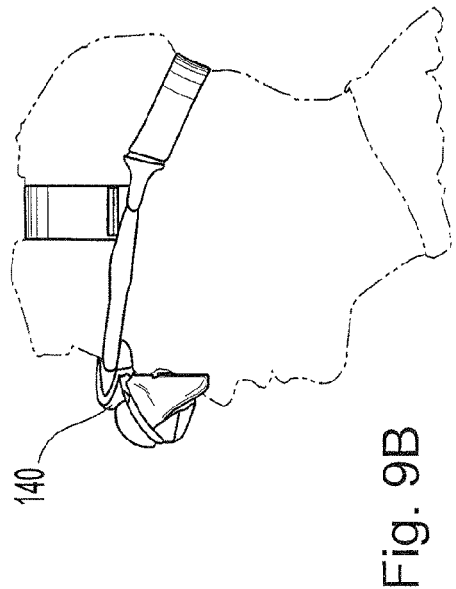

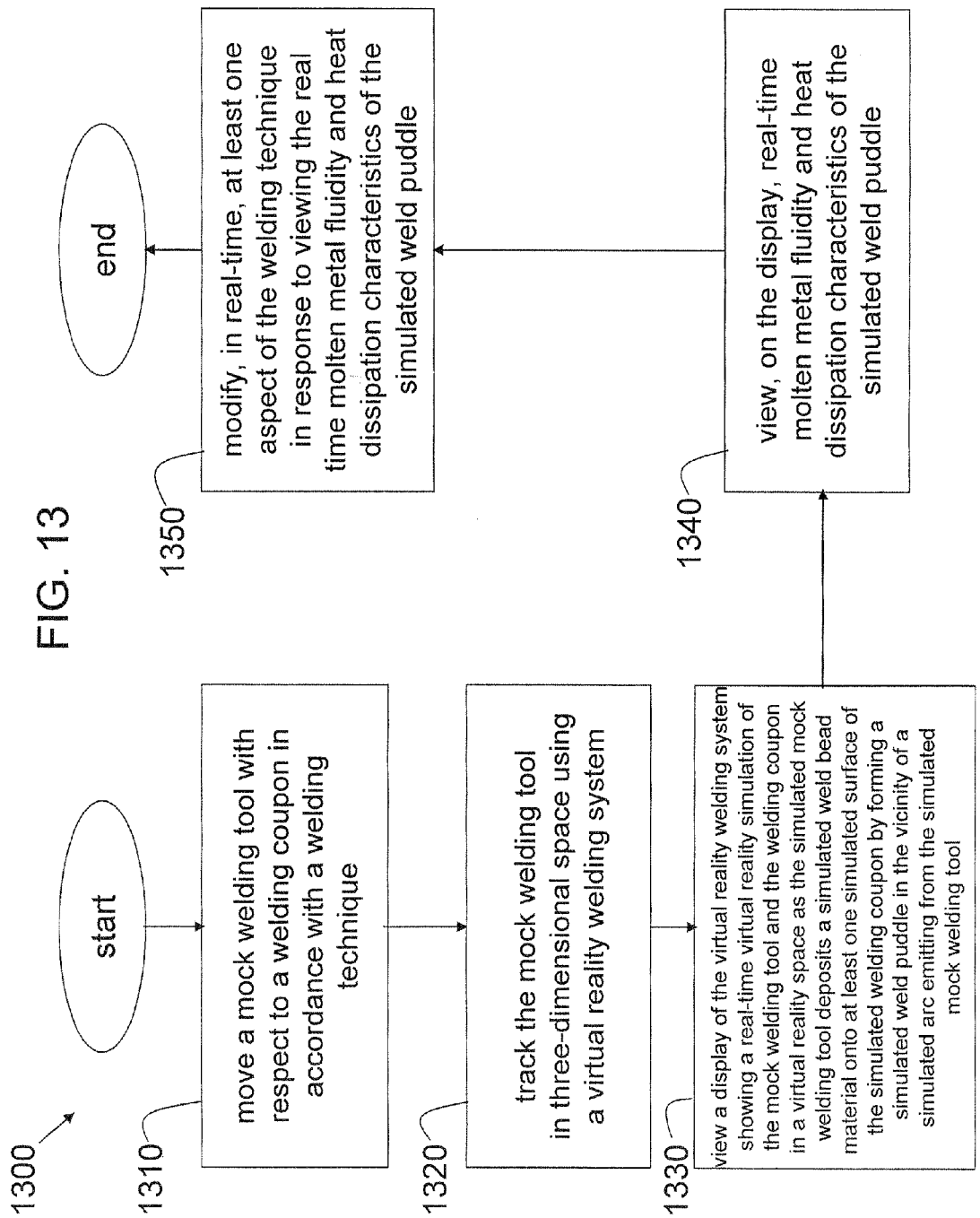

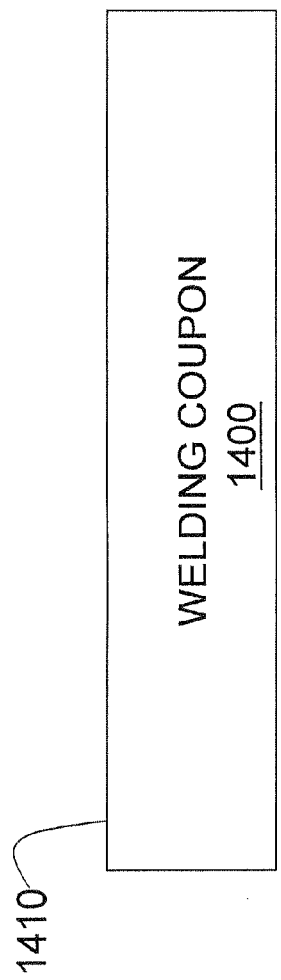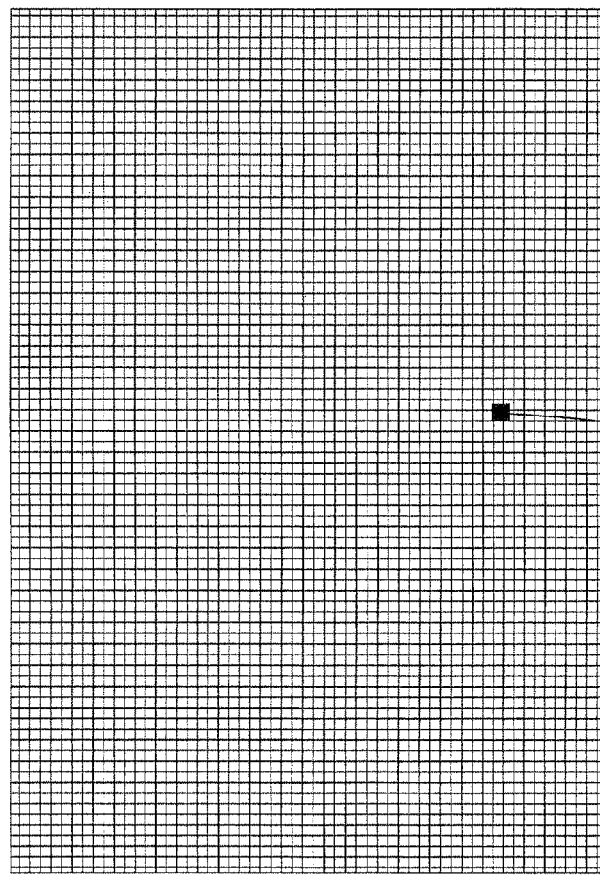

Width = |X-O|
Height = |Y-O| + |Z-O|
O' = Z + Y - O
X' = O' + X - O
Displacement is towards the line
$\overline{X' - O'}$ FIG. 17
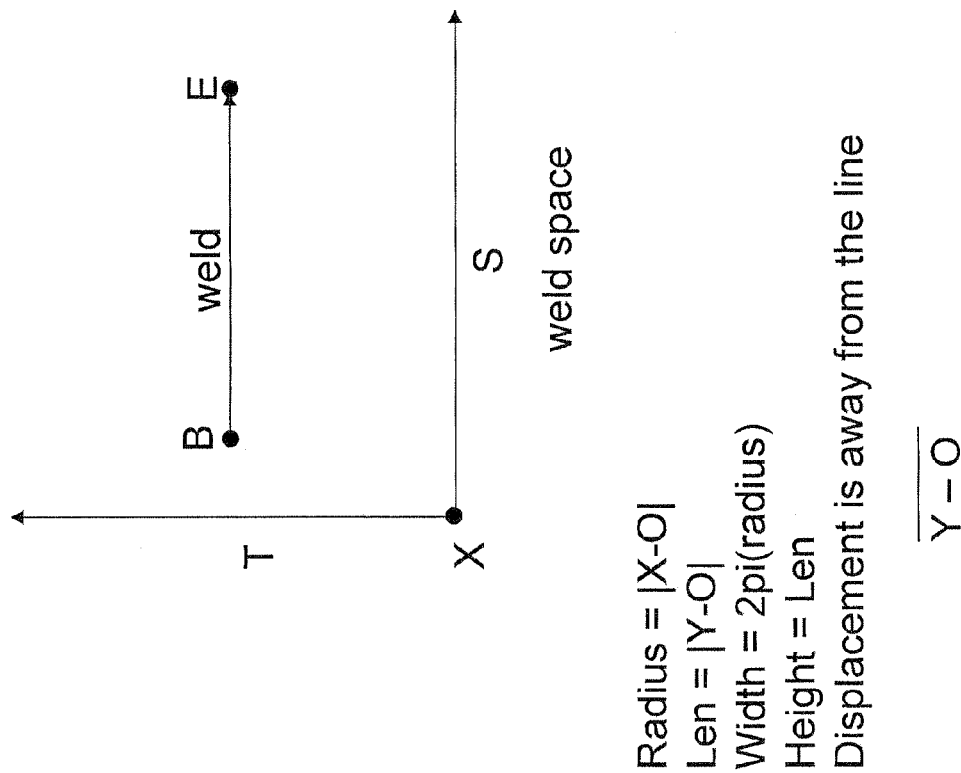
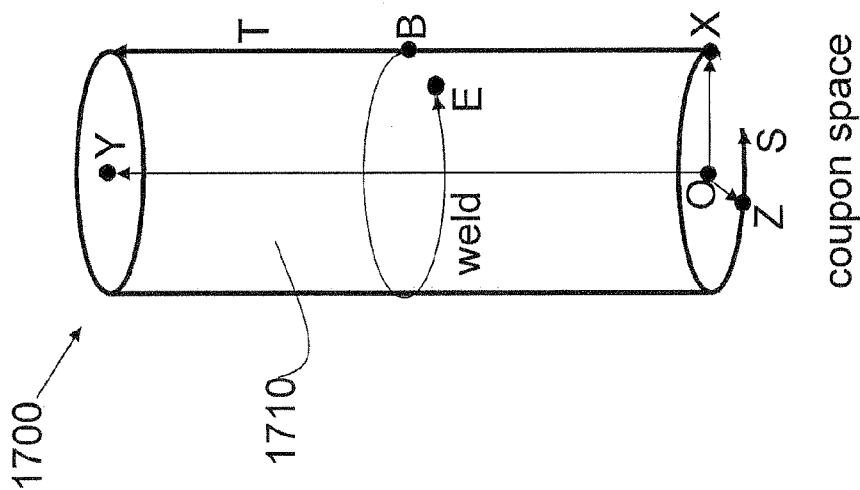

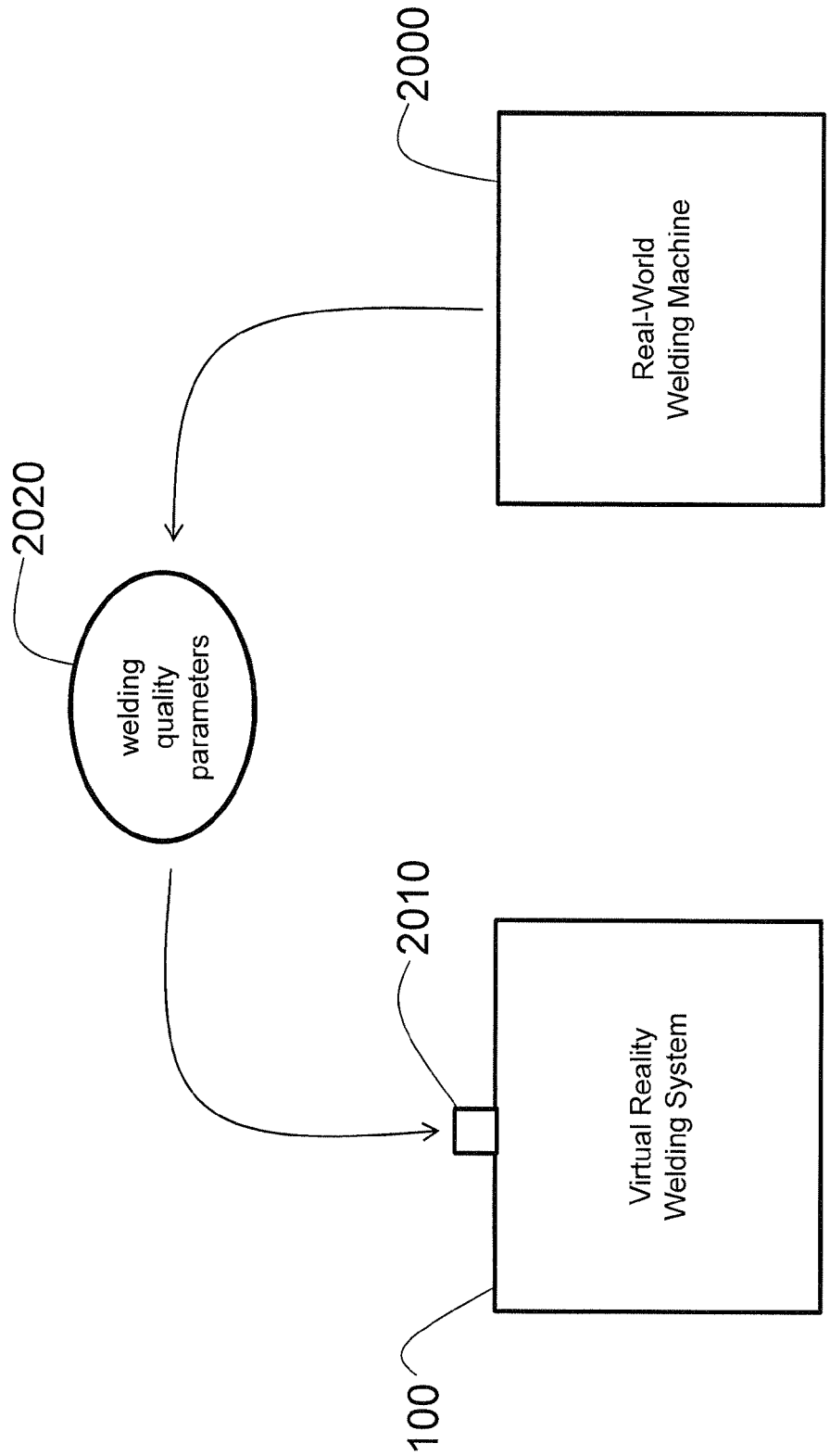

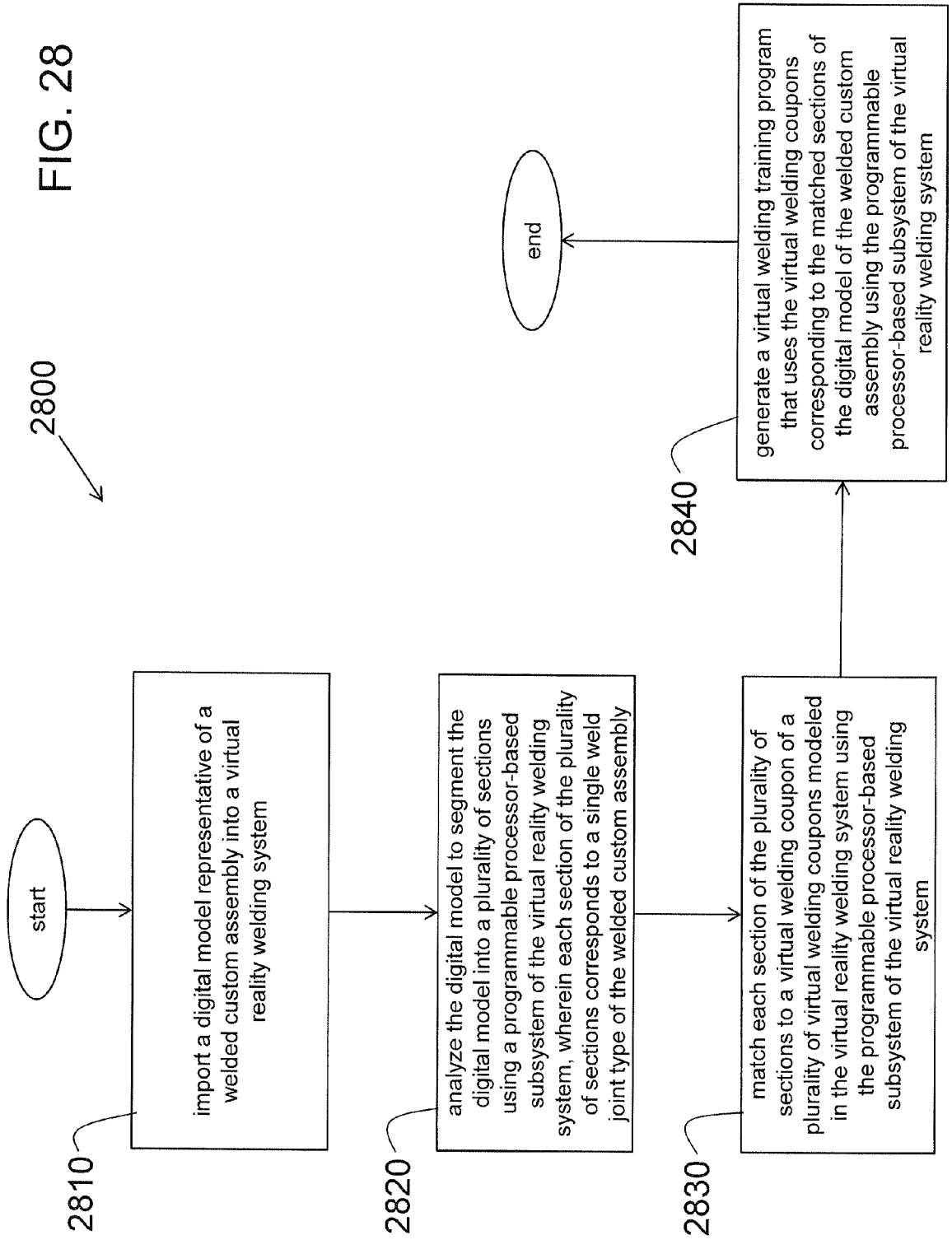

IMPORTING AND ANALYZING EXTERNAL DATA USING A VIRTUAL REALITY WELDING SYSTEM

CROSS-REFERENCE TO RELATED APPLICATIONS/INCORPORATION BY REFERENCE

This U.S. patent application claims priority to and is a continuation (CON) of pending U.S. application Ser. No. 13/792,309, filed on Mar. 11, 2013, which is a continuation-in-part (CIP) patent application of U.S. patent application Ser. No. 12/501,257 (now U.S. Pat. No. 8,747,116) filed on Jul. 10, 2009 which is incorporated herein by reference in its entirety and which claims priority to and the benefit of U.S. Provisional Patent Application Ser. No. 61/090,794 filed on Aug. 21, 2008. The Published U.S. patent application Ser. No. 13/453,124 and filed on Apr. 23, 2012 is incorporated herein by reference in its entirety.

TECHNICAL FIELD

Certain embodiments relate to virtual reality simulation. More particularly, certain embodiments relate to systems and methods for providing arc welding training in a simulated virtual reality environment or augmented reality environment using real-time weld puddle feedback, and for providing the importing and analyzing of external data in a virtual reality welding system.

BACKGROUND

Learning how to arc weld traditionally takes many hours of instruction, training, and practice. There are many different types of arc welding and arc welding processes that can be learned. Typically, welding is learned by a student using a real welding system and performing welding operations on real metal pieces. Such real-world training can tie up scarce welding resources and use up limited welding materials. Recently, however, the idea of training using welding simulations has become more popular. Some welding simulations are implemented via personal computers and/or on-line via the Internet. However, current known welding simulations tend to be limited in their training focus. For example, some welding simulations focus on training only for "muscle memory", which simply trains a welding student how to hold and position a welding tool. Other welding simulations focus on showing visual and audio effects of the welding process, but only in a limited and often unrealistic manner which does not provide the student with the desired feedback that is highly representative of real world welding. It is this actual feedback that directs the student to make necessary adjustments to make a good weld. Welding is learned by watching the arc and/or puddle, not by muscle memory.

Further limitations and disadvantages of conventional, traditional, and proposed approaches will become apparent to one of skill in the art, through comparison of such approaches with embodiments of the present invention as set forth in the remainder of the present application with reference to the drawings.

SUMMARY

An arc welding simulation has been devised on a virtual reality welding system that provides simulation of a weld puddle in a virtual reality space having real-time molten metal fluidity characteristics and heat absorption and heat dissipation characteristics. Data may be imported into the virtual reality welding system and analyzed to characterize a student welder's progress and to provide training.

In accordance with an embodiment, a virtual reality welding system includes a programmable processor-based subsystem, a spatial tracker operatively connected to the programmable processor-based subsystem, at least one mock welding tool capable of being spatially tracked by the spatial tracker, and at least one display device operatively connected to the programmable processor-based subsystem. The system is capable of simulating, in virtual reality space, a weld puddle having real-time molten metal fluidity and heat dissipation characteristics. The system is further capable of displaying the simulated weld puddle on the display device to depict a real-world weld. Based upon the student performance, the system will display an evaluated weld that will either be acceptable or show a weld with defects. External data may be imported to the virtual reality welding system and analyzed to determine the quality of a weld generated by a student welder, or to model sections of a welded custom assembly for training.

One embodiment provides a method. The method includes importing a first data set of welding quality parameters, being representative of a quality of a weld generated by a student welder during a real-world welding activity corresponding to a defined welding process, into a virtual reality welding system. The method also includes comparing a second data set of welding quality parameters stored on the virtual reality simulator, being representative of a quality of a virtual weld generated by the student welder during a simulated welding activity corresponding to the defined welding process on the virtual reality welding system, to the first data set using a programmable processor-based subsystem of the virtual reality welding system. The method further includes generating a numerical comparison score in response to the comparing using the programmable processor-based subsystem of the virtual reality welding system.

One embodiment provides a method. The method includes importing a first data set of measured welding parameters, generated during a real-world welding activity corresponding to a defined welding process performed by an expert welder using a real-world welding machine, into a virtual reality welding system. The method also includes storing a second data set of simulated welding parameters, generated during a simulated welding activity corresponding to the defined welding process as performed by a student welder using the virtual reality welding system, on the virtual reality welding system. The method further includes calculating a plurality of student welding quality parameters by comparing the first data set to the second data set using a programmable processor-based subsystem of the virtual reality welding system.

One embodiment provides a method. The method includes storing a first data set of simulated welding parameters, generated during a first simulated welding activity corresponding to a defined welding process performed by an expert welder using a virtual reality welding system, on the virtual reality welding system. The method also includes storing a second data set of simulated welding parameters, generated during a second simulated welding activity corresponding to the defined welding process as performed by a student welder using the virtual reality welding system, on the virtual reality welding system. The method further includes calculating a plurality of student welding quality parameters by comparing the first data set to the second data set using a programmable processor-based subsystem of the virtual reality welding system.

One embodiment provides a method. The method includes importing a digital model representative of a welded custom assembly into a virtual reality welding system. The method also includes analyzing the digital model to segment the digital model into a plurality of sections using a programmable processor-based subsystem of the virtual reality welding system, wherein each section of the plurality of sections corresponds to a single weld joint type of the welded custom assembly. The method further includes matching each section of the plurality of sections to a virtual welding coupon of a plurality of virtual welding coupons modeled in the virtual reality welding system using the programmable processor-based subsystem of the virtual reality welding system.

These and other features of the claimed invention, as well as details of illustrated embodiments thereof, will be more fully understood from the following description and drawings.

BRIEF DESCRIPTION OF THE DRAWINGS

FIG. 7A illustrates an example embodiment of a pipe welding coupon (WC) of the system of FIG. 1;

FIG. 7B illustrates the pipe WC of FIG. 7A mounted in an arm of the table/stand (TS) of FIG. 6;

FIG. 9A illustrates an example embodiment of a face-mounted display device (FMDD) of the system of FIG. 1;

FIG. 9B is an illustration of how the FMDD of FIG. 9A is secured on the head of a user;

FIG. 9C illustrates an example embodiment of the FMDD of FIG. 9A mounted within a welding helmet;

FIG. 13 is a flow chart of an embodiment of a method of training using the virtual reality training system of FIG. 1;

FIGS. 14A-14B illustrate the concept of a welding pixel (wexel) displacement map, in accordance with an embodiment of the present invention;

FIG. 17 illustrates an example embodiment of a coupon space and a weld space of a pipe welding coupon (WC) simulated in the system of FIG. 1;

FIG. 20 illustrates the concept of importing welding quality parameters into a virtual reality welding system from a real-world welding machine;

FIG. 28 is a flowchart of an embodiment of a method to generate a virtual welding training program for a welded custom part.

DETAILED DESCRIPTION

An embodiment of the present invention comprises a virtual reality arc welding (VRAW) system comprising a programmable processor-based subsystem, a spatial tracker operatively connected to the programmable processor-based subsystem, at least one mock welding tool capable of being spatially tracked by the spatial tracker, and at least one display device operatively connected to the programmable processor-based subsystem. The system is capable of simulating, in a virtual reality space, a weld puddle having real-time molten metal fluidity and heat dissipation characteristics. The system is also capable of displaying the simulated weld puddle on the display device in real-time. The real-time molten metal fluidity and heat dissipation characteristics of the simulated weld puddle provide real-time visual feedback to a user of the mock welding tool when displayed, allowing the user to adjust or maintain a welding technique in real-time in response to the real-time visual feedback (i.e., helps the user learn to weld correctly). The displayed weld puddle is representative of a weld puddle that would be formed in the real-world based on the user's welding technique and the selected welding process and parameters. By viewing a puddle (e.g., shape, color, slag, size, stacked dimes), a user can modify his technique to make a good weld and determine the type of welding being done. The shape of the puddle is responsive to the movement of the gun or stick. As used herein, the term "real-time" means perceiving and experiencing in time in a simulated environment in the same way that a user would perceive and experience in a real-world welding scenario.

Furthermore, the weld puddle is responsive to the effects of the physical environment including gravity, allowing a user to realistically practice welding in various positions including overhead welding and various pipe welding angles (e.g., 1G, 2G, 5G, 6G). As used herein, the term "virtual weldment" refers to a simulated welded part that exists in virtual reality space. For example, a simulated welding coupon that has been virtually welded as described herein is an example of a virtual weldment.

Figure 1:
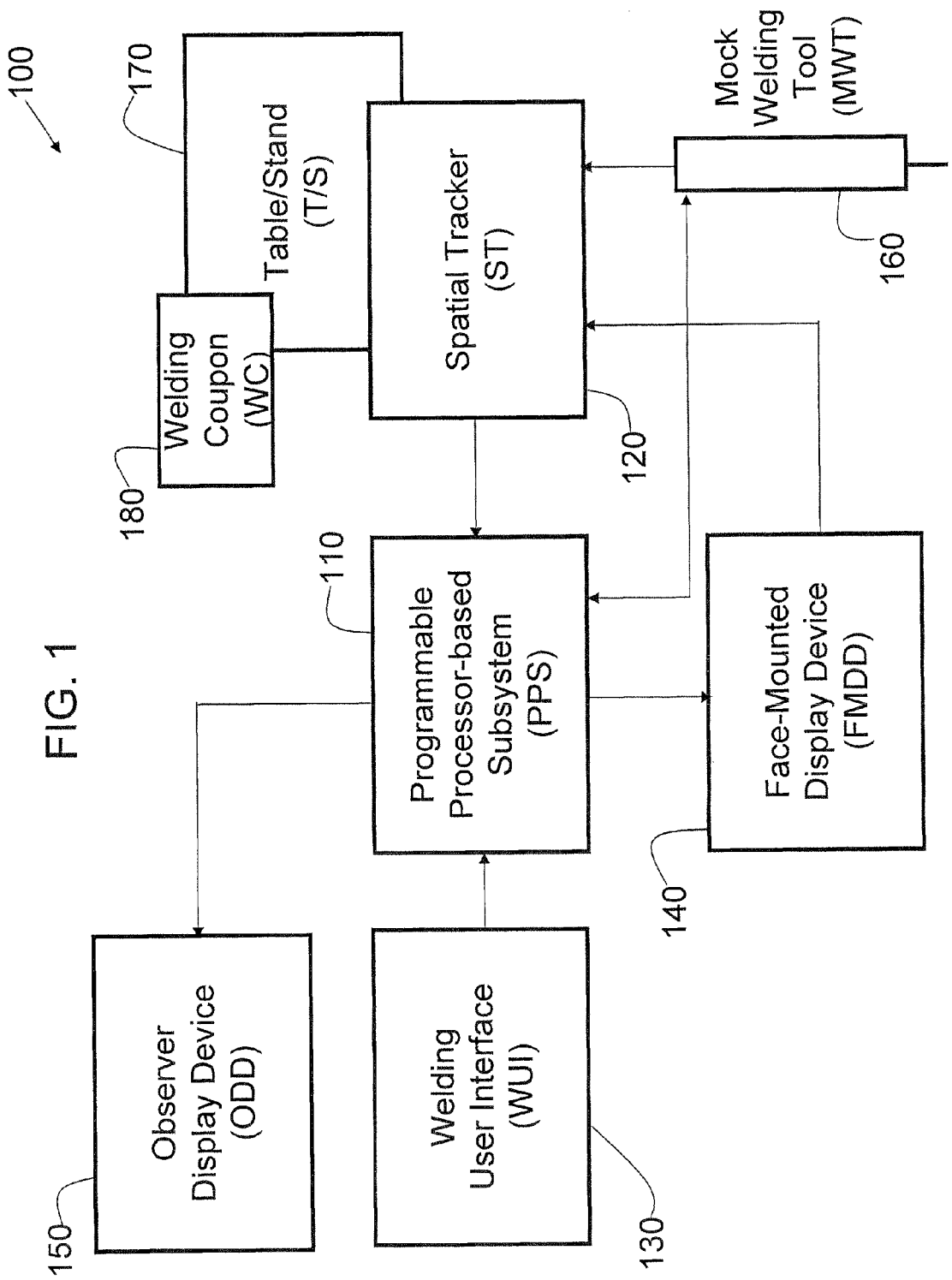
FIG. 1 illustrates a first example embodiment of a system block diagram of a system providing arc welding training in a real-time virtual reality environment.

FIG. 1 illustrates an example embodiment of a system block diagram of a system 100 providing arc welding training in a real-time virtual reality environment. The system 100 includes a programmable processor-based subsystem (PPS) 110. The system 100 further includes a spatial tracker (ST) 120 operatively connected to the PPS 110. The system 100 also includes a physical welding user interface (WUI) 130 operatively connected to the PPS 110 and a face-mounted display device (FMDD) 140 operatively connected to the PPS 110 and the ST 120. The system 100 further includes an observer display device (ODD) 150 operatively connected to the PPS 110. The system 100 also includes at least one mock welding tool (MWT) 160 operatively connected to the ST 120 and the PPS 110. The system 100 further includes a table/stand (T/S) 170 and at least one welding coupon (WC) 180 capable of being attached to the T/S 170. In accordance with an alternative embodiment of the present invention, a mock gas bottle is provided (not shown) simulating a source of shielding gas and having an adjustable flow regulator.

Figure 2:
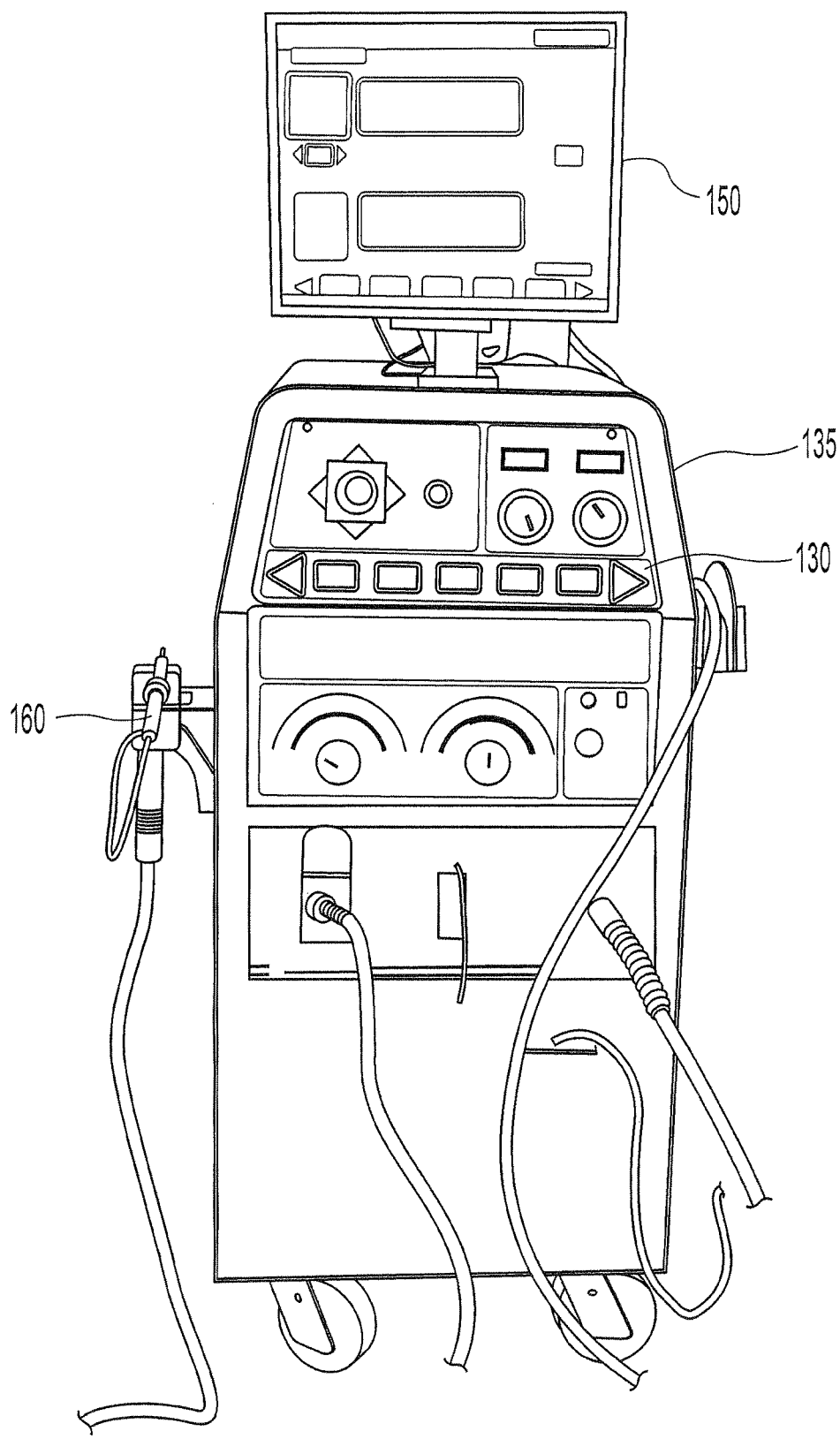
FIG. 2 illustrates an example embodiment of a combined simulated welding console and observer display device (ODD) of the system of FIG. 1.

FIG. 2 illustrates an example embodiment of a combined simulated welding console 135 (simulating a welding power source user interface) and observer display device (ODD) 150 of the system 100 of FIG. 1. The physical WUI 130 resides on a front portion of the console 135 and provides knobs, buttons, and a joystick for user selection of various modes and functions. The ODD 150 is attached to a top portion of the console 135. The MWT 160 rests in a holder attached to a side portion of the console 135. Internally, the console 135 holds the PPS 110 and a portion of the ST 120.

Figure 3:
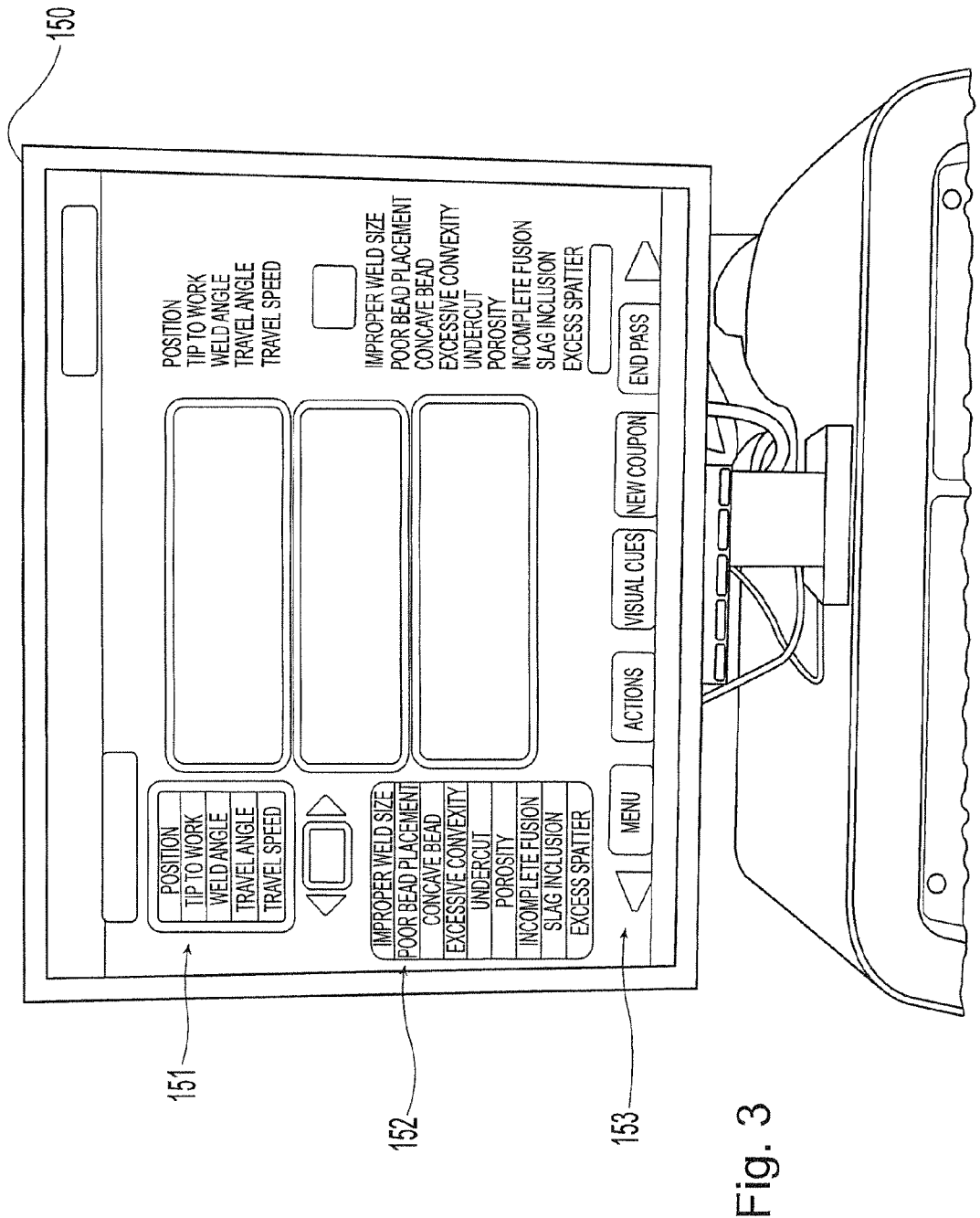
FIG. 3 illustrates an example embodiment of the observer display device (ODD) of FIG. 2.

FIG. 3 illustrates an example embodiment of the observer display device (ODD) 150 of FIG. 2. In accordance with an embodiment of the present invention, the ODD 150 is a liquid crystal display (LCD) device. Other display devices are possible as well. For example, the ODD 150 may be a touchscreen display, in accordance with another embodiment of the present invention. The ODD 150 receives video (e.g., SVGA format) and display information from the PPS 110.

As shown in FIG. 3, the ODD 150 is capable of displaying a first user scene showing various welding parameters 151 including position, tip to work, weld angle, travel angle, and travel speed. These parameters may be selected and displayed in real time in graphical form and are used to teach proper welding technique. Furthermore, as shown in FIG. 3, the ODD 150 is capable of displaying simulated welding discontinuity states 152 including, for example, improper weld size, poor bead placement, concave bead, excessive convexity, undercut, porosity, incomplete fusion, slag inclusion, excess spatter, overfill, and burnthrough (melt through). Undercut is a groove melted into the base metal adjacent to the weld or weld root and left unfilled by weld metal. Undercut is often due to an incorrect angle of welding. Porosity is cavity type discontinuities formed by gas entrapment during solidification often caused by moving the arc too far away from the coupon.

Also, as shown in FIG. 3, the ODD 50 is capable of displaying user selections 153 including menu, actions, visual cues, new coupon, and end pass. These user selections are tied to user buttons on the console 135. As a user makes various selections via, for example, a touchscreen of the ODD 150 or via the physical WUI 130, the displayed characteristics can change to provide selected information and other options to the user. Furthermore, the ODD 150 may display a view seen by a welder wearing the FMDD 140 at the same angular view of the welder or at various different angles, for example, chosen by an instructor. The ODD 150 may be viewed by an instructor and/or students for various training purposes. For example, the view may be rotated around the finished weld allowing visual inspection by an instructor. In accordance with an alternate embodiment of the present invention, video from the system 100 may be sent to a remote location via, for example, the Internet for remote viewing and/or critiquing. Furthermore, audio may be provided, allowing real-time audio communication between a student and a remote instructor.

Figure 4:
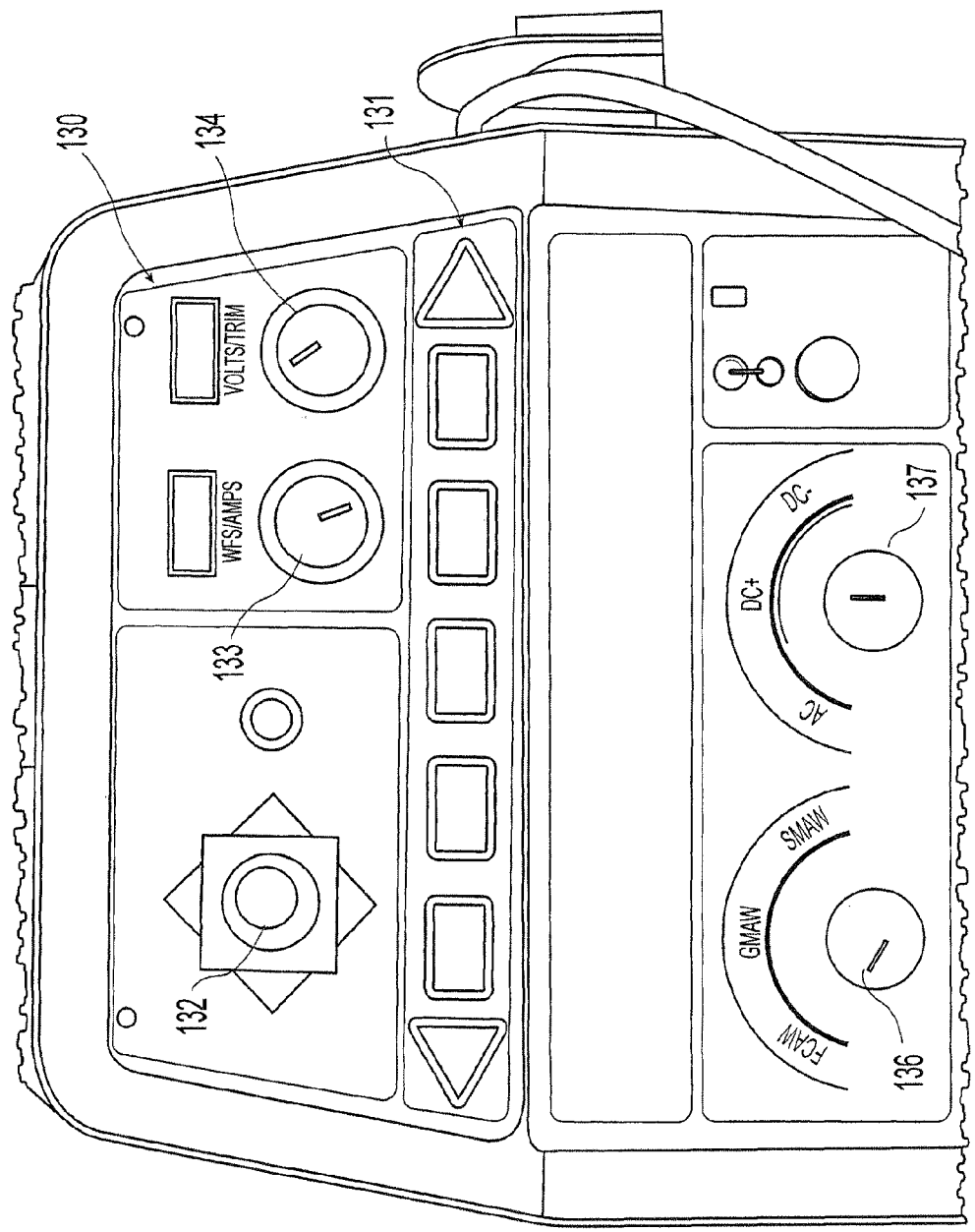
FIG. 4 illustrates an example embodiment of a front portion of the simulated welding console of FIG. 2 showing a physical welding user interface (WUI)

FIG. 4 illustrates an example embodiment of a front portion of the simulated welding console 135 of FIG. 2 showing a physical welding user interface (WUI) 130. The WUI 130 includes a set of buttons 131 corresponding to the user selections 153 displayed on the ODD 150. The buttons 131 are colored to correspond to the colors of the user selections 153 displayed on the ODD 150. When one of the buttons 131 is pressed, a signal is sent to the PPS 110 to activate the corresponding function. The WUI 130 also includes a joystick 132 capable of being used by a user to select various parameters and selections displayed on the ODD 150. The WUI 130 further includes a dial or knob 133 for adjusting wire feed speed/amps, and another dial or knob 134 for adjusting volts/trim. The WUI 130 also includes a dial or knob 136 for selecting an arc welding process. In accordance with an embodiment of the present invention, three arc welding processes are selectable including flux cored arc welding (FCAW) including gas-shielded and self-shielded processes; gas metal arc welding (GMAW) including short arc, axial spray, STT, and pulse; gas tungsten arc welding (GTAW); and shielded metal arc welding (SMAW) including E6010 and E7010 electrodes. The WUI 130 further includes a dial or knob 137 for selecting a welding polarity. In accordance with an embodiment of the present invention, three arc welding polarities are selectable including alternating current (AC), positive direct current (DC+), and negative direct current (DC−).

Figure 5:
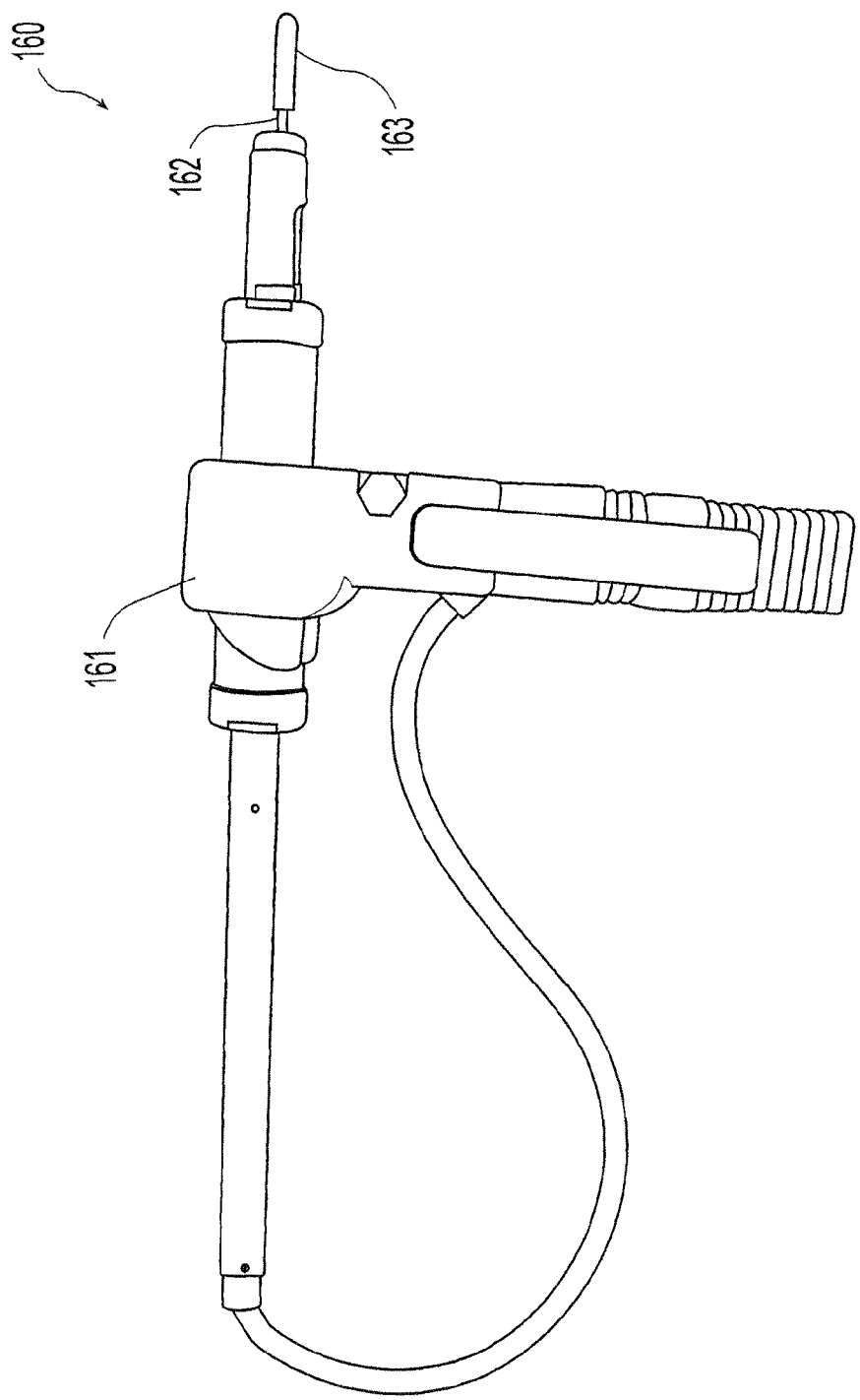
FIG. 5 illustrates an example embodiment of a mock welding tool (MWT) of the system of FIG. 1.

FIG. 5 illustrates an example embodiment of a mock welding tool (MWT) 160 of the system 100 of FIG. 1. The MWT 160 of FIG. 5 simulates a stick welding tool for plate and pipe welding and includes a holder 161 and a simulated stick electrode 162. A trigger on the MWD 160 is used to communicate a signal to the PPS 110 to activate a selected simulated welding process. The simulated stick electrode 162 includes a tactilely resistive tip 163 to simulate resistive feedback that occurs during, for example, a root pass welding procedure in real-world pipe welding or when welding a plate. If the user moves the simulated stick electrode 162 too far back out of the root, the user will be able to feel or sense the lower resistance, thereby deriving feedback for use in adjusting or maintaining the current welding process.

It is contemplated that the stick welding tool may incorporate an actuator, not shown, that withdraws the simulated stick electrode 162 during the virtual welding process. That is to say that as a user engages in virtual welding activity, the distance between holder 161 and the tip of the simulated stick electrode 162 is reduced to simulate consumption of the electrode. The consumption rate, i.e. withdrawal of the stick electrode 162, may be controlled by the PPS 110 and more specifically by coded instructions executed by the PPS 110. The simulated consumption rate may also depend on the user's technique. It is noteworthy to mention here that as the system 100 facilitates virtual welding with different types of electrodes, the consumption rate or reduction of the stick electrode 162 may change with the welding procedure used and/or setup of the system 100.

Other mock welding tools are possible as well, in accordance with other embodiments of the present invention, including a MWD that simulates a hand-held semi-automatic welding gun having a wire electrode fed through the gun, for example. Furthermore, in accordance with other certain embodiments of the present invention, a real welding tool could be used as the MWT 160 to better simulate the actual feel of the tool in the user's hands, even though, in the system 100, the tool would not be used to actually create a real arc. Also, a simulated grinding tool may be provided, for use in a simulated grinding mode of the simulator 100. Similarly, a simulated cutting tool may be provided, for use in a simulated cutting mode of the simulator 100. Furthermore, a simulated gas tungsten arc welding (GTAW) torch or filler material may be provided for use in the simulator 100.

Figure 6:
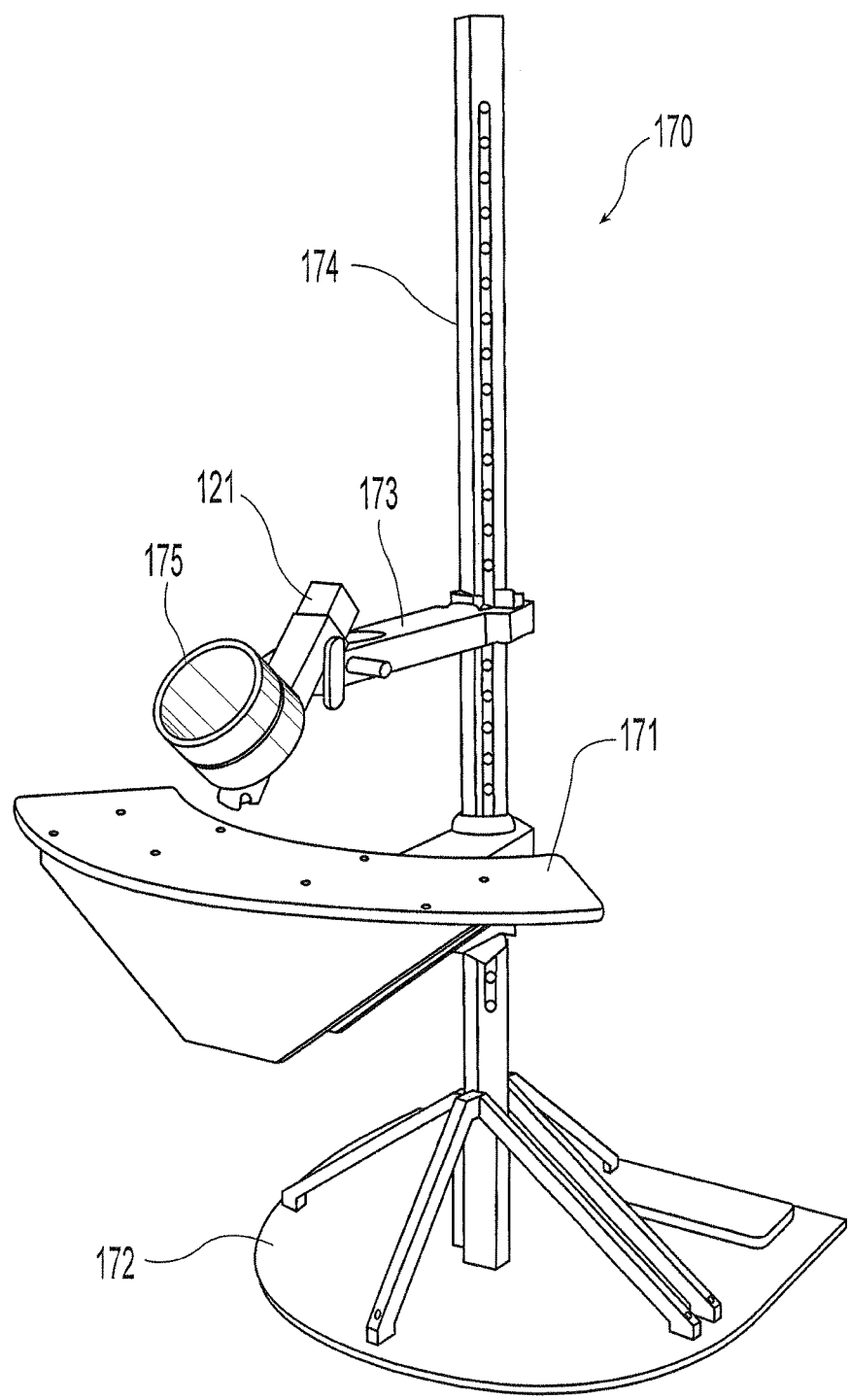
FIG. 6 illustrates an example embodiment of a table/stand (T/S) of the system of FIG. 1.

FIG. 6 illustrates an example embodiment of a table/stand (T/S) 170 of the system 100 of FIG. 1. The T/S 170 includes an adjustable table 171, a stand or base 172, an adjustable arm 173, and a vertical post 174. The table 171, the stand 172, and the arm 173 are each attached to the vertical post 174. The table 171 and the arm 173 are each capable of being manually adjusted upward, downward, and rotationally with respect to the vertical post 174. The arm 173 is used to hold various welding coupons (e.g., welding coupon 175) and a user may rest his/her arm on the table 171 when training. The vertical post 174 is indexed with position information such that a user may know exactly where the arm 173 and the table 171 are vertically positioned on the post 171. This vertical position information may be entered into the system by a user using the WUI 130 and the ODD 150.

In accordance with an alternative embodiment of the present invention, the positions of the table 171 and the arm 173 may be automatically set by the PSS 110 via preprogrammed settings, or via the WUI 130 and/or the ODD 150 as commanded by a user. In such an alternative embodiment, the T/S 170 includes, for example, motors and/or servo-mechanisms, and signal commands from the PPS 110 activate the motors and/or servo-mechanisms. In accordance with a further alternative embodiment of the present invention, the positions of the table 171 and the arm 173 and the type of coupon are detected by the system 100. In this way, a user does not have to manually input the position information via the user interface. In such an alternative embodiment, the T/S 170 includes position and orientation detectors and sends signal commands to the PPS 110 to provide position and orientation information, and the WC 175 includes position detecting sensors (e.g., coiled sensors for detecting magnetic fields). A user is able to see a rendering of the T/S 170 adjust on the ODD 150 as the adjustment parameters are changed, in accordance with an embodiment of the present invention.

FIG. 7A illustrates an example embodiment of a pipe welding coupon (WC) 175 of the system 100 of FIG. 1. The WC 175 simulates two six inch diameter pipes 175' and 175" placed together to form a root 176 to be welded. The WC 175 includes a connection portion 177 at one end of the WC 175, allowing the WC 175 to be attached in a precise and repeatable manner to the arm 173. FIG. 7B illustrates the pipe WC 175 of FIG. 7A mounted on the arm 173 of the table/stand (TS) 170 of FIG. 6. The precise and repeatable manner in which the WC 175 is capable of being attached to the arm 173 allows for spatial calibration of the WC 175 to be performed only once at the factory. Then, in the field, as long as the system 100 is told the position of the arm 173, the system 100 is able to track the MWT 160 and the FMDD 140 with respect to the WC 175 in a virtual environment. A first portion of the arm 173, to which the WC 175 is attached, is capable of being tilted with respect to a second portion of the arm 173, as shown in FIG. 6. This allows the user to practice pipe welding with the pipe in any of several different orientations and angles.

Figure 8:
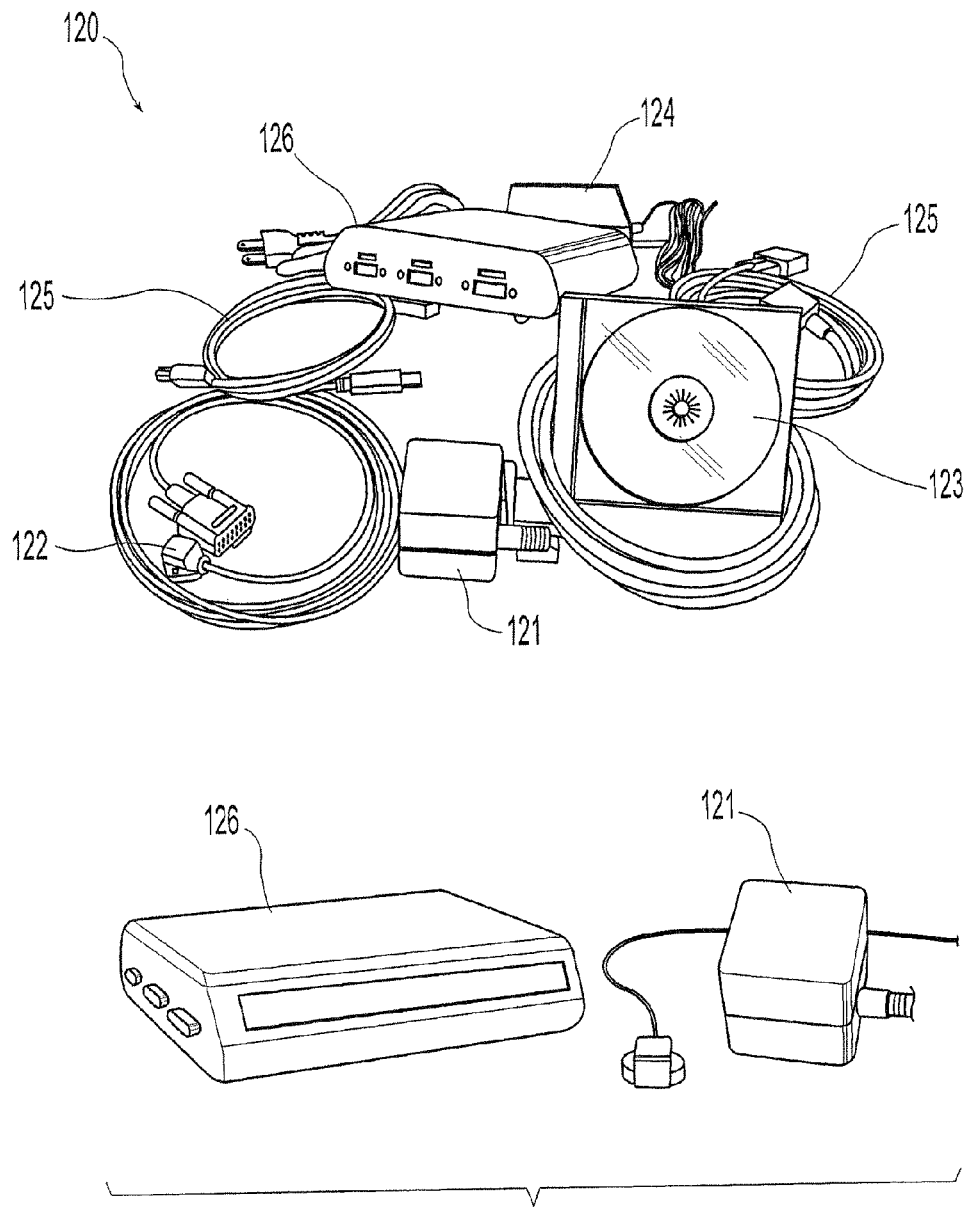
FIG. 8 illustrates various elements of an example embodiment of the spatial tracker (ST) of FIG. 1.

FIG. 8 illustrates various elements of an example embodiment of the spatial tracker (ST) 120 of FIG. 1. The ST 120 is a magnetic tracker that is capable of operatively interfacing with the PPS 110 of the system 100. The ST 120 includes a magnetic source 121 and source cable, at least one sensor 122 and associated cable, host software on disk 123, a power source 124 and associated cable, USB and RS-232 cables 125, and a processor tracking unit 126. The magnetic source 121 is capable of being operatively connected to the processor tracking unit 126 via a cable. The sensor 122 is capable of being operatively connected to the processor tracking unit 126 via a cable. The power source 124 is capable of being operatively connected to the processor tracking unit 126 via a cable. The processor tracking unit 126 is cable of being operatively connected to the PPS 110 via a USB or RS-232 cable 125. The host software on disk 123 is capable of being loaded onto the PPS 110 and allows functional communication between the ST 120 and the PPS 110.

Referring to FIG. 6, the magnetic source 121 of the ST 120 is mounted on the first portion of the arm 173. The magnetic source 121 creates a magnetic field around the source 121, including the space encompassing the WC 175 attached to the arm 173, which establishes a 3D spatial frame of reference. The T/S 170 is largely non-metallic (non-ferric and non-conductive) so as not to distort the magnetic field created by the magnetic source 121. The sensor 122 includes three induction coils orthogonally aligned along three spatial directions. The induction coils of the sensor 122 each measure the strength of the magnetic field in each of the three directions and provide that information to the processor tracking unit 126. As a result, the system 100 is able to know where any portion of the WC 175 is with respect to the 3D spatial frame of reference established by the magnetic field when the WC 175 is mounted on the arm 173. The sensor 122 may be attached to the MWT 160 or to the FMDD 140, allowing the MWT 160 or the FMDD 140 to be tracked by the ST 120 with respect to the 3D spatial frame of reference in both space and orientation. When two sensors 122 are provided and operatively connected to the processor tracking unit 126, both the MWT 160 and the FMDD 140 may be tracked. In this manner, the system 100 is capable of creating a virtual WC, a virtual MWT, and a virtual T/S in virtual reality space and displaying the virtual WC, the virtual MWT, and the virtual T/S on the FMDD 140 and/or the ODD 150 as the MWT 160 and the FMDD 140 are tracked with respect to the 3D spatial frame of reference.

In accordance with an alternative embodiment of the present invention, the sensor(s) 122 may wirelessly interface to the processor tracking unit 126, and the processor tracking unit 126 may wirelessly interface to the PPS 110. In accordance with other alternative embodiments of the present invention, other types of spatial trackers 120 may be used in the system 100 including, for example, an accelerometer/gyroscope-based tracker, an optical tracker (active or passive), an infrared tracker, an acoustic tracker, a laser tracker, a radio frequency tracker, an inertial tracker, and augmented reality based tracking systems. Other types of trackers may be possible as well.

FIG. 9A illustrates an example embodiment of the face-mounted display device 140 (FMDD) of the system 100 of FIG. 1. FIG. 9B is an illustration of how the FMDD 140 of FIG. 9A is secured on the head of a user. FIG. 9C illustrates an example embodiment of the FMDD 140 of FIG. 9A integrated into a welding helmet 900. The FMDD 140 operatively connects to the PPS 110 and the ST 120 either via wired means or wirelessly. A sensor 122 of the ST 120 may be attached to the FMDD 140 or to the welding helmet 900, in accordance with various embodiments of the present invention, allowing the FMDD 140 and/or welding helmet 900 to be tracked with respect to the 3D spatial frame of reference created by the ST 120.

In accordance with an embodiment of the present invention, the FMDD 140 includes two high-contrast SVGA 3D OLED microdisplays capable of delivering fluid full-motion video in the 2D and frame sequential video modes. Video of the virtual reality environment is provided and displayed on the FMDD 140. A zoom (e.g., 2×) mode may be provided, allowing a user to simulate a cheater lens, for example.

The FMDD 140 further includes two earbud speakers 910, allowing the user to hear simulated welding-related and environmental sounds produced by the system 100. The FMDD 140 may operatively interface to the PPS 110 via wired or wireless means, in accordance with various embodiments of the present invention. In accordance with an embodiment of the present invention, the PPS 110 provides stereoscopic video to the FMDD 140, providing enhanced depth perception to the user. In accordance with an alternate embodiment of the present invention, a user is able to use a control on the MWT 160 (e.g., a button or switch) to call up and select menus and display options on the FMDD 140. This may allow the user to easily reset a weld if he makes a mistake, change certain parameters, or back up a little to re-do a portion of a weld bead trajectory, for example.

Figure 10:
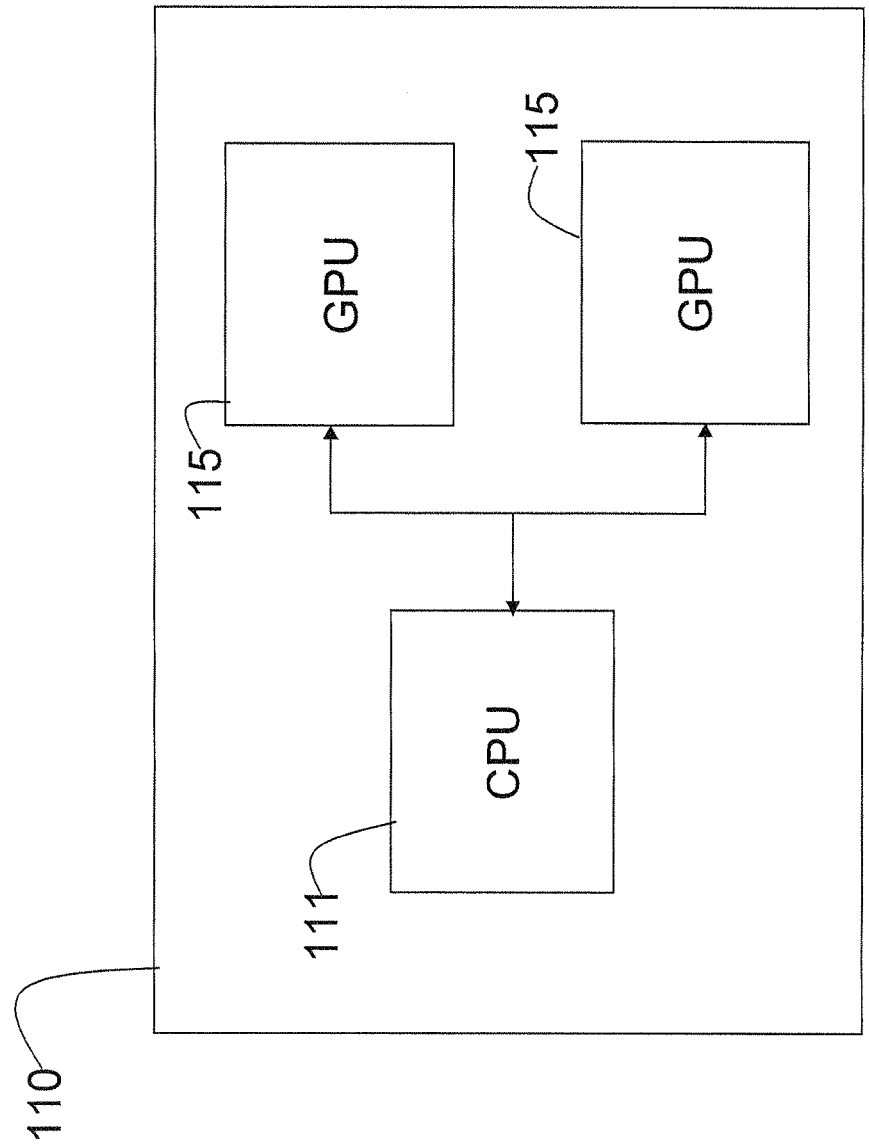
FIG. 10 illustrates an example embodiment of a subsystem block diagram of a programmable processor-based subsystem (PPS) of the system of FIG. 1.

FIG. 10 illustrates an example embodiment of a subsystem block diagram of the programmable processor-based subsystem (PPS) 110 of the system 100 of FIG. 1. The PPS 110 includes a central processing unit (CPU) 111 and two graphics processing units (GPU) 115, in accordance with an embodiment of the present invention. The two GPUs 115 are programmed to provide virtual reality simulation of a weld puddle (a.k.a. a weld pool) having real-time molten metal fluidity and heat absorption and dissipation characteristics, in accordance with an embodiment of the present invention.

Figure 11:
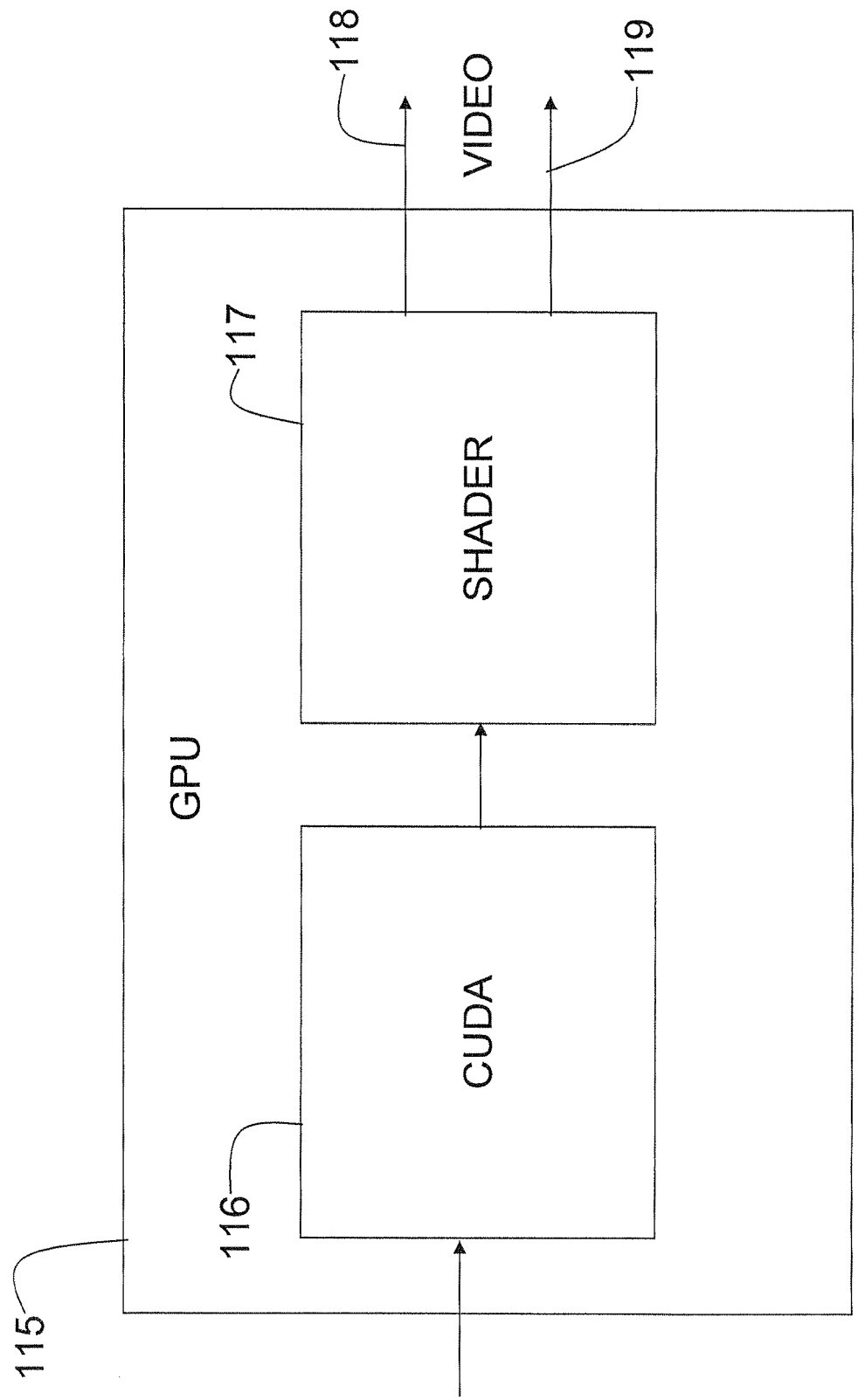
FIG. 11 illustrates an example embodiment of a block diagram of a graphics processing unit (GPU) of the PPS of FIG. 10.

FIG. 11 illustrates an example embodiment of a block diagram of a graphics processing unit (GPU) 115 of the PPS 110 of FIG. 10. Each GPU 115 supports the implementation of data parallel algorithms. In accordance with an embodiment of the present invention, each GPU 115 provides two video outputs 118 and 119 capable of providing two virtual reality views. Two of the video outputs may be routed to the FMDD 140, rendering the welder's point of view, and a third video output may be routed to the ODD 150, for example, rendering either the welder's point of view or some other point of view. The remaining fourth video output may be routed to a projector, for example. Both GPUs 115 perform the same welding physics computations but may render the virtual reality environment from the same or different points of view. The GPU 115 includes a compute unified device architecture (CUDA) 116 and a shader 117. The CUDA 116 is the computing engine of the GPU 115 which is accessible to software developers through industry standard programming languages. The CUDA 116 includes parallel cores and is used to run the physics model of the weld puddle simulation described herein. The CPU 111 provides real-time welding input data to the CUDA 116 on the GPU 115. The shader 117 is responsible for drawing and applying all of the visuals of the simulation. Bead and puddle visuals are driven by the state of a wexel displacement map which is described later herein. In accordance with an embodiment of the present invention, the physics model runs and updates at a rate of about 30 times per second.

Figure 12:
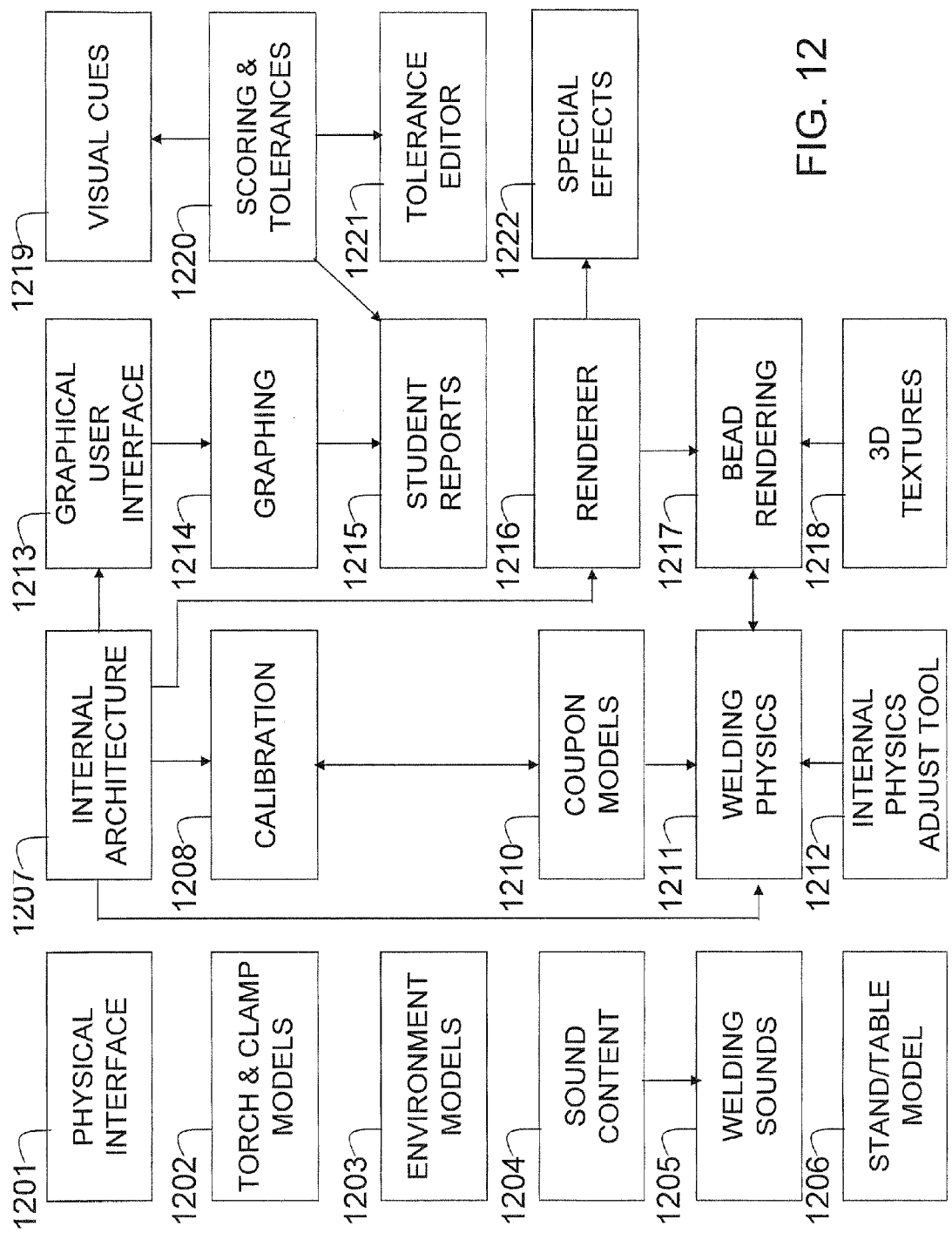
FIG. 12 illustrates an example embodiment of a functional block diagram of the system of FIG. 1.

FIG. 12 illustrates an example embodiment of a functional block diagram of the system 100 of FIG. 1. The various functional blocks of the system 100 as shown in FIG. 12 are implemented largely via software instructions and modules running on the PPS 110. The various functional blocks of the system 100 include a physical interface 1201, torch and clamp models 1202, environment models 1203, sound content functionality 1204, welding sounds 1205, stand/table model 1206, internal architecture functionality 1207, calibration functionality 1208, coupon models 1210, welding physics 1211, internal physics adjustment tool (tweaker) 1212, graphical user interface functionality 1213, graphing functionality 1214, student reports functionality 1215, renderer 1216, bead rendering 1217, 3D textures 1218, visual cues functionality 1219, scoring and tolerance functionality 1220, tolerance editor 1221, and special effects 1222.

The internal architecture functionality 1207 provides the higher level software logistics of the processes of the system 100 including, for example, loading files, holding information, managing threads, turning the physics model on, and triggering menus. The internal architecture functionality 1207 runs on the CPU 111, in accordance with an embodiment of the present invention. Certain real-time inputs to the PPS 110 include arc location, gun position, FMDD or helmet position, gun on/off state, and contact made state (yes/no).

The graphical user interface functionality 1213 allows a user, through the ODD 150 using the joystick 132 of the physical user interface 130, to set up a welding scenario. In accordance with an embodiment of the present invention, the set up of a welding scenario includes selecting a language, entering a user name, selecting a practice plate (i.e., a welding coupon), selecting a welding process (e.g., FCAW, GMAW, SMAW) and associated axial spray, pulse, or short arc methods, selecting a gas type and flow rate, selecting a type of stick electrode (e.g., 6010 or 7018), and selecting a type of flux cored wire (e.g., self-shielded, gas-shielded). The set up of a welding scenario also includes selecting a table height, an arm height, an arm position, and an arm rotation of the T/S 170. The set up of a welding scenario further includes selecting an environment (e.g., a background environment in virtual reality space), setting a wire feed speed, setting a voltage level, setting an amperage, selecting a polarity, and turning particular visual cues on or off.

During a simulated welding scenario, the graphing functionality 1214 gathers user performance parameters and provides the user performance parameters to the graphical user interface functionality 1213 for display in a graphical format (e.g., on the ODD 150). Tracking information from the ST 120 feeds into the graphing functionality 1214. The graphing functionality 1214 includes a simple analysis module (SAM) and a whip/weave analysis module (WWAM). The SAM analyzes user welding parameters including welding travel angle, travel speed, weld angle, position, and tip to work distance by comparing the welding parameters to data stored in bead tables. The WWAM analyzes user whipping parameters including dime spacing, whip time, and puddle time. The WWAM also analyzes user weaving parameters including width of weave, weave spacing, and weave timing. The SAM and WWAM interpret raw input data (e.g., position and orientation data) into functionally usable data for graphing. For each parameter analyzed by the SAM and the WWAM, a tolerance window is defined by parameter limits around an optimum or ideal set point input into bead tables using the tolerance editor 1221, and scoring and tolerance functionality 1220 is performed.

The tolerance editor 1221 includes a weldometer which approximates material usage, electrical usage, and welding time. Furthermore, when certain parameters are out of tolerance, welding discontinuities (i.e., welding defects) may occur. The state of any welding discontinuities are processed by the graphing functionality 1214 and presented via the graphical user interface functionality 1213 in a graphical format. Such welding discontinuities include improper weld size, poor bead placement, concave bead, excessive convexity, undercut, porosity, incomplete fusion, slag entrapment, overfill, burnthrough, and excessive spatter. In accordance with an embodiment of the present invention, the level or amount of a discontinuity is dependent on how far away a particular user parameter is from the optimum or ideal set point.

Different parameter limits may be pre-defined for different types of users such as, for example, welding novices, welding experts, and persons at a trade show. The scoring and tolerance functionality 1220 provide number scores depending on how close to optimum (ideal) a user is for a particular parameter and depending on the level of discontinuities or defects present in the weld. The optimum values are derived from real-world data. Information from the scoring and tolerance functionality 1220 and from the graphics functionality 1214 may be used by the student reports functionality 1215 to create a performance report for an instructor and/or a student.

The system 100 is capable of analyzing and displaying the results of virtual welding activity. By analyzing the results, it is meant that system 100 is capable of determining when during the welding pass and where along the weld joints, the user deviated from the acceptable limits of the welding process. A score may be attributed to the user's performance. In one embodiment, the score may be a function of deviation in position, orientation and speed of the mock welding tool 160 through ranges of tolerances, which may extend from an ideal welding pass to marginal or unacceptable welding activity. Any gradient of ranges may be incorporated into the system 100 as chosen for scoring the user's performance. Scoring may be displayed numerically or alpha-numerically. Additionally, the user's performance may be displayed graphically showing, in time and/or position along the weld joint, how closely the mock welding tool traversed the weld joint. Parameters such as travel angle, work angle, speed, and distance from the weld joint are examples of what may be measured, although any parameters may be analyzed for scoring purposes. The tolerance ranges of the parameters are taken from real-world welding data, thereby providing accurate feedback as to how the user will perform in the real world. In another embodiment, analysis of the defects corresponding to the user's performance may also be incorporated and displayed on the ODD 150. In this embodiment, a graph may be depicted indicating what type of discontinuity resulted from measuring the various parameters monitored during the virtual welding activity. While occlusions may not be visible on the ODD 150, defects may still have occurred as a result of the user's performance, the results of which may still be correspondingly displayed, i.e. graphed.

Visual cues functionality 1219 provide immediate feedback to the user by displaying overlaid colors and indicators on the FMDD 140 and/or the ODD 150. Visual cues are provided for each of the welding parameters 151 including position, tip to work distance, weld angle, travel angle, travel speed, and arc length (e.g., for stick welding) and visually indicate to the user if some aspect of the user's welding technique should be adjusted based on the pre-defined limits or tolerances. Visual cues may also be provided for whip/weave technique and weld bead "dime" spacing, for example. Visual cues may be set independently or in any desired combination.

Calibration functionality 1208 provides the capability to match up physical components in real world space (3D frame of reference) with visual components in virtual reality space. Each different type of welding coupon (WC) is calibrated in the factory by mounting the WC to the arm 173 of the T/S 170 and touching the WC at predefined points (indicated by, for example, three dimples on the WC) with a calibration stylus operatively connected to the ST 120. The ST 120 reads the magnetic field intensities at the predefined points, provides position information to the PPS 110, and the PPS 110 uses the position information to perform the calibration (i.e., the translation from real world space to virtual reality space).

Any particular type of WC fits into the arm 173 of the T/S 170 in the same repeatable way to within very tight tolerances. Therefore, once a particular WC type is calibrated, that WC type does not have to be re-calibrated (i.e., calibration of a particular type of WC is a one-time event). WCs of the same type are interchangeable. Calibration ensures that physical feedback perceived by the user during a welding process matches up with what is displayed to the user in virtual reality space, making the simulation seem more real. For example, if the user slides the tip of a MWT 160 around the corner of a actual WC 180, the user will see the tip sliding around the corner of the virtual WC on the FMDD 140 as the user feels the tip sliding around the actual corner. In accordance with an embodiment of the present invention, the MWT 160 is placed in a pre-positioned jig and is calibrated as well, based on the known jig position.

In accordance with an alternative embodiment of the present invention, "smart" coupons are provided, having sensors on, for example, the corners of the coupons. The ST 120 is able to track the corners of a "smart" coupon such that the system 100 continuously knows where the "smart" coupon is in real world 3D space. In accordance with a further alternative embodiment of the present invention, licensing keys are provided to "unlock" welding coupons. When a particular WC is purchased, a licensing key is provided allowing the user to enter the licensing key into the system 100, unlocking the software associated with that WC. In accordance with another embodiment of the present invention, special non-standard welding coupons may be provided based on real-world CAD drawings of parts. Users may be able to train on welding a CAD part even before the part is actually produced in the real world.

Sound content functionality 1204 and welding sounds 1205 provide particular types of welding sounds that change depending on if certain welding parameters are within tolerance or out of tolerance. Sounds are tailored to the various welding processes and parameters. For example, in a MIG spray arc welding process, a crackling sound is provided when the user does not have the MWT 160 positioned correctly, and a hissing sound is provided when the MWT 160 is positioned correctly. In a short arc welding process, a steady crackling or frying sound is provided for proper welding technique, and a hissing sound may be provided when undercutting is occurring. These sounds mimic real world sounds corresponding to correct and incorrect welding technique.

High fidelity sound content may be taken from real world recordings of actual welding using a variety of electronic and mechanical means, in accordance with various embodiments of the present invention. In accordance with an embodiment of the present invention, the perceived volume and directionality of sound is modified depending on the position, orientation, and distance of the user's head (assuming the user is wearing a FMDD 140 that is tracked by the ST 120) with respect to the simulated arc between the MWT 160 and the WC 180. Sound may be provided to the user via ear bud speakers 910 in the FMDD 140 or via speakers configured in the console 135 or T/S 170, for example.

Environment models 1203 are provided to provide various background scenes (still and moving) in virtual reality space. Such background environments may include, for example, an indoor welding shop, an outdoor race track, a garage, etc. and may include moving cars, people, birds, clouds, and various environmental sounds. The background environment may be interactive, in accordance with an embodiment of the present invention. For example, a user may have to survey a background area, before starting welding, to ensure that the environment is appropriate (e.g., safe) for welding. Torch and clamp models 1202 are provided which model various MWTs 160 including, for example, guns, holders with stick electrodes, etc. in virtual reality space.

Coupon models 1210 are provided which model various WCs 180 including, for example, flat plate coupons, T-joint coupons, butt-joint coupons, groove-weld coupons, and pipe coupons (e.g., 2-inch diameter pipe and 6-inch diameter pipe) in virtual reality space. A stand/table model 1206 is provided which models the various parts of the T/S 170 including an adjustable table 171, a stand 172, an adjustable arm 173, and a vertical post 174 in virtual reality space. A physical interface model 1201 is provided which models the various parts of the welding user interface 130, console 135, and ODD 150 in virtual reality space.

In accordance with an embodiment of the present invention, simulation of a weld puddle or pool in virtual reality space is accomplished where the simulated weld puddle has real-time molten metal fluidity and heat dissipation characteristics. At the heart of the weld puddle simulation is the welding physics functionality 1211 (a.k.a., the physics model) which is run on the GPUs 115, in accordance with an embodiment of the present invention. The welding physics functionality employs a double displacement layer technique to accurately model dynamic fluidity/viscosity, solidity, heat gradient (heat absorption and dissipation), puddle wake, and bead shape, and is described in more detail herein with respect to FIGS. 14A-14C.

The welding physics functionality 1211 communicates with the bead rendering functionality 1217 to render a weld bead in all states from the heated molten state to the cooled solidified state. The bead rendering functionality 1217 uses information from the welding physics functionality 1211 (e.g., heat, fluidity, displacement, dime spacing) to accurately and realistically render a weld bead in virtual reality space in real-time. The 3D textures functionality 1218 provides texture maps to the bead rendering functionality 1217 to overlay additional textures (e.g., scorching, slag, grain) onto the simulated weld bead. For example, slag may be shown rendered over a weld bead during and just after a welding process, and then removed to reveal the underlying weld bead. The renderer functionality 1216 is used to render various non-puddle specific characteristics using information from the special effects module 1222 including sparks, spatter, smoke, arc glow, fumes and gases, and certain discontinuities such as, for example, undercut and porosity.

The internal physics adjustment tool 1212 is a tweaking tool that allows various welding physics parameters to be defined, updated, and modified for the various welding processes. In accordance with an embodiment of the present invention, the internal physics adjustment tool 1212 runs on the CPU 111 and the adjusted or updated parameters are downloaded to the GPUs 115. The types of parameters that may be adjusted via the internal physics adjustment tool 1212 include parameters related to welding coupons, process parameters that allow a process to be changed without having to reset a welding coupon (allows for doing a second pass), various global parameters that can be changed without resetting the entire simulation, and other various parameters.

FIG. 13 is a flow chart of an embodiment of a method 1300 of training using the virtual reality training system 100 of FIG. 1. In step 1310, move a mock welding tool with respect to a welding coupon in accordance with a welding technique. In step 1320, track position and orientation of the mock welding tool in three-dimensional space using a virtual reality system. In step 1330, view a display of the virtual reality welding system showing a real-time virtual reality simulation of the mock welding tool and the welding coupon in a virtual reality space as the simulated mock welding tool deposits a simulated weld bead material onto at least one simulated surface of the simulated welding coupon by forming a simulated weld puddle in the vicinity of a simulated arc emitting from said simulated mock welding tool. In step 1340, view on the display, real-time molten metal fluidity and heat dissipation characteristics of the simulated weld puddle. In step 1350, modify in real-time, at least one aspect of the welding technique in response to viewing the real-time molten metal fluidity and heat dissipation characteristics of the simulated weld puddle.

The method 1300 illustrates how a user is able to view a weld puddle in virtual reality space and modify his welding technique in response to viewing various characteristics of the simulated weld puddle, including real-time molten metal fluidity (e.g., viscosity) and heat dissipation. The user may also view and respond to other characteristics including real-time puddle wake and dime spacing. Viewing and responding to characteristics of the weld puddle is how most welding operations are actually performed in the real world. The double displacement layer modeling of the welding physics functionality 1211 run on the GPUs 115 allows for such real-time molten metal fluidity and heat dissipation characteristics to be accurately modeled and represented to the user. For example, heat dissipation determines solidification time (i.e., how much time it takes for a wexel to completely solidify).

Furthermore, a user may make a second pass over the weld bead material using the same or a different (e.g., a second) mock welding tool and/or welding process. In such a second pass scenario, the simulation shows the simulated mock welding tool, the welding coupon, and the original simulated weld bead material in virtual reality space as the simulated mock welding tool deposits a second simulated weld bead material merging with the first simulated weld bead material by forming a second simulated weld puddle in the vicinity of a simulated arc emitting from the simulated mock welding tool. Additional subsequent passes using the same or different welding tools or processes may be made in a similar manner. In any second or subsequent pass, the previous weld bead material is merged with the new weld bead material being deposited as a new weld puddle is formed in virtual reality space from the combination of any of the previous weld bead material, the new weld bead material, and possibly the underlying coupon material in accordance with certain embodiments of the present invention. Such subsequent passes may be needed to make a large fillet or groove weld, performed to repair a weld bead formed by a previous pass, for example, or may include a hot pass and one or more fill and cap passes after a root pass as is done in pipe welding. In accordance with various embodiments of the present invention, weld bead and base material may include mild steel, stainless steel, aluminum, nickel based alloys, or other materials.

FIGS. 14A-14B illustrate the concept of a welding element (wexel) displacement map 1420, in accordance with an embodiment of the present invention. FIG. 14A shows a side view of a flat welding coupon (WC) 1400 having a flat top surface 1410. The welding coupon 1400 exists in the real world as, for example, a plastic part, and also exists in virtual reality space as a simulated welding coupon. FIG. 14B shows a representation of the top surface 1410 of the simulated WC 1400 broken up into a grid or array of welding elements (i.e., wexels) forming a wexel map 1420. Each wexel (e.g., wexel 1421) defines a small portion of the surface 1410 of the welding coupon. The wexel map defines the surface resolution. Changeable channel parameter values are assigned to each wexel, allowing values of each wexel to dynamically change in real-time in virtual reality weld space during a simulated welding process. The changeable channel parameter values correspond to the channels Puddle (molten metal fluidity/viscosity displacement), Heat (heat absorption/dissipation), Displacement (solid displacement), and Extra (various extra states, e.g., slag, grain, scorching, virgin metal). These changeable channels are referred to herein as PHED for Puddle, Heat, Extra, and Displacement, respectively.

Figure 15:
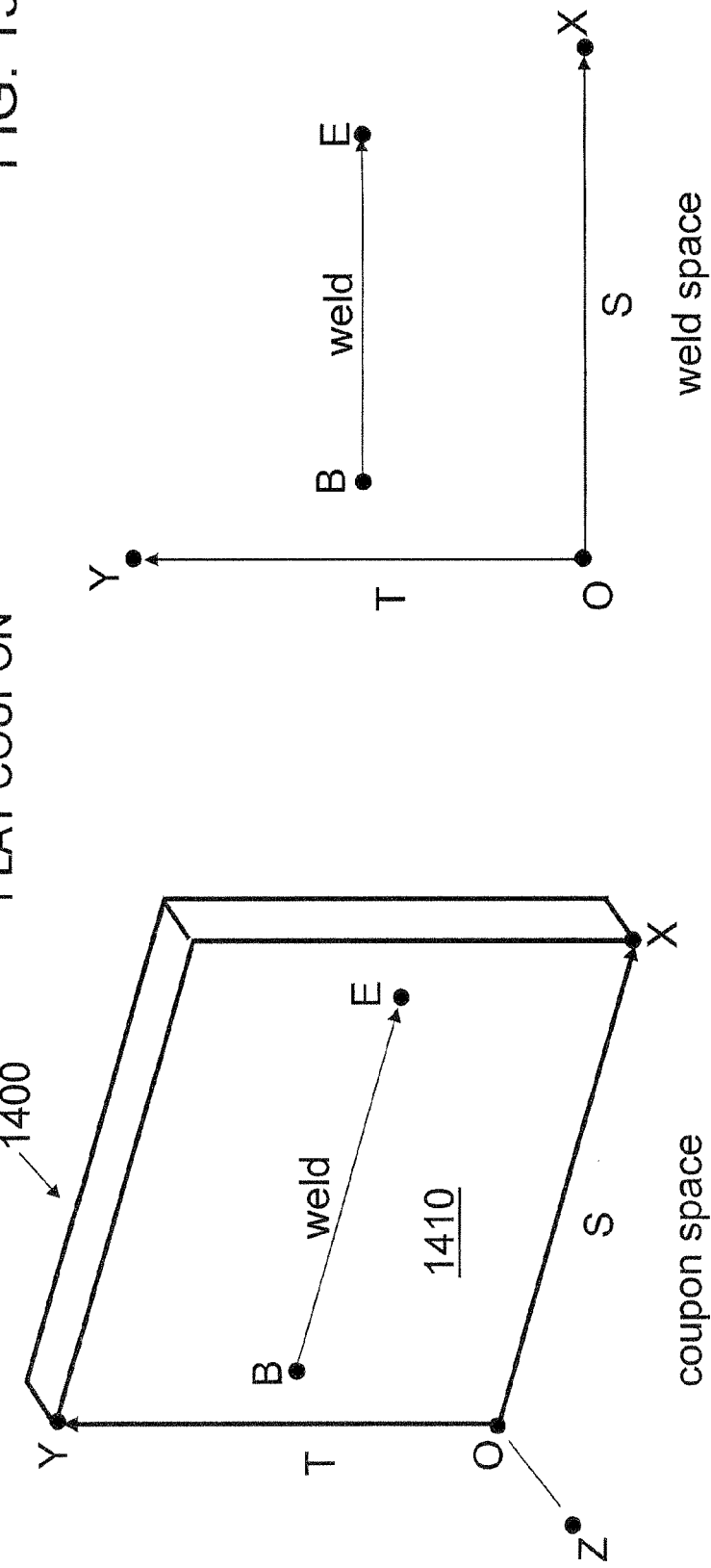
FIG. 15 illustrates an example embodiment of a coupon space and a weld space of a flat welding coupon (WC) simulated in the system of FIG. 1.

FIG. 15 illustrates an example embodiment of a coupon space and a weld space of the flat welding coupon (WC) 1400 of FIG. 14 simulated in the system 100 of FIG. 1. Points O, X, Y, and Z define the local 3D coupon space. In general, each coupon type defines the mapping from 3D coupon space to 2D virtual reality weld space. The wexel map 1420 of FIG. 14 is a two-dimensional array of values that map to weld space in virtual reality. A user is to weld from point B to point E as shown in FIG. 15. A trajectory line from point B to point E is shown in both 3D coupon space and 2D weld space in FIG. 15.

Each type of coupon defines the direction of displacement for each location in the wexel map. For the flat welding coupon of FIG. 15, the direction of displacement is the same at all locations in the wexel map (i.e., in the Z-direction). The texture coordinates of the wexel map are shown as S, T (sometimes called U, V) in both 3D coupon space and 2D weld space, in order to clarify the mapping. The wexel map is mapped to and represents the rectangular surface 1410 of the welding coupon 1400.

Figure 16:
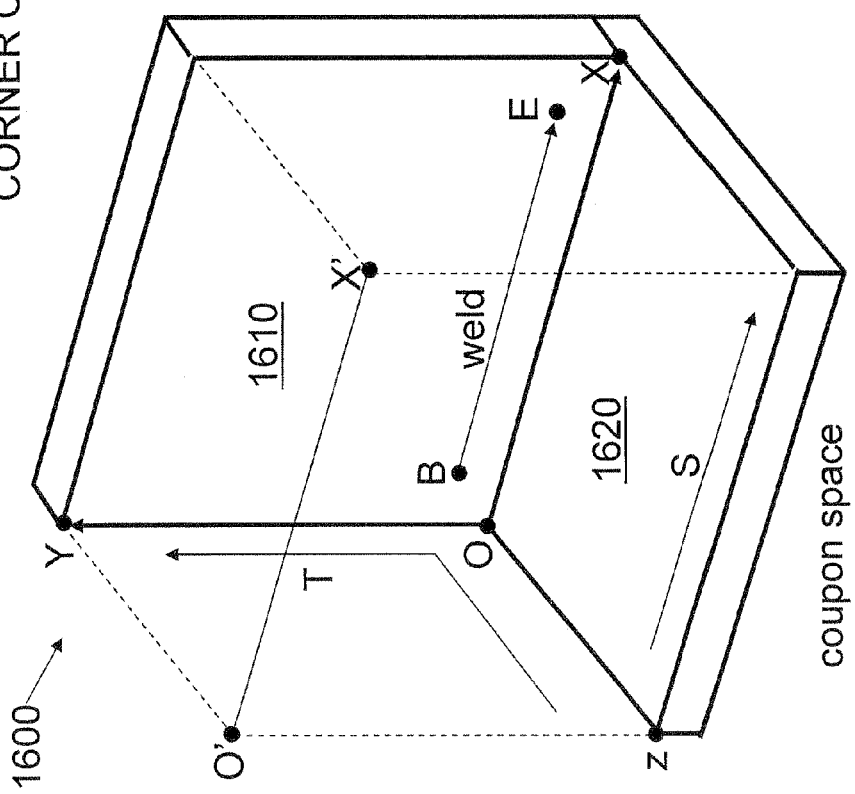
FIG. 16 illustrates an example embodiment of a coupon space and a weld space of a corner (tee joint) welding coupon (WC) simulated in the system of FIG. 1.

FIG. 16 illustrates an example embodiment of a coupon space and a weld space of a corner (tee joint) welding coupon (WC) 1600 simulated in the system 100 of FIG. 1. The corner WC 1600 has two surfaces 1610 and 1620 in 3D coupon space that are mapped to 2D weld space as shown in FIG. 16. Again, points O, X, Y, and Z define the local 3D coupon space. The texture coordinates of the wexel map are shown as S, T in both 3D coupon space and 2D weld space, in order to clarify the mapping. A user is to weld from point B to point E as shown in FIG. 16. A trajectory line from point B to point E is shown in both 3D coupon space and 2D weld space in FIG. 16. However, the direction of displacement is towards the line X'-O' as shown in the 3D coupon space, towards the opposite corner as shown in FIG. 16.

Figure 18:
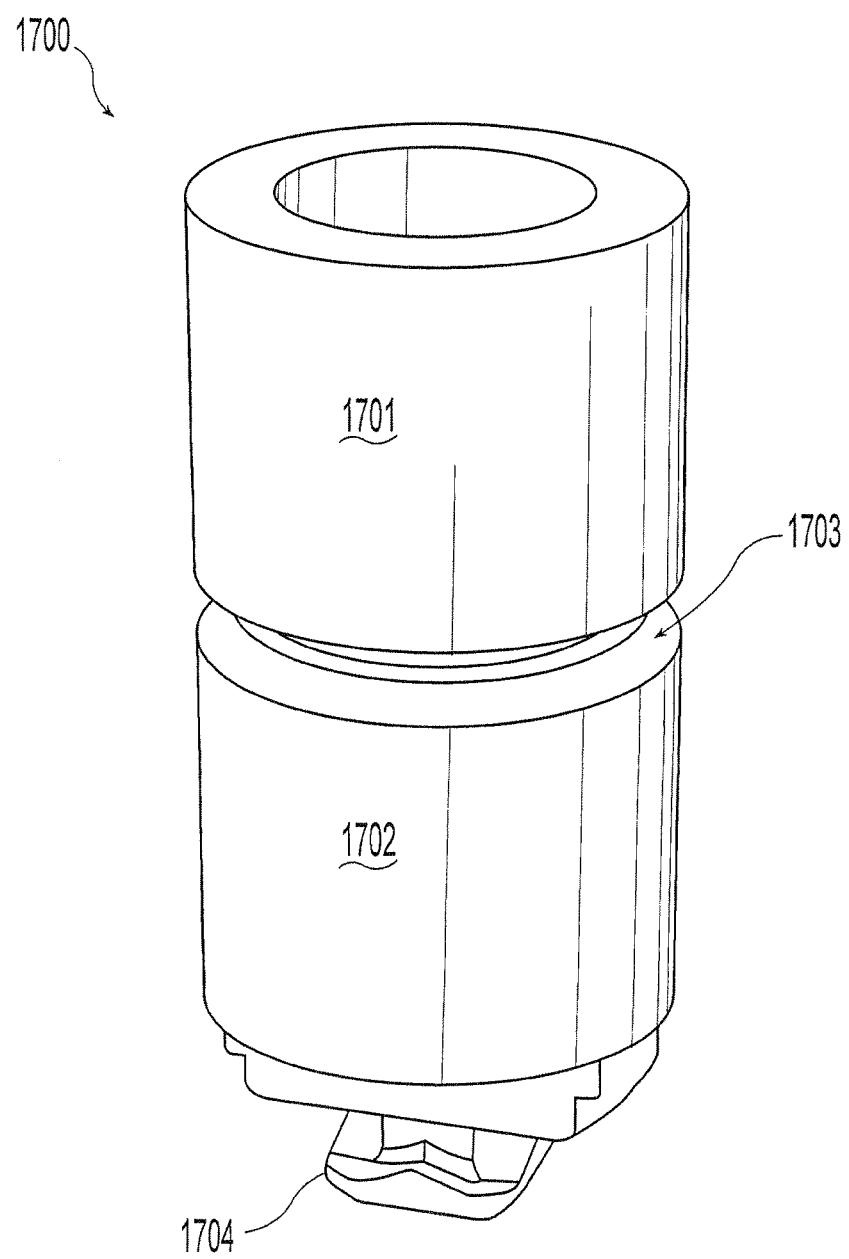
FIG. 18 illustrates an example embodiment of the pipe welding coupon (WC) of FIG. 17.

FIG. 17 illustrates an example embodiment of a coupon space and a weld space of a pipe welding coupon (WC) 1700 simulated in the system 100 of FIG. 1. The pipe WC 1700 has a curved surface 1710 in 3D coupon space that is mapped to 2D weld space as shown in FIG. 17. Again, points O, X, Y, and Z define the local 3D coupon space. The texture coordinates of the wexel map are shown as S, T in both 3D coupon space and 2D weld space, in order to clarify the mapping. A user is to weld from point B to point E along a curved trajectory as shown in FIG. 17. A trajectory curve and line from point B to point E is shown in 3D coupon space and 2D weld space, respectively, in FIG. 17. The direction of displacement is away from the line Y-O (i.e., away from the center of the pipe). FIG. 18 illustrates an example embodiment of the pipe welding coupon (WC) 1700 of FIG. 17. The pipe WC 1700 is made of a non-ferric, non-conductive plastic and simulates two pipe pieces 1701 and 1702 coming together to form a root joint 1703. An attachment piece 1704 for attaching to the arm 173 of the T/S 170 is also shown.

In a similar manner that a texture map may be mapped to a rectangular surface area of a geometry, a weldable wexel map may be mapped to a rectangular surface of a welding coupon. Each element of the weldable map is termed a wexel in the same sense that each element of a picture is termed a pixel (a contraction of picture element). A pixel contains channels of information that define a color (e.g., red, green, blue, etc.). A wexel contains channels of information (e.g., P, H, E, D) that define a weldable surface in virtual reality space.

In accordance with an embodiment of the present invention, the format of a wexel is summarized as channels PHED (Puddle, Heat, Extra, Displacement) which contains four floating point numbers. The Extra channel is treated as a set of bits which store logical information about the wexel such as, for example, whether or not there is any slag at the wexel location. The Puddle channel stores a displacement value for any liquefied metal at the wexel location. The Displacement channel stores a displacement value for the solidified metal at the wexel location. The Heat channel stores a value giving the magnitude of heat at the wexel location. In this way, the weldable part of the coupon can show displacement due to a welded bead, a shimmering surface "puddle" due to liquid metal, color due to heat, etc. All of these effects are achieved by the vertex and pixel shaders applied to the weldable surface.

In accordance with an embodiment of the present invention, a displacement map and a particle system are used where the particles can interact with each other and collide with the displacement map. The particles are virtual dynamic fluid particles and provide the liquid behavior of the weld puddle but are not rendered directly (i.e., are not visually seen directly). Instead, only the particle effects on the displacement map are visually seen. Heat input to a wexel affects the movement of nearby particles. There are two types of displacement involved in simulating a welding puddle which include Puddle and Displacement. Puddle is "temporary" and only lasts as long as there are particles and heat present. Displacement is "permanent". Puddle displacement is the liquid metal of the weld which changes rapidly (e.g., shimmers) and can be thought of as being "on top" of the Displacement. The particles overlay a portion of a virtual surface displacement map (i.e., a wexel map). The Displacement represents the permanent solid metal including both the initial base metal and the weld bead that has solidified.

In accordance with an embodiment of the present invention, the simulated welding process in virtual reality space works as follows: Particles stream from the emitter (emitter of the simulated MWT 160) in a thin cone. The particles make first contact with the surface of the simulated welding coupon where the surface is defined by a wexel map. The particles interact with each other and the wexel map and build up in real-time. More heat is added the nearer a wexel is to the emitter. Heat is modeled in dependence on distance from the arc point and the amount of time that heat is input from the arc. Certain visuals (e.g., color, etc.) are driven by the heat. A weld puddle is drawn or rendered in virtual reality space for wexels having enough heat. Wherever it is hot enough, the wexel map liquefies, causing the Puddle displacement to "raise up" for those wexel locations. Puddle displacement is determined by sampling the "highest" particles at each wexel location. As the emitter moves on along the weld trajectory, the wexel locations left behind cool. Heat is removed from a wexel location at a particular rate. When a cooling threshold is reached, the wexel map solidifies. As such, the Puddle displacement is gradually converted to Displacement (i.e., a solidified bead). Displacement added is equivalent to Puddle removed such that the overall height does not change. Particle lifetimes are tweaked or adjusted to persist until solidification is complete. Certain particle properties that are modeled in the system 100 include attraction/repulsion, velocity (related to heat), dampening (related to heat dissipation), direction (related to gravity).

Figure 19A:
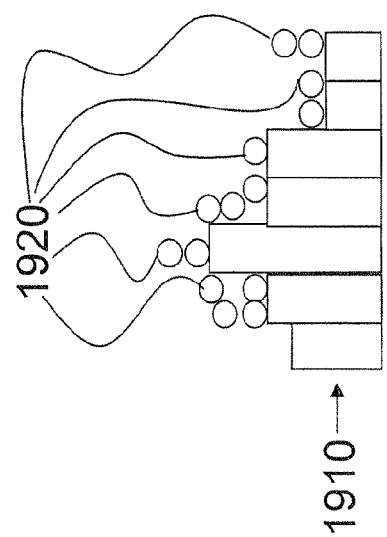
FIGS. 19A-19C illustrate an example embodiment of the concept of a dual-displacement puddle model of the system of FIG. 1.
Figure 19B:
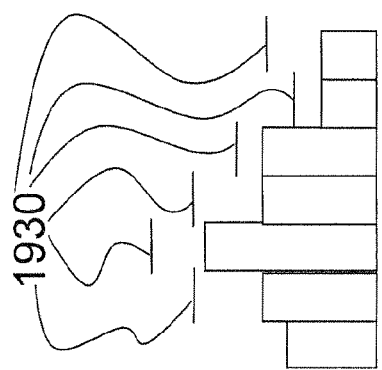
Figure 19C:
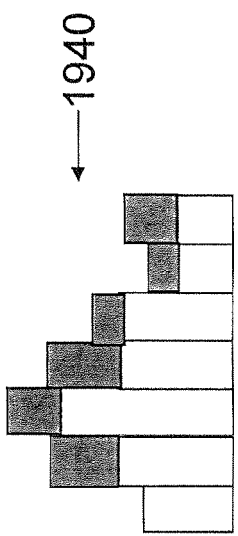

FIGS. 19A-19C illustrate an example embodiment of the concept of a dual-displacement (displacement and particles) puddle model of the system 100 of FIG. 1. Welding coupons are simulated in virtual reality space having at least one surface. The surfaces of the welding coupon are simulated in virtual reality space as a double displacement layer including a solid displacement layer and a puddle displacement layer. The puddle displacement layer is capable of modifying the solid displacement layer.

As described herein, "puddle" is defined by an area of the wexel map where the Puddle value has been raised up by the presence of particles. The sampling process is represented in FIGS. 19A-19C. A section of a wexel map is shown having seven adjacent wexels. The current Displacement values are represented by un-shaded rectangular bars 1910 of a given height (i.e., a given displacement for each wexel). In FIG. 19A, the particles 1920 are shown as round un-shaded dots colliding with the current Displacement levels and are piled up. In FIG. 19B, the "highest" particle heights 1930 are sampled at each wexel location. In FIG. 19C, the shaded rectangles 1940 show how much Puddle has been added on top of the Displacement as a result of the particles. The weld puddle height is not instantly set to the sampled values since Puddle is added at a particular liquification rate based on Heat. Although not shown in FIGS. 19A-19C, it is possible to visualize the solidification process as the Puddle (shaded rectangles) gradually shrink and the Displacement (un-shaded rectangles) gradually grow from below to exactly take the place of the Puddle. In this manner, real-time molten metal fluidity characteristics are accurately simulated. As a user practices a particular welding process, the user is able to observe the molten metal fluidity characteristics and the heat dissipation characteristics of the weld puddle in real-time in virtual reality space and use this information to adjust or maintain his welding technique.

The number of wexels representing the surface of a welding coupon is fixed. Furthermore, the puddle particles that are generated by the simulation to model fluidity are temporary, as described herein. Therefore, once an initial puddle is generated in virtual reality space during a simulated welding process using the system 100, the number of wexels plus puddle particles tends to remain relatively constant. This is because the number of wexels that are being processed is fixed and the number of puddle particles that exist and are being processed during the welding process tend to remain relatively constant because puddle particles are being created and "destroyed" at a similar rate (i.e., the puddle particles are temporary). Therefore, the processing load of the PPS 110 remains relatively constant during a simulated welding session.

In accordance with an alternate embodiment of the present invention, puddle particles may be generated within or below the surface of the welding coupon. In such an embodiment, displacement may be modeled as being positive or negative with respect to the original surface displacement of a virgin (i.e., un-welded) coupon. In this manner, puddle particles may not only build up on the surface of a welding coupon, but may also penetrate the welding coupon. However, the number of wexels is still fixed and the puddle particles being created and destroyed is still relatively constant.

In accordance with alternate embodiments of the present invention, instead of modeling particles, a wexel displacement map may be provided having more channels to model the fluidity of the puddle. Or, instead of modeling particles, a dense voxel map may be modeled. Or, instead of a wexel map, only particles may be modeled which are sampled and never go away. Such alternative embodiments may not provide a relatively constant processing load for the system, however.

Furthermore, in accordance with an embodiment of the present invention, blowthrough or a keyhole is simulated by taking material away. For example, if a user keeps an arc in the same location for too long, in the real world, the material would burn away causing a hole. Such real-world burnthrough is simulated in the system 100 by wexel decimation techniques. If the amount of heat absorbed by a wexel is determined to be too high by the system 100, that wexel may be flagged or designated as being burned away and rendered as such (e.g., rendered as a hole). Subsequently, however, wexel re-constitution may occur for certain welding processes (e.g., pipe welding) where material is added back after being initially burned away. In general, the system 100 simulates wexel decimation (taking material away) and wexel reconstitution (i.e., adding material back). Furthermore, removing material in root-pass welding is properly simulated in the system 100.

Furthermore, removing material in root-pass welding is properly simulated in the system 100. For example, in the real world, grinding of the root pass may be performed prior to subsequent welding passes. Similarly, system 100 may simulate a grinding pass that removes material from the virtual weld joint. It will be appreciated that the material removed may be modeled as a negative displacement on the wexel map. That is to say that the grinding pass removes material that is modeled by the system 100 resulting in an altered bead contour. Simulation of the grinding pass may be automatic, which is to say that the system 100 removes a predetermined thickness of material, which may be respective to the surface of the root pass weld bead.

In an alternative embodiment, an actual grinding tool, or grinder, may be simulated that turns on and off by activation of the mock welding tool 160 or another input device. It is noted that the grinding tool may be simulated to resemble a real world grinder. In this embodiment, the user maneuvers the grinding tool along the root pass to remove material responsive to the movement thereof. It will be understood that the user may be allowed to remove too much material. In a manner similar to that described above, holes or other defects (described above) may result if the user grinds away too much material. Still, hard limits or stops may be implemented, i.e. programmed, to prevent the user from removing too much material or indicate when too much material is being removed.

In addition to the non-visible "puddle" particles described herein, the system 100 also uses three other types of visible particles to represent Arc, Flame, and Spark effects, in accordance with an embodiment of the present invention. These types of particles do not interact with other particles of any type but interact only with the displacement map. While these particles do collide with the simulated weld surface, they do not interact with each other. Only Puddle particles interact with each other, in accordance with an embodiment of the present invention. The physics of the Spark particles is setup such that the Spark particles bounce around and are rendered as glowing dots in virtual reality space.

The physics of the Arc particles is setup such that the Arc particles hit the surface of the simulated coupon or weld bead and stay for a while. The Arc particles are rendered as larger dim bluish-white spots in virtual reality space. It takes many such spots superimposed to form any sort of visual image. The end result is a white glowing nimbus with blue edges.

The physics of the Flame particles is modeled to slowly raise upward. The Flame particles are rendered as medium sized dim red-yellow spots. It takes many such spots superimposed to form any sort of visual image. The end result is blobs of orange-red flames with red edges raising upward and fading out. Other types of non-puddle particles may be implemented in the system 100, in accordance with other embodiments of the present invenntion. For example, smoke particles may be modeled and simulated in a similar manner to flame particles.

The final steps in the simulated visualization are handled by the vertex and pixel shaders provided by the shaders 117 of the GPUs 115. The vertex and pixel shaders apply Puddle and Displacement, as well as surface colors and reflectivity altered due to heat, etc. The Extra (E) channel of the PHED wexel format, as discussed earlier herein, contains all of the extra information used per wexel. In accordance with an embodiment of the present invention, the extra information includes a non virgin bit (true=bead, false=virgin steel), a slag bit, an undercut value (amount of undercut at this wexel where zero equals no undercut), a porosity value (amount of porosity at this wexel where zero equals no porosity), and a bead wake value which encodes the time at which the bead solidifies. There are a set of image maps associated with different coupon visuals including virgin steel, slag, bead, and porosity. These image maps are used both for bump mapping and texture mapping. The amount of blending of these image maps is controlled by the various flags and values described herein.

A bead wake effect is achieved using a 1D image map and a per wexel bead wake value that encodes the time at which a given bit of bead is solidified. Once a hot puddle wexel location is no longer hot enough to be called "puddle", a time is saved at that location and is called "bead wake". The end result is that the shader code is able to use the 1D texture map to draw the "ripples" that give a bead its unique appearance which portrays the direction in which the bead was laid down. In accordance with an alternative embodiment of the present invention, the system 100 is capable of simulating, in virtual reality space, and displaying a weld bead having a real-time weld bead wake characteristic resulting from a real-time fluidity-to-solidification transition of the simulated weld puddle, as the simulated weld puddle is moved along a weld trajectory.

In accordance with an alternative embodiment of the present invention, the system 100 is capable of teaching a user how to troubleshoot a welding machine. For example, a troubleshooting mode of the system may train a user to make sure he sets up the system correctly (e.g., correct gas flow rate, correct power cord connected, etc.) In accordance with another alternate embodiment of the present invention, the system 100 is capable of recording and playing back a welding session (or at least a portion of a welding session, for example, N frames). A track ball may be provided to scroll through frames of video, allowing a user or instructor to critique a welding session. Playback may be provided at selectable speeds as well (e.g., full speed, half speed, quarter speed). In accordance with an embodiment of the present invention, a split-screen playback may be provided, allowing two welding sessions to be viewed side-by-side, for example, on the ODD 150. For example, a "good" welding session may be viewed next to a "poor" welding session for comparison purposes.

Importing and Analyzing External Data

In accordance with certain embodiments, external data may be imported into the virtual reality welding system and analyzed to help characterize, for example, a student welder's progress and to aid in the training of the student welder.

One embodiment provides a method of importing and analyzing data. The method includes importing a first data set of welding quality parameters, being representative of a quality of a weld generated by a student welder during a real-world welding activity corresponding to a defined welding process, into a virtual reality welding system. The method also includes comparing a second data set of welding quality parameters stored on the virtual reality simulator, being representative of a quality of a virtual weld generated by the student welder during a simulated welding activity corresponding to the defined welding process on the virtual reality welding system, to the first data set using a programmable processor-based subsystem of the virtual reality welding system. The method further includes generating a numerical comparison score in response to the comparing using the programmable processor-based subsystem of the virtual reality welding system. The numerical comparison score may be representative of a total deviation in weld quality between the first data set and the second data set. The method may also include importing a third data set of welding quality parameters, being representative of a quality of an ideal weld generated by an expert welder during a real-world welding activity corresponding to the defined welding process, into the virtual reality welding system. The expert welder may be a robotic welder or a human welder, for example. The method may further include comparing the second data set to the third data set using the programmable processor-based subsystem of the virtual reality welding system, and generating a numerical student score in response to the comparing using the programmable processor-based subsystem of the virtual reality welding system. The numerical student score may be representative of a total deviation in weld quality from the ideal weld, for example.

FIG. 20 illustrates the concept of importing welding quality parameters 2020 into a virtual reality welding system 100 from a real-world welding machine 2000. The welding quality parameters 2020 may be imported into the virtual reality welding system 100 via wired means or wireless means through a communication device 2010. In accordance with an embodiment, the communication device 2010 is operatively connected to the programmable processor-based subsystem 110 and provides all of the circuitry and/or software for receiving data in a digitally communicated manner (see FIG. 1). For example, the communication device 2010 may include an Ethernet port and Ethernet-capable receiving circuitry. As another example, the communication device 2010 may provide a wireless Bluetooth™ communication connection. Alternatively, the communication device 2010 may be a device that accepts and reads a non-transitory computer-readable medium such as a computer disk or a flash drive data storage device, for example. As a further alternative embodiment, the communication device 2010 may be a modem device providing connection to the internet. Other types of communication devices are possible as well, in accordance with various other embodiments.

Various types of welding quality parameters are discussed in the published U.S. patent application Ser. No. 13/453,124 which is incorporated herein by reference. However, other types of welding quality parameters may be possible as well, in accordance with other embodiments. The welding quality parameters represent a quality of a weld generated by, for example, a student welder. Quality parameters may be derived from measured or simulated welding parameters, as discussed later herein. Some examples of measured or simulated welding parameters are a count of the measurements taken, a mean voltage, a root mean square voltage, a voltage variance, a mean current, a root mean square current, a current variance, a mean wire feed speed, a root mean square wire feed speed, and a wire feed speed variance. Some examples of welding quality parameters are a quality count standard deviation, a quality voltage average, a quality voltage standard deviation, a quality current average, a quality current standard deviation, a quality voltage variance average, a quality voltage variance standard deviation, a quality current average, a quality current variance standard deviation, a quality wire feed speed average, a quality wire feed speed standard deviation, a quality wire feed speed variance average, and a quality wire feed speed variance standard deviation.

Figure 21:
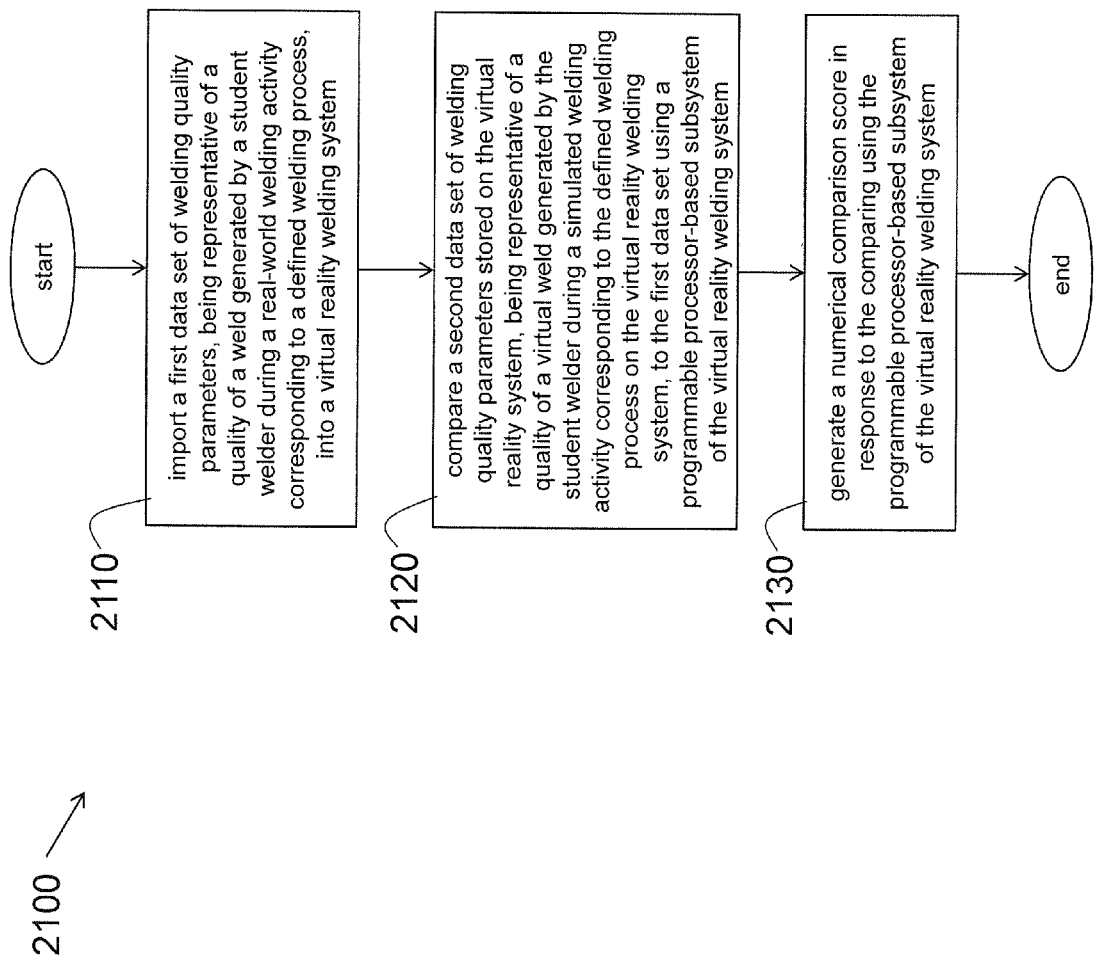
FIG. 21 is a flow chart of an embodiment of a method to compare a student welder's real-world welding activity to the student welder's virtual welding activity.

FIG. 21 is a flow chart of an embodiment of a method 2100 to compare a student welder's real-world welding activity to the student welder's virtual welding activity. In step 2110, a first data set of welding quality parameters, being representative of a quality of a weld generated by a student welder during a real-world welding activity corresponding to a defined welding process, is imported into the virtual reality welding system 100. In step 2120, a second data set of welding quality parameters stored on the virtual reality welding system 100, being representative of a quality of a virtual weld generated by the student welder during a simulated welding activity corresponding to the defined welding process on the virtual reality welding system 100, is compared to the first data set using the programmable processor-based subsystem 110 of the virtual reality welding system 100. In step 2130, a numerical comparison score is generated in response to the comparing step using the programmable processor-based subsystem 110 of the virtual reality welding system 100.

The method 2100 of FIG. 21 may represent the situation where the student welder, after having trained to perform the defined welding process on the virtual reality welding system 100, transitions to a corresponding real-world welding system 2000 and performs the same defined welding process in the real-world, actually creating a real weld. Welding quality parameters are generated and stored in both the virtual situation and the real-world situation. The method 2100 allows the student welder to compare his welding performance in the real-world to his welding performance in the virtual world, with respect to the defined welding process. Examples of defined welding processes include gas metal arc welding (GMAW) processes, stick welding processes, flux cored arc welding (FCAW) processes, and gas tungsten arc welding (GTAW) processes. Other types of defined welding processes are possible as well, in accordance with various other embodiments.

The numerical comparison score may be representative of a total deviation in weld quality between the first data set and the second data set. Alternatively, the numerical comparison score may be representative of a total closeness in weld quality of the first data set to the second data set. For example, the numerical comparison score may be calculated by taking a difference between each corresponding weld quality parameter from the virtual welding activity and the real-world welding activity, weighting each difference, and summing the weighted differences. Other methods of generating the numerical comparison score are possible as well, in accordance with various other embodiments. For example, the published U.S. patent application Ser. No. 13/453,124 which is incorporated herein by reference discloses methods of calculating such scores. As one example, each quality value may be compared to an expected quality value to determine if a difference between the quality value and the expected quality value exceeds a predetermined threshold. If the difference exceeds the threshold, the quality value may be weighted with a magnitude weight based on the difference, and the quality value may be weighted with a time contribution weight based on a time contribution of the state to its wave shape. All of the quality values, including any weighted quality values, obtained during said arc welding process may be used to determine the numerical score. Furthermore, the numerical comparison score may be normalized to a range of 0% to 100%, for example, where 0% represents a maximum deviation and 100% represents a minimum deviation.

Figure 22:
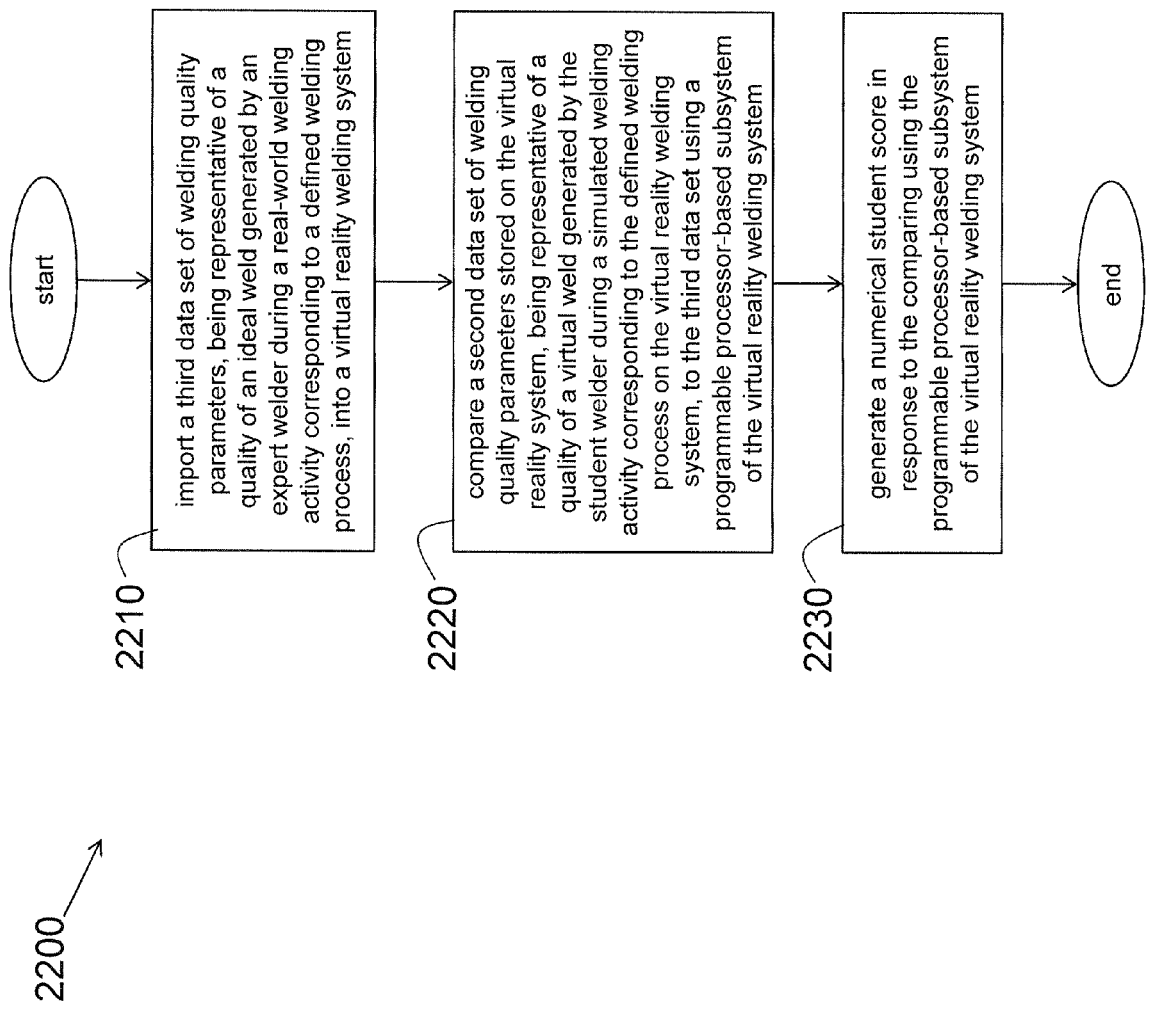
FIG. 22 is a flow chart of an embodiment of a method to compare a student welder's virtual welding activity to an expert welder's real-world welding activity.

FIG. 22 is a flow chart of an embodiment of a method 2200 to compare a student welder's virtual welding activity to an expert welder's real-world welding activity. In step 2210, a third data set of welding quality parameters, being representative of a quality of an ideal weld generated by an expert welder during a real-world welding activity corresponding to a defined welding process, is imported into the virtual reality welding system 100. The expert welder may be an experienced human welder or a programmed robotic welder, for example. In step 2220, a second data set of welding quality parameters stored on the virtual reality system, being representative of a quality of a virtual weld generated by the student welder during a simulated welding activity corresponding to the defined welding process on the virtual reality welding system 100, is compared to the third data set using the programmable processor-based subsystem 110 of the virtual reality welding system 100. In step 2230, a numerical student score is generated in response to the comparing step using the programmable processor-based subsystem 110 of the virtual reality welding system 100.

The method 2200 of FIG. 22 may represent the situation where the student welder is learning to perform the defined welding process using the virtual reality welding system 100, and wants to know how much progress he is making with respect to an ideal weld created in the real-world. Again, welding quality parameters are generated and stored in both the virtual situation and the real-world situation. The method 2200 allows the student welder to compare his welding performance in the virtual world to an expert's welding performance in the real world, with respect to the defined welding process. The numerical student score, similar to the numerical comparison score, may be representative of a total deviation in weld quality from the ideal weld. Alternatively, the numerical student score may be representative of a total closeness in weld quality to the ideal weld. For example, the numerical student score may be calculated by taking a difference between each corresponding weld quality parameter from the student's virtual welding activity and the expert's real-world welding activity, weighting each difference, and summing the weighted differences. Other methods of generating the numerical student score are possible as well, in accordance with various other embodiments. Similar to the numerical comparison score, the numerical student score may be normalized to a range of 0% to 100%.

Another embodiment provides a method of importing and analyzing data. The method includes importing a first data set of measured welding parameters, generated during a real-world welding activity corresponding to a defined welding process performed by an expert welder using a real-world welding machine, into a virtual reality welding system. The expert welder may be a robotic welder or a human welder. The method also includes storing a second data set of simulated welding parameters, generated during a simulated welding activity corresponding to the defined welding process as performed by a student welder using the virtual reality welding system, on the virtual reality welding system. The method further includes calculating a plurality of expert welding quality parameters based on the first data set using the programmable processor-based subsystem of the virtual reality welding system. The method also includes calculating a plurality of student welding quality parameters based on the second data set using the programmable processor-based subsystem of the virtual reality welding system. The method may also include comparing the plurality of expert welding quality parameters to the plurality of student welding quality parameters using the programmable processor-based subsystem of the virtual reality welding system. The method may further include generating a numerical student score in response to the comparing using the programmable processor-based subsystem of the virtual reality welding system. The numerical student score may be representative of a total deviation in weld quality from the weld of ideal quality, for example.

Figure 23:
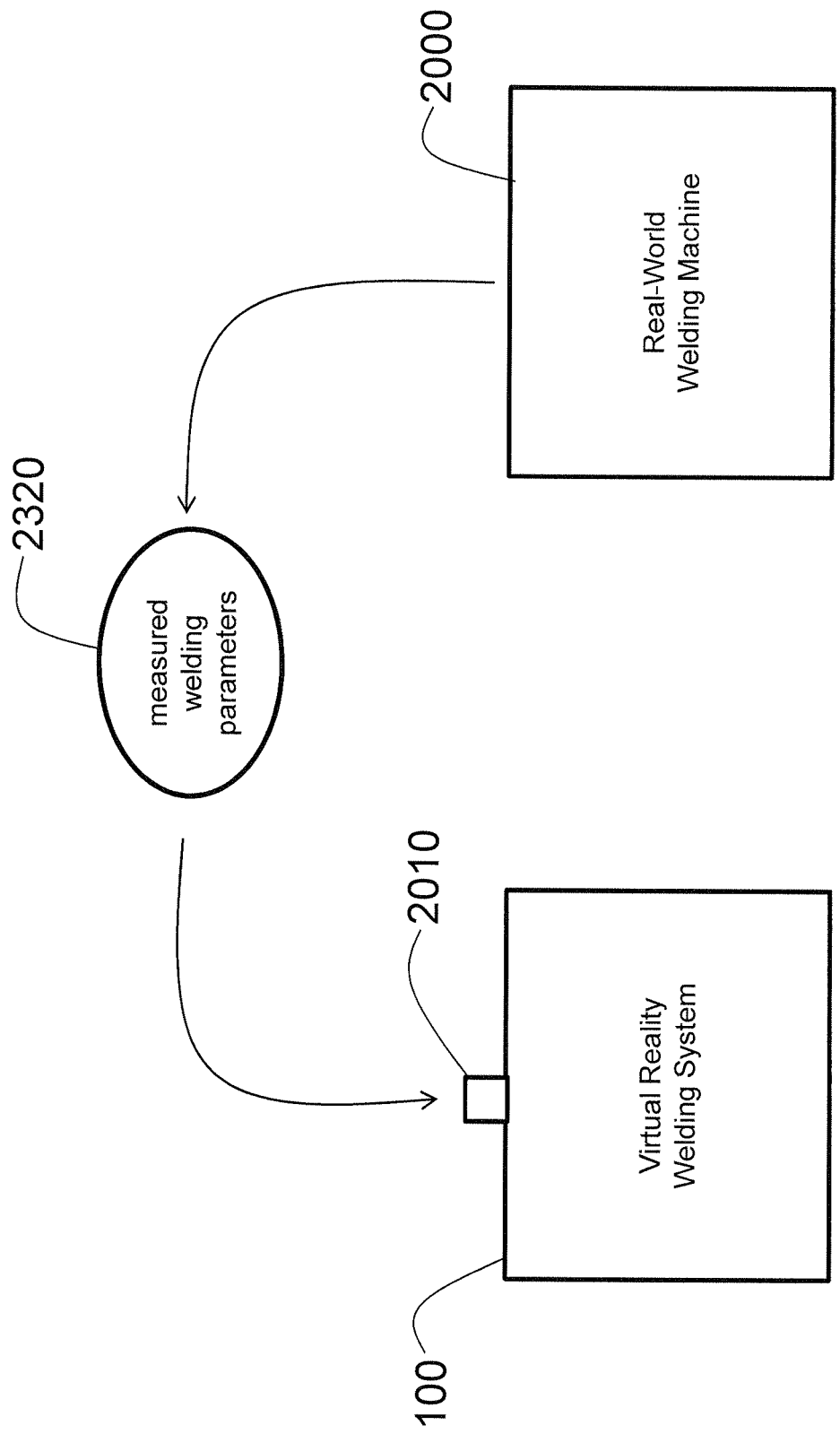
FIG. 23 illustrates the concept of importing measured welding parameters into a virtual reality welding system from a real-world welding machine.

FIG. 23 illustrates the concept of importing measured welding parameters into a virtual reality welding system 100 from a real-world welding machine 2000. The measured welding parameters 2320 may be imported into the virtual reality welding system 100 via wired means or wireless means through the communication device 2010. In accordance with an embodiment, the communication device 2010 is operatively connected to the programmable processor-based subsystem 110 and provides all of the circuitry and/or software for receiving data in a digitally communicated manner (see FIG. 1). For example, the communication device 2010 may include an Ethernet port and Ethernet-capable receiving circuitry. As another example, the communication device 2010 may provide a wireless Bluetooth™ communication connection. Alternatively, the communication device 2010 may be a device that accepts and reads a non-transitory computer-readable medium such as a computer disk or a flash drive data storage device, for example. As a further alternative embodiment, the communication device 2010 may be a modem device providing connection to the internet. Other types of communication devices are possible as well, in accordance with various embodiments.

Various types of measured welding parameters are discussed in the published U.S. patent application Ser. No. 13/453,124 which is incorporated herein by reference. However, other types of measured welding parameters may be possible as well, in accordance with other embodiments. The measured welding parameters are representative of actual welding parameters that occur during a welding activity for a defined welding process where a welding wire advances toward a workpiece to create a weld. In accordance with an embodiment, quality parameters may be derived from measured welding parameters. Some examples of measured welding parameters are a count of the measurements taken, a mean voltage, a root mean square voltage, a voltage variance, a mean current, a root mean square current, and a current variance.

Figure 24:
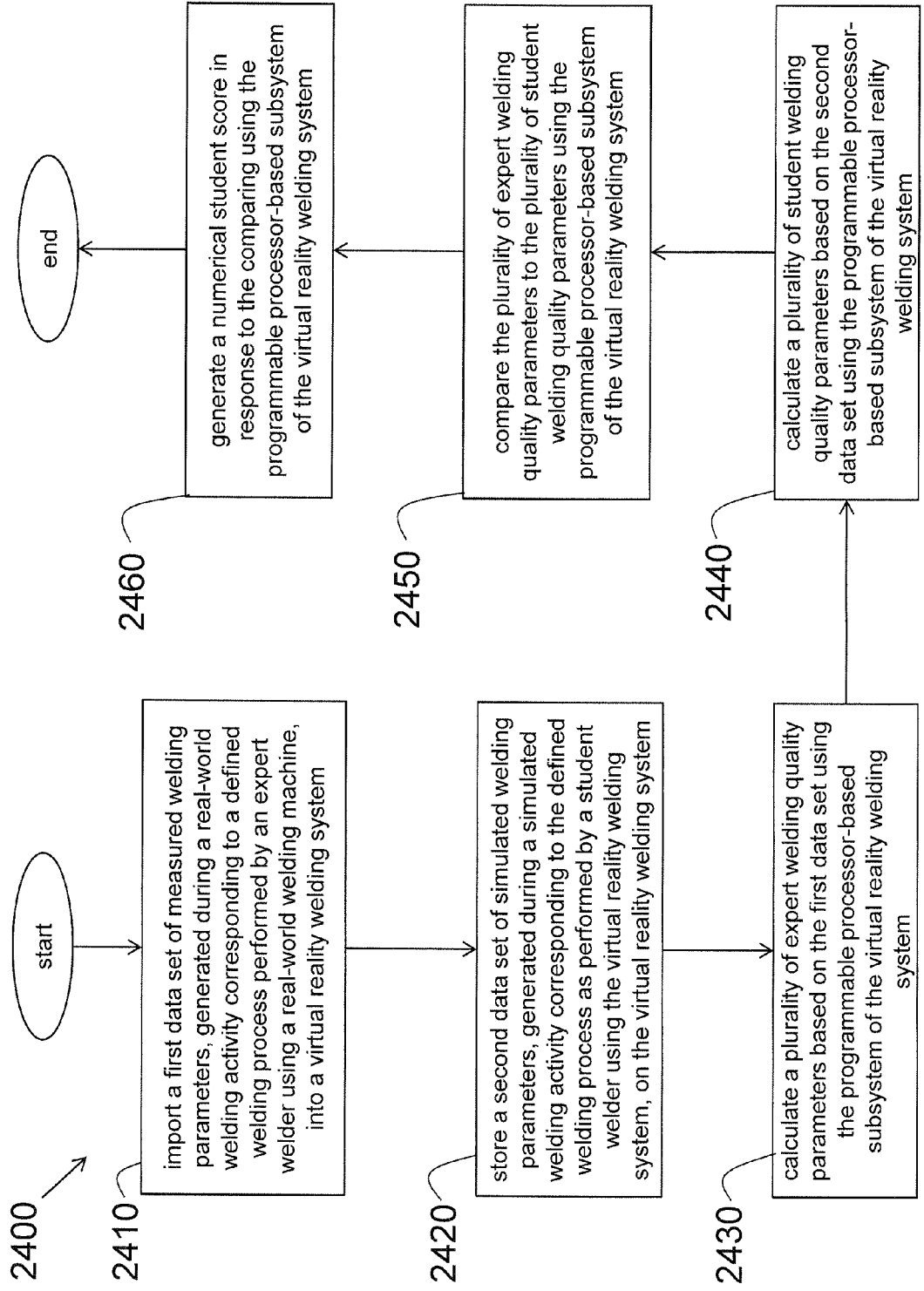
FIG. 24 is a flow chart of a first embodiment of a method of generating a plurality of student welding quality parameters and a numerical student score.

FIG. 24 is a flow chart of a first embodiment of a method 2400 of generating a plurality of student welding quality parameters and a numerical student score. In step 2410, a first data set of measured welding parameters, generated during a real-world welding activity corresponding to a defined welding process performed by an expert welder using the real-world welding machine 2000, is imported into the virtual reality welding system 100. The expert welder may be an experienced human welder or a robotic welder, for example. In step 2420, a second data set of simulated welding parameters, generated during a simulated welding activity corresponding to the defined welding process as performed by a student welder using the virtual reality welding system 100, is stored on the virtual reality welding system 100. The simulated welding parameters correspond to the measured welding parameters, but are generated in the virtual reality welding system 100 as part of the welding simulation, as opposed to in the real-world welding machine. In the virtual reality welding system 100, welding parameters (e.g., current and derivations thereof, voltage and derivations thereof, wire feed speed and derivations thereof) are simulated as part of simulating a virtual weld puddle having real-time molten metal fluidity and heat dissipation characteristics, for example.

In step 2430, a plurality of expert welding quality parameters are calculated based on the first data set using the programmable processor-based subsystem 110 of the virtual reality welding system 100. In step 2440, a plurality of student welding quality parameters are calculated based on the second data set using the programmable processor-based subsystem 110 of the virtual reality welding system 100. The calculating of quality parameters based on measured welding parameters is disclosed in the published U.S. patent application Ser. No. 13/453,124 which is incorporated herein by reference. The calculating of quality parameters based on simulated welding parameters may be performed in a similar manner.

In the method 2400, the student welding quality parameters are derived from the simulated welding parameters that were generated by the virtual reality welding system during the student welding activity, and the measured welding parameters that were generated by an expert during the real-world welding activity and imported from the real-world welding machine. Therefore, the student welding quality parameters are representative of the student's performance in virtual reality space with respect to an expert welder's performance in the real world.

In step 2450, the plurality of expert welding quality parameters are compared to the plurality of student welding quality parameters using the programmable processor-based subsystem 110 of the virtual reality welding system 100. In step 2460, a numerical student score is calculated in response to the comparing step using the programmable processor-based subsystem 110 of the virtual reality welding system 100. The numerical student score may be representative of a total deviation in weld quality from the ideal weld. Alternatively, the numerical student score may be representative of a total closeness in weld quality to the ideal weld. For example, the numerical student score may be calculated by taking a difference between each corresponding weld quality parameter of the student welding quality parameters and the expert welding quality parameters, weighting each difference, and summing the weighted differences. Other methods of generating the numerical student score are possible as well, in accordance with various other embodiments. Again, the numerical student score may be normalized to a range of 0% to 100%, for example.

A further embodiment provides a method of analyzing simulated welding parameters. The method includes storing a first data set of simulated welding parameters, generated during a first simulated welding activity corresponding to a defined welding process performed by an expert welder using a virtual reality welding system, on the virtual reality welding system. The expert welder may be a robotic welder or a human welder, for example. The method also includes storing a second data set of simulated welding parameters, generated during a second simulated welding activity corresponding to the defined welding process as performed by a student welder using the virtual reality welding system, on the virtual reality welding system. The method further includes calculating a plurality of expert welding quality parameters based on the first data set using a programmable processor-based subsystem of the virtual reality system. The method further includes calculating a plurality of student welding quality parameters based on the second data set using a programmable processor-based subsystem of the virtual reality system. The method may further include comparing the plurality of expert welding quality parameters to the plurality of student welding quality parameters using the programmable processor-based subsystem of the virtual reality welding system. The method may also include generating a numerical student score in response to the comparing using the programmable processor-based subsystem of the virtual reality welding system. The numerical score may be representative of a total deviation in weld quality from the weld of ideal quality, for example.

Figure 25:
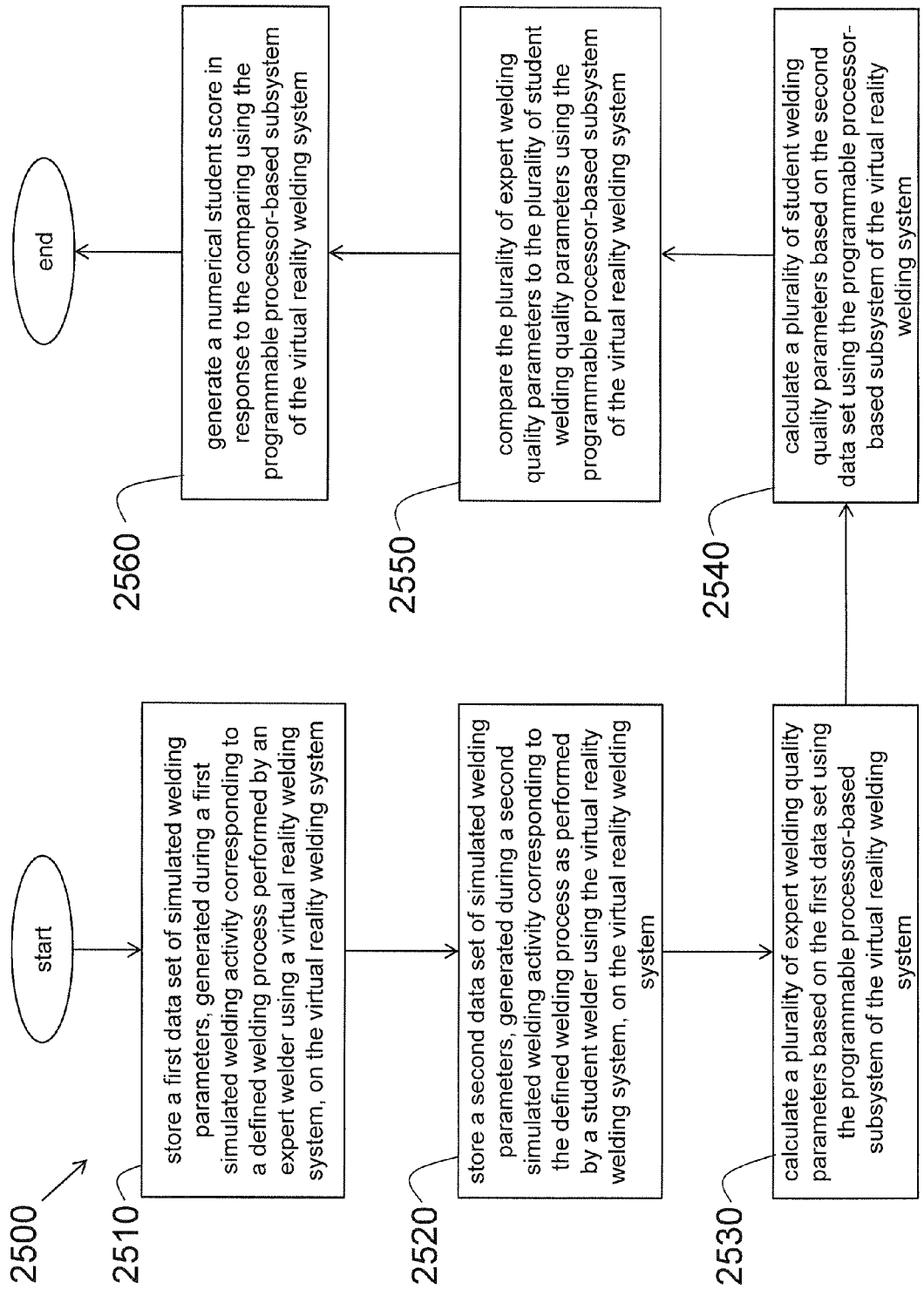
FIG. 25 is a flow chart of a second embodiment of a method of generating a plurality of student welding quality parameters and a numerical student score.

FIG. 25 is a flow chart of a second embodiment of a method 2500 of generating a plurality of student welding quality parameters and a numerical student score. In step 2510, a first data set of simulated welding parameters, generated during a first simulated welding activity corresponding to a defined welding process performed by an expert welder using the virtual reality welding system 100, is stored on the virtual reality welding system 100. The expert welder may be an experienced human welder or a robotic welder, for example. In step 2520, a second data set of simulated welding parameters, generated during a simulated welding activity corresponding to the defined welding process as performed by a student welder using the virtual reality welding system 100, is stored on the virtual reality welding system 100. The simulated welding parameters are generated in the virtual reality welding system 100 as part of the welding simulation. In step 2530, a plurality of expert welding quality parameters are calculated based on the first data set using the programmable processor-based subsystem 110 of the virtual reality welding system 100. In step 2540, a plurality of student welding quality parameters are calculated based on the second data set using the programmable processor-based subsystem 110 of the virtual reality welding system 100. The calculating of quality parameters, whether measured are simulated, is disclosed in the published U.S. patent application Ser. No. 13/453,124 which is incorporated herein by reference.

In the method 2500, the welding quality parameters are derived from the simulated welding parameters generated by the virtual reality welding system during the expert welding activity and the student welding activity. Therefore, the student welding quality parameters are representative of the student's performance in virtual reality space and the expert welding quality parameters are representative of the expert's performance in virtual reality space. The student welding quality parameters may next be compared to the expert welding quality parameters.

In step 2550, the plurality of expert welding quality parameters are compared to the plurality of student welding quality parameters using the programmable processor-based subsystem 110 of the virtual reality welding system 100. In step 2560, a numerical student score is calculated in response to the comparing step using the programmable processor-based subsystem 110 of the virtual reality welding system 100. The numerical student score may be representative of a total deviation in weld quality from the ideal weld. Alternatively, the numerical student score may be representative of a total closeness in weld quality to the ideal weld. For example, the numerical student score may be calculated by taking a difference between each corresponding weld quality parameter of the student welding quality parameters and the expert welding quality parameters, weighting each difference, and summing the weighted differences. Other methods of generating a numerical student score are possible as well, in accordance with various other embodiments.

Another embodiment provides a method of importing and analyzing data. The method includes importing a digital model representative of a welded custom assembly into a virtual reality welding system. The method also includes analyzing the digital model to segment the digital model into a plurality of sections using a programmable processor-based subsystem of the virtual reality welding system, wherein each section of the plurality of sections corresponds to a single weld joint type of the welded custom assembly. The method further includes matching each section of the plurality of sections to a virtual welding coupon of a plurality of virtual welding coupons modeled in the virtual reality welding system using the programmable processor-based subsystem of the virtual reality welding system. The method may also include generating a virtual welding training program that uses the virtual welding coupons corresponding to the matched sections of the digital model representative of the welded custom assembly using the programmable processor-based subsystem of the virtual reality welding system. Each of the virtual welding coupons may correspond to a mock welding coupon of the virtual reality welding system. The single weld joint type may include one of a butt joint, a tee joint, a corner joint, an edge joint, or a lap joint, for example. Other single weld joint types are possible as well, in accordance with various other embodiments.

Figure 26:
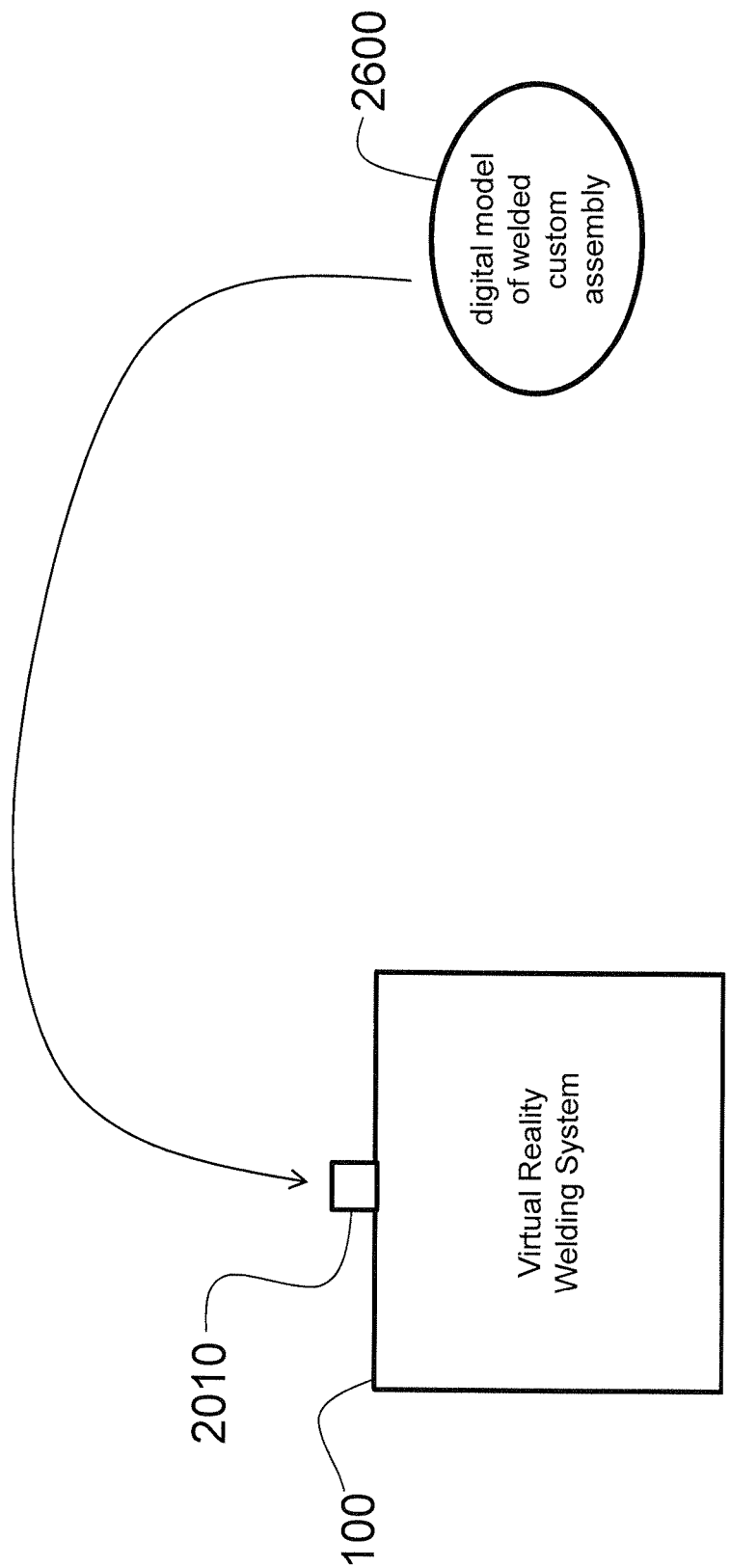
FIG. 26 illustrates the concept of importing a digital model representative of a welded custom assembly into a virtual reality welding system.

FIG. 26 illustrates the concept of importing a digital model 2600 representative of a welded custom assembly into the virtual reality welding system 100. The welded custom assembly may correspond to the final assembled product of a plurality of metal parts that are welded together. A manufacturer may have many such final assembled products to produce and, therefore, may need to train one or more welders to efficiently and reliably weld the metal parts together. In accordance with an embodiment, the digital model 2600 is a computer-aided design (CAD) model of a custom welded assembly represented in three-dimensional space, for example. Other types of digital models may be possible as well, in accordance with various other embodiments of the present invention. For example, a digital model may correspond to a custom welded assembly shown in multiple two-dimensional views, as on a blue print. The term "digital model" as used herein refers to data and/or instructions that are in a digital format (e.g., a digital electronic format stored on a computer-readable medium) that may be read by a computer-based or processor-based apparatus such as the virtual reality welding system 100.

The digital model 2600 may be imported into the virtual reality welding system 100 via wired means or wireless means through a communication device 2010. In accordance with an embodiment, the communication device 2010 is operatively connected to the programmable processor-based subsystem 110 and provides all of the circuitry and/or software for receiving data in a digitally communicated manner (see FIG. 1). For example, the communication device 2010 may include an Ethernet port and Ethernet-capable receiving circuitry. As another example, the communication device 2010 may provide a wireless Bluetooth™ communication connection. Alternatively, the communication device 2010 may be a device that accepts and reads a non-transitory computer-readable medium such as a computer disk or a flash drive data storage device, for example. As a further alternative embodiment, the communication device 2010 may be a modem device providing connection to the internet. Other types of communication devices are possible as well, in accordance with various other embodiments.

Figure 27:
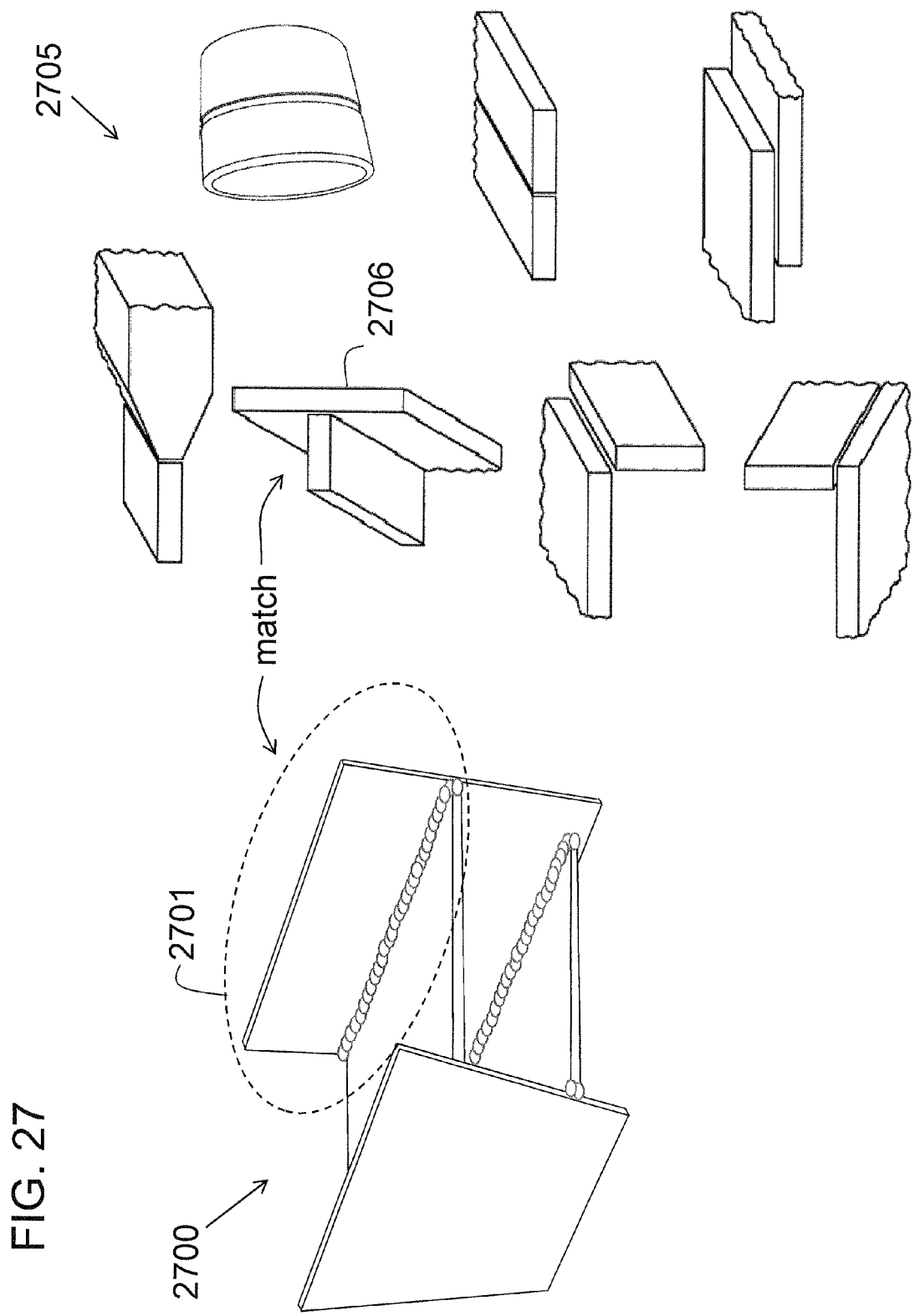
FIG. 27 illustrates the concept of matching sections of a digital model representative of a welded custom part to a plurality of welding coupons.

FIG. 27 illustrates the concept of matching sections of a digital model 2600 representative of a welded custom assembly 2700 to a plurality of welding coupons 2705. For example, the welded custom assembly 2700 may be made up of a plurality of different weld joint types, joining together a plurality of different metal parts. In accordance with an embodiment, the virtual reality welding system 100 is configured to (i.e., programmed to) analyze the digital model 2600 of the custom welded assembly 2700 and segment the digital model 2600 into a plurality of sections, where each section corresponds to a weld joint type of the welded custom assembly 2700. Each section may be matched (or attempted to be matched) to one of the plurality of welding coupons 2705 as discussed with respect to the method 2800 of FIG. 28. For example, a section 2701 of the welded custom assembly 2700, as represented in the digital model 2600, may be matched to a welding coupon 2706.

In accordance with an embodiment, each welding coupon of the plurality of welding coupons 2705 is modeled in the virtual reality welding system 100 in virtual reality space and also exists as a mock welding coupon (e.g., a plastic part) that may be used by a user along with a mock welding tool during a virtual welding activity. The plurality of welding coupons may correspond to coupons having a butt joint, a tee joint, a corner joint, an edge joint, or a lap joint, for example. Welding coupons having other types of joints are possible as well, in accordance with various other embodiments.

FIG. 28 is a flowchart of an embodiment of a method 2800 to generate a virtual welding training program for a welded custom assembly 2700. In step 2810, a digital model 2600 representative of a welded custom assembly 2700 is imported into the virtual reality welding system 100, as illustrated in FIG. 26. In step 2820, the digital model is analyzed using the programmable processor-based subsystem 110 of the virtual reality welding system 100 to segment the digital model 2600 into a plurality of sections, wherein each section of the plurality of sections corresponds to a single weld joint type of the welded custom assembly.

In accordance with an embodiment, the analyzing includes recognizing features in the digital model that correspond to single weld joint types of the welded custom assembly using feature identification techniques. A feature, in computer aided design (CAD) model, may be a region of an assembly with some particular geometric or topological patterns that may relate to, for example, shape, functional, or manufacturing information. In feature recognition, the idea is to algorithmically extract higher level entities (e.g. manufacturing features) from lower level elements (e.g. surfaces, edges, etc.) of a CAD model. The exact types of algorithms used may be chosen and implemented with sound engineering judgment, based on the types of welded custom assemblies expected to be encountered.

In step 2830, each section of the plurality of sections is matched (or attempted to be matched) to a virtual welding coupon of a plurality of virtual welding coupons 2705 modeled in the virtual reality welding system 100 using the programmable processor-based subsystem 110 of the virtual reality welding system 100. In accordance with an embodiment, the feature matching includes using convolution masks or templates, tailored to specific features of the welding coupons. The output of the convolution process is highest at locations where a section matches the mask structure of a welding coupon. The exact types of matching techniques used may be chosen and implemented with sound engineering judgment, based on the types of welded custom assemblies expected to be encountered.

In step 2840, a virtual welding training program is generated that uses the virtual welding coupons corresponding to the matched sections of the digital model 2600 of the custom welded assembly 2700 using the programmable processor-based subsystem 110 of the virtual reality welding system 100. For example, the virtual welding training program may include a sequence of welding steps that direct a welder with respect to how to practice welding of the assembly 2700, using the matched welding coupons, in a particular order.

In summary, a real-time virtual reality welding system is disclosed. The system includes a programmable processor-based subsystem, a spatial tracker operatively connected to the programmable processor-based subsystem, at least one mock welding tool capable of being spatially tracked by the spatial tracker, and at least one display device operatively connected to the programmable processor-based subsystem. The system is capable of simulating, in virtual reality space, a weld puddle having real-time molten metal fluidity and heat dissipation characteristics. The system is further capable of importing data into the virtual reality welding system and analyzing the data to characterize a student welder's progress and to provide training.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. A system for simulating welding activity; said system comprising:
    a welding tool for a simulated welding operation;
    a spatial tracker which tracks a movement and orientation of said welding tool using at least one optical sensor;
    a welding coupon;
    a helmet comprising a first display device to display a simulated welding operation to a user;
    a simulated welding console having a user input system and a second display device to display said simulated welding operation; and
    a processor based subsystem located within said simulated welding console which is operatively coupled to said spatial tracker and receives information from said spatial tracker related to said movement and orientation of said welding tool, where said processor based subsystem generates a plurality of simulated welding parameters based on said movement and orientation of said welding tool;
    wherein during said simulated welding operation, said processor based subsystem models a simulated welding surface for said welding coupon and displays said simulated welding surface on each of said first and second display devices;
    wherein during said simulated welding operation, said processor based subsystem creates a simulated welding arc between an emitting end of said welding tool and said simulated welding surface and simulates a creation of a weld puddle have real-time molten metal fluidity, real-time heat dissipation and real-time heat absorption characteristics during said simulated welding operation;
    wherein said processor based subsystem models said simulated weld puddle such that regions of a surface of said simulated weld puddle have both a displacement value and a heat value, where each of said displacement values and heat values are changed dynamically during said simulated welding operation to display on each of said first and second display devices a simulated deposition of material into said simulated weld puddle, and said dynamic changes to each of said displacement and heat values are based on said movement and orientation of said welding tool and on said plurality of simulated welding parameters, where said first and second display devices display a color for each of said regions which is based on said heat values;
    wherein said processor based subsystem displays a simulated completed weld bead on said first and second display devices which is based on said movement and orientation of said welding tool, based on said simulated welding parameters and based on a cooling threshold value for a transition of said regions from a molten state to a solid state, and
    wherein said displacement values are such that a solidified surface of said simulated completed weld bead is displayed above said welding surface of said welding coupon.

2. The simulated welding system of claim 1, wherein said welding tool is an actual welding tool that can be used for a real world welding operation.

3. The simulated welding system of claim 1, wherein said optical sensor is mounted on said helmet.

4. The simulated welding system of claim 1, wherein said helmet further comprises an audio speaker which provides simulated welding sounds in real-time with the simulated welding operation.

5. The simulated welding system of claim 1, wherein said second display device displays said plurality of simulated welding parameters, in real-time, during said simulated welding operation.

6. The simulated welding system of claim 5, wherein at least one of said simulated welding parameters is displayed in graphical form in real time during said simulated welding operation.

7. The simulated welding system of claim 5, wherein said welding parameters include weld angle, travel angle, and travel speed.

8. The simulated welding system of claim 1, wherein said processor based subsystem compares at least one of said simulated welding parameters to a stored value for said at least one simulated welding parameter, and wherein said processor based subsystem displays said comparison on said second display device.

9. The simulated welding system of claim 8, wherein said comparison is displayed in graphical form.

10. The simulated welding system of claim 1, wherein said processor based subsystem compares at least one of said simulated welding parameters to a tolerance window defined by limits around a setpoint for said at least one simulated welding parameter, and wherein said processor based subsystem displays said comparison on said second display device.

11. The simulated welding system of claim 10, wherein said comparison is displayed in graphical form.

12. The simulated welding system of claim 1, wherein said processor based subsystem provides a score for each of said simulated welding parameters based on a comparison between said simulated welding parameters and a desired value for each of said simulated welding parameters, respectively.

13. The simulated welding system of claim 12, wherein each of said scores is a numerical score.

14. The simulated welding system of claim 1, wherein said processor based subsystem determines the presence of a discontinuity within said simulated weld bead, and where said discontinuity is the presence of at least one of spatter and porosity.

15. The simulated welding system of claim 14, wherein said first display device displays said discontinuity during said simulated welding operation, in real time, and in said completed simulated weld bead.

16. The simulated welding system of claim 1, wherein said first display device displays a plurality of visual cues during said simulated welding operation, where each of said plurality of visual cues is for a distinct one of said simulated welding parameters, and where said visual cues are displayed based on a deviation of said simulated welding parameters during said simulated welding operation from a desired value for each of said simulated welding parameters, respectively.

17. The simulated welding system of claim 1, wherein said processor based subsystem generates and displays on said first display device at least one welding effect, which can be any one of simulated welding sparks, simulated welding spatter, simulated arc glow and simulated porosity during said simulated welding operation, and where said at least one welding effect is displayed, in real time, based on at least one of said simulated welding parameters.

18. The simulated welding system of claim 1, wherein at least one of said displacement and heat values are changed dynamically based a distance between said regions and said emitting end of said welding tool.

19. The simulated welding system of claim 1, wherein when said heat value is higher than said cooling threshold value said first and second display devices display said regions in a simulated fluid state and when said heat value is lower than said cooling threshold value said first and second display devices display said regions in a solid state.

20. The simulated welding system of claim 1, wherein said processor based subsystem changes displacement values of at least some regions of said completed weld bead when said welding tool is used to make a second simulated weld bead over said completed weld bead, and where each of said completed weld bead and said second simulated weld bead are displayed on said first and second display devices at the same time.

21. The simulated welding system of claim 1, wherein said real-time molten metal fluidity and said heat dissipation characteristics are generated by a physics model operating on a least one GPU.

22. The simulated welding system of claim 1, wherein said first display device displays a weld bead wake characteristic during creation of said simulated weld bead, where said wake characteristic is generated based on a real time fluidity-to-solidification transition of said simulated weld puddle as said simulated weld puddle is moved.

23. A system for simulating welding activity; said system comprising:
a welding tool for a simulated welding operation;
a spatial tracker which tracks a movement and orientation of said welding tool using at least one optical sensor;
a welding coupon;
a helmet comprising a first display device to display a simulated welding operation to a user, and which comprises said at least one optical sensor;
a simulated welding console having a user input system and a second display device to display said simulated welding operation; and
a processor based subsystem located within said simulated welding console which is operatively coupled to said spatial tracker and receives information from said spatial tracker related to said movement and orientation of said welding tool, where said processor based subsystem generates a plurality of simulated welding parameters based on said movement and orientation of said welding tool and displays said plurality of simulated welding parameters on said second display device in real time during said simulated welding operation;
wherein during said simulated welding operation, said processor based subsystem models a simulated welding surface for said welding coupon and displays said simulated welding surface on each of said first and second display devices;
wherein during said simulated welding operation, said processor based subsystem creates a simulated welding arc between an emitting end of said welding tool and said simulated welding surface and simulates the creation of a weld puddle have real-time molten metal fluidity, real-time heat dissipation and real-time heat absorption characteristics during said simulated welding operation;
wherein said processor based subsystem models said simulated weld puddle such that regions of a surface of said simulated weld puddle have both a displacement value and a heat value, where each of said displacement values and heat values are changed dynamically during said simulated welding operation to display on each of said first and second display devices the simulated deposition of material into said simulated weld puddle, and said dynamic changes to each of said displacement and heat values are based on said movement and orientation of said welding tool and on said plurality of simulated welding parameters, where said first and second display devices display a color for each of said regions which is based on said heat values;
wherein said processor based subsystem displays a simulated completed weld bead on said first and second display devices which is based on said movement and orientation of said welding tool, based on said simulated welding parameters and based on a cooling threshold value for a transition of said regions from a molten state to a solid state, and
wherein said displacement values are such that a solidified surface of said simulated completed weld bead is displayed above said welding surface of said welding coupon.

24. The simulated welding system of claim 23, wherein said welding tool is an actual welding tool that can be used for a real world welding operation.

25. The simulated welding system of claim 23, wherein said helmet further comprises an audio speaker which provides simulated welding sounds in real-time with the simulated welding operation.

26. The simulated welding system of claim 23, wherein at least one of said simulated welding parameters is displayed in graphical form in real time during said simulated welding operation.

27. The simulated welding system of claim 23, wherein said welding parameters include weld angle, travel angle, and travel speed.

28. The simulated welding system of claim 23, wherein said processor based subsystem compares at least one of said simulated welding parameters to a stored value for said at least one simulated welding parameter, and wherein said processor based subsystem displays said comparison on said second display device.

29. The simulated welding system of claim 28, wherein said comparison is displayed in graphical form.

30. The simulated welding system of claim 23, wherein said processor based subsystem compares at least one of said simulated welding parameters to a tolerance window defined by limits around a setpoint for said at least one simulated welding parameter, and wherein said processor based subsystem displays said comparison on said second display device.

31. The simulated welding system of claim 30, wherein said comparison is displayed in graphical form.

32. The simulated welding system of claim 23, wherein said processor based subsystem provides a score for each of said simulated welding parameters based on a comparison between said simulated welding parameters and a desired value for each of said simulated welding parameters, respectively.

33. The simulated welding system of claim 32, wherein each of said scores is a numerical score.

34. The simulated welding system of claim 23, wherein said processor based subsystem determines the presence of a discontinuity within said simulated weld bead, and where said discontinuity is the presence of at least one of spatter and porosity.

35. The simulated welding system of claim 34, wherein said first display device displays said discontinuity during said simulated welding operation, in real time, and in said completed simulated weld bead.

36. The simulated welding system of claim 23, wherein said first display device displays a plurality of visual cues during said simulated welding operation, where each of said plurality of visual cues is for a distinct one of said simulated welding parameters, and where said visual cues are displayed based on a deviation of said simulated welding parameters during said simulated welding operation from a desired value for each of said simulated welding parameters, respectively.

37. The simulated welding system of claim 23, wherein said processor based subsystem generates and displays on said first display device at least one welding effect, which can be any one of simulated welding sparks, simulated welding spatter, simulated arc glow and simulated porosity during said simulated welding operation, and where said at least one welding effect is displayed, in real time, based on at least one of said simulated welding parameters.

38. The simulated welding system of claim 23, wherein at least one of said displacement and heat values are changed dynamically based a distance between said regions and said emitting end of said welding tool.

39. The simulated welding system of claim 23, wherein when said heat value is higher than said cooling threshold value said first and second display devices display said regions in a simulated fluid state and when said heat value is lower than said cooling threshold value said first and second display devices display said regions in a solid state.

40. The simulated welding system of claim 23, wherein said processor based subsystem changes displacement values of at least some regions of said completed weld bead when said welding tool is used to make a second simulated weld bead over said completed weld bead, and where each of said completed weld bead and said second simulated weld bead are displayed on said first and second display devices at the same time.

41. The simulated welding system of claim 23, wherein said real-time molten metal fluidity and said heat dissipation characteristics are generated by a physics model operating on a least one GPU.

42. The simulated welding system of claim 23, wherein said first display device displays a weld bead wake characteristic during creation of said simulated weld bead, where said wake characteristic is generated based on a real time fluidity-to-solidification transition of said simulated weld puddle as said simulated weld puddle is moved.

* * * * *